(12) United States Patent
Seo et al.

(10) Patent No.: US 7,488,854 B2
(45) Date of Patent: Feb. 10, 2009

(54) DITERPENOID COMPOUNDS IMPARTING STRESS RESISTANCE TO PLANTS

(75) Inventors: Shigemi Seo, Ibaraki (JP); Yuko Ohashi, Ibaraki (JP); Hideharu Seto, Saitama (JP); Shigeo Yoshida, Saitama (JP)

(73) Assignees: The National Institute of Agrobiological Sciences, Ibaraki (JP); Riken, Saitama (JP)

( * ) Notice: Subject to any disclaimer, the term of this patent is extended or adjusted under 35 U.S.C. 154(b) by 642 days.

(21) Appl. No.: 10/507,756

(22) PCT Filed: Mar. 12, 2003

(86) PCT No.: PCT/JP03/02965

§ 371 (c)(1),
(2), (4) Date: Jul. 13, 2005

(87) PCT Pub. No.: WO03/076375

PCT Pub. Date: Sep. 18, 2003

(65) Prior Publication Data

US 2006/0003896 A1 Jan. 5, 2006

(30) Foreign Application Priority Data

Mar. 14, 2002 (JP) ............... 2002-070987
Jun. 24, 2002 (JP) ............... 2002-183722

(51) Int. Cl.
C07C 35/27 (2006.01)
A01N 31/06 (2006.01)
A01N 31/04 (2006.01)

(52) U.S. Cl. .............. 568/819; 514/729; 514/706; 514/724; 514/743; 514/744; 514/756; 514/747

(58) Field of Classification Search ............... 514/729, 514/706, 724, 743, 744, 756, 747; 568/819
See application file for complete search history.

(56) References Cited

FOREIGN PATENT DOCUMENTS

JP 04-342507 11/1992
WO WO98/47362 10/1998

OTHER PUBLICATIONS

Oshima, Y. et al., "Sterebins E, F, G and H, Diterpenoids of *Stevia Rebaudiana* Leaves", *Phytochemistry*, 27(2):624-626, 1988.
Li and Kuo, "Labdane-Type Diterpenoids from the Wood of *Cunninghamia konishil*", *Chem Pharm. Bull.*, 50(4):498-500, 2002.
International Search Report (ISR) dated Jun. 24, 2003 from PCT/JP03/02965.

*Primary Examiner*—Elvis O Price
(74) *Attorney, Agent, or Firm*—Peter J. Dehlinger; Susan J. Meyers Fitch King & Spalding LLP

(57) ABSTRACT

The present invention provides a compound having the following structure:

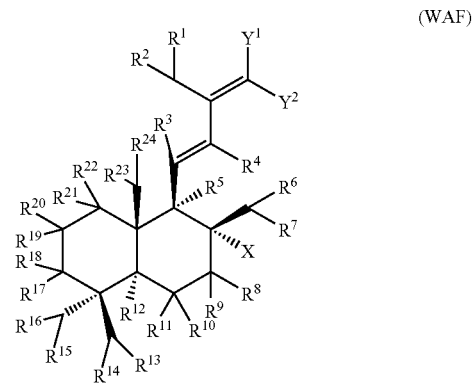

(WAF)

wherein, in the formula:
X is selected from the group consisting of hydroxy, substituted hydroxy, halogen, thiol, and substituted thiol;
one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and
$R^1$-$R^{24}$ are independently selected from the group of hydrogen, alkyl, and substituted alkyl.

40 Claims, 12 Drawing Sheets

Fig. 12

DITERPENOID COMPOUNDS IMPARTING STRESS RESISTANCE TO PLANTS

BACKGROUND OF THE INVENTION

1. Field of the Invention

The present invention relates to novel diterpenoid compounds. More particularly, it relates to novel diterpenoid compounds imparting stress resistance to plants, their uses and methods of synthesizing the same.

2. Background of the Invention

Organisms such as plants are exposed to various stresses (e.g., injury, insect pests, disease and the like) and are required to protect themselves during their lifespan. Such stresses are highly likely to cause damage which can threaten survival of plants, as compared to organisms such as animals which can move by themselves.

As used herein, "wound" refers to an injury to a plant caused by cutting, friction, compression, or being fed upon by an insect or Herviora, and physiological functions of the injured sites and broader regions are disturbed. Wounds due to worms, insects or the like are referred to as wounds due to an insect pest. In addition to wounds due to such physical injuries, wounds include those due to air pollutants, or chemical causes such as alkali, acids, heavy metals and the like, as well as those due to biological causes such as infection by pathogens including viruses, bacteria, fungi and the like. Wounds due to microorganisms such as viruses, bacteria, fungi or the like are particularly referred to as disease. Against wounds caused by such physical, chemical, or biological causes, organisms such as plants have particular defense mechanisms which have adapted themselves to the environments that they reside in.

For example, injured plants must immediately cure their wound, recover their ability to absorb water etc., from roots, and prevent invasion of pathogens from the roots. When the tissues are injured, hydrogen peroxide is generated, and lignification, suberization, and oxidative cross-linking of hydroxyproline-rich proteins are started, and cell walls are repaired and reinforced (Bradley, D. et al. Cell, 79, 21-30, 1992). This prevents moisture transpiration from the wound and also serves as a physical barrier against the invasion of pathogens. When a plant is wounded, the enzymatic activity of phenylalanine ammonia lyase, which is a rate-limiting enzyme of phenylpropanoid, is elevated and the production of polyphenol and lignin, both of which have antibiotic actions, are elevated. It is known that the plants infected with pathogens newly produce a series of proteins which are referred to as pathogenesis-related proteins (also referred to as PR proteins). Two of the PR proteins is chitinase and –1,3-glucanase and these proteins are produced when a plant is wounded. It is believed that these enzymes inhibit the growth of bacteria/fungi by degrading chitin and glucan, respectively, both of which are cell wall components of bacteria/fungi, thereby these enzymes protect the plants from infection with pathogens via the wound.

A protease inhibitor is also produced for the plants' defense against being fed by insects. Protease inhibitor is a general name for a material which inhibits an enzyme, spevifically a protease which has proteolytic activity and is also induced by infection with pathogens. The leaves of tomato and potato plants induce the production of protease inhibitor II upon being fed upon by a certain insect pest. If the insects feed on tissues comprising a large amount of protease inhibitor II, then indigestion is caused and the growth of the insects are inhibited. In addition, the plants protect themselves from insect pests by attracting a natural enemy etc. For wounds, plants have various activities including concentrating substances for the recovery from the wounds by inhibiting photosynthesis other than that for required for defense, and facilitating cell division for regeneration after the cut. Moreover, it is found that responses against the wound vary depending on factors such as the extent of the growth, the extent of the wound, the extent of the optical intensity and the like.

In this way, the injured plant generates various responses, however, it has been revealed that most of the injured plants cause physiological response by inducing expression of various genes. Of the responses, it is known that jasmonic acid (JA) is involved in the signaling system in a wound-induced response. JA treatment induces the expressions of many wound-induced responsive gene, and thus it is believed that JA is a signal transmitter of the wound-induced response (Creelman, R. A. et al. Plant Cell 9:1211-1223, 1997). JA is synthesized via oxidation of linolenic acid released from a membrane by lipoxigenase and the like, which is a result of the wounds. In animals, prostaglandin and arachidonic acid metabolites such as leukotrienes which are involved in inflammatory responses are similar to JA and the related substances in structure, and are synthesized from arachidonic acid released from the membrane by phospholipase $A_2$. In plants as well, it is suggested that phospholipase $A_2$ is therefore involved in a liberation of linolenic acid.

Phosphatidic acid, a membrane phospholipid, is liberated from the membrane by wounds and the expression of the wound-induced genes are induced. It is believed that this liberation results from the hydrolysis of phospholipids, which are membrane components, by phspholipase D (which is moved from the cytoplasm to the membrane by elevated-intracellular $Ca^{2+}$).

When the cell walls are injured, pectin which is a major component of the middle lamella in the cell wall is degraded, and oligogalacturonic acid is generated. It is known that the pectin degrading enzyme is also induced by the wounded state.

It is known that MAP kinases, which are some of the serine/threonine type protein kinase is activated by the wounded state. This activation is found to be induced by phosphorylation. Among MAP kinases activated by wounds, two kinase a are known: WIPK (wound-induced protein kinase) which is activated at the transcription level and SIPK (salicylic acid-induced protein kinase) which is not controlled by transcription. WIPK of tobacco is also known as a regulator of JA synthesis (Seo, S. et al., Science, 270, 1988-1992, 1995). In the inflammatory response of animals, it is known that MAP kinase is involved in the activation of cytoplasmic phospholipase $A_2$ ($cPLA_2$) and thus it is believed that WIPK controls JA synthesis by activation of $cPLA_2$.

Ethylene and abscisic acid (ABA), both of which are phytohormones, are believed to be signaling agents in the wound-induced response since production of these phytohormones is enhanced in the wounded state and treatments of plants with these phytohormones induces the expression of wound responsive genes. It is reported that ethylene cooperates with JA and upstream of JA signaling and ABA acts upstream of JA signaling (Dong, X: Curr. Opin. Plant Biol. 1:316-322, 1998; Pelia-Cortes, H. et al. Proc. Natl. Acad. Sci. USA, 92:3106-3114, 1995). Furthermore, ethylene has an effect of accelerating the maturation of fruits and is thus considered a maturation hormone. Also, it is also known that ethylene suppresses extension growth in stems, roots and the like, and aestivation formation, while it accelerates the auxetic growth of stems and roots, the formation of root hair, the growth of stems in a certain species, germination in certain species, epinasty, and the like. JA is also suggested to be involved in the ubiquitin-proteasome system which has various cell control functions.

Wound-induced response is characterized by a systemic response. For example, upon injuring leaves, it is found that plants induces such an wound-induced response in not only injured leaves, but also in non-injured leaves. It is thought that in tomatoes the protein systemin participates in this systemic wound-induced response. Systemin is excised from its precursor prosystemin in response to the wounds, to deliver to the entire plant body through seive tubes and induce JA synthesis.

JA is also suggested to be involved in hypersensitive reaction; HR). Hypersensitive reaction refers to a reaction in which the infected cells in the plant positively die, thereby confining the pathogen, inhibiting further pathogen growth and transition to the entire plant body, and resulting in spot formation. The hypersensitive reaction is believed to be a kind of disease resistance reaction. As a result of the hypersensitive reaction, the production of not only salicylic acid (SA), but also JA and ethylene is increased. Therefore, hypersensitive cell death means wound stress. By the hypersensitive response, pathogenesis-related proteins are induced. The pathogenesis-related proteins are grouped into acidic pathogen-related proteins and basic pathogenesis-related proteins according to their isoelectric points, the former are mainly induced by salicylic acid and the latter are mainly induced by JA. The acidic pathogenesis-related proteins are poorly induced by physical stimulation such as cutting and friction.

It is well known that prostaglandin synthesis is involved in inflammatory responses in animals and is inhibited by salicylic acid or acetyl derivatives thereof, acetyl salicylic acid (also known as aspirin). Also in plants, JA and SA inhibit each others syntheses and functions (Niki et al. (1998) Plant Cell Physiol. 39:500-507). The fact that SA and JA, both of which exhibit antagonitic actions, are generated by the hypersensitive reaction suggests that these two substances finely regulate signaling in wound-induced responses.

In this way, it is anticipated that JA and SA are known to be related to the signaling of stresses such as various wounds and that regulation of the activity of JA and SA can regulate a resistance to stresses such as wounds.

A number of wound responsive genes have been isolated. The expression of these genes is mainly regulated at the transcription level. These genes include synthetases, metabolic enzymes, control proteins, defense proteins and the like.

The mechanisms from injury to expression of the wound responsive genes is considerably different among the genes. For example, for the WIPK gene and the gene encoding 1-aminocyclopropane-t-carboxylic acid (ACC) synthetase which is involved in ethylene synthesis, the accumulation of transcription products thereof are observed in several minutes to about quarter of an hour after the wound. On the other hand, the accumulation of the transcription products of the genes for protein inhibitor II and basic pathogenesis-related protein become predominant several hours after the wound. The accumulation of JA, ethylene and ABA occur within a few or several tens of minutes after the wound. As such, it is suggested that other factors may be related to the induction of the expression in WIPK gene an the like. Further, in the induction of the expression of WIPK gene and the like, other pathways are also predicted, in addition to the pathway via JA.

Therefore, the identification of factors responsible for the regulation of WIPK and SIPK may effectively impart regulation of wound-induced responses in organisms such as plants, thus imparting stress resistance. However, heretofore, such factors have not been identified. Therefore, it is desired to seek such factors in the art.

THE PROBLEMS TO BE SOLVED BY THE INVENTIONS

The purpose of the present invention is to impart stress (such as wound) resistance to organisms such as plants, and animals by isolating and synthesizing the factors involved in WIPK and/or SIPK.

SUMMARY OF THE INVENTION

The above-discussed purpose will be accomplished by isolating or synthesizing a Labdan-type diterpenoid compound having the following structure:

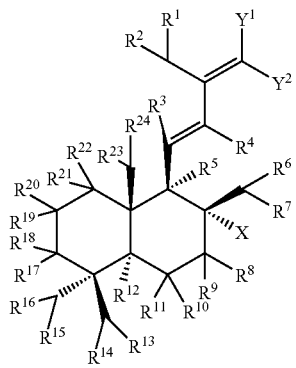

(Chemical formula I)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

In addition to those described above, the present invention provides the following.

1. A compound having the following structure:

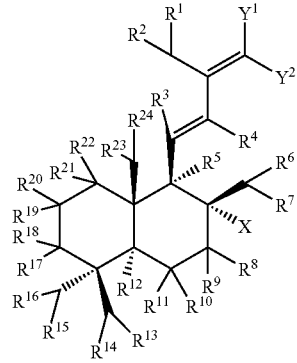

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

2. The compound of item 1, wherein one of $Y^1$ and $Y^2$ is hydrogen, the other is a methylol, substituted methylol, C1-aldehyde, C1-carboxyl, or substituted C1-carboxyl group.

3. The compound of item 1, wherein all of $R^1$-$R^{24}$ are hydrogen.

4. The compound of claim 1, wherein X is hydroxy.

5. The compound of item 1, having the following structural formula:

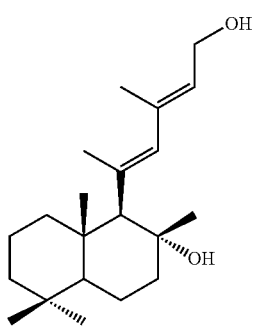

(WAF-1)

6. A composition, comprising a compound having the following structure:

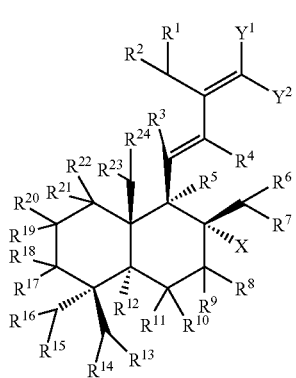

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

7. A composition for imparting stress resistance to a plant or augmenting said stress resistance, comprising a compound having the following structure:

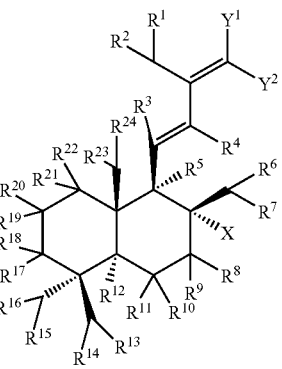

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

8. The composition of item 7, wherein said stress resistance is at least one resistance selected from the group consisting of wound resistance, insect resistance, disease resistance, and hypersensitivity cell death resistance.

9. The composition of item 7, wherein the imparting or augmenting of said stress resistance is accomplished by controlling the activity of at least one protein selected from the group consisting of wound-induced protein kinases, salicylic acid-induced protein kinases, pathogenesis-related proteins, and 1-amino-cyclopropane-t-carboxylic acid synthetases.

10. The composition of item 7, wherein the imparting or augmenting of said stress resistance is accomplished by controlling at least one signaling system selected from the group consisting of jasmonic acid signaling systems and salicylic acid signaling systems.

11. A method of imparting stress resistance to a plant or augmenting said stress resistance, wherein said method comprises the following steps:

a) applying to said plant a compound having the following structure:

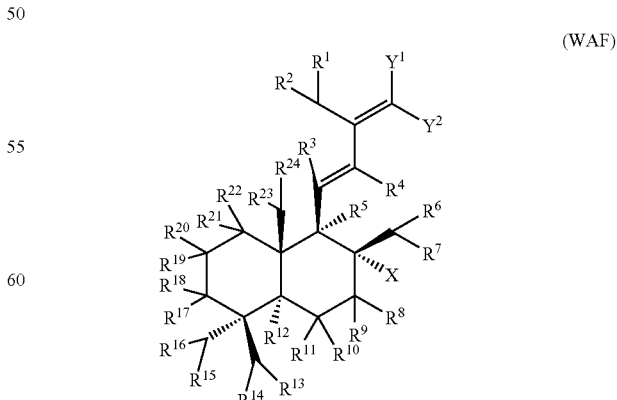

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy,. aldehyde, carboxyl, or substituted carboxyl; and $R^1$-$R^{24}$ are independently selected from the group of hydrogen, alkyl, and substituted alkyl.

12. The method of item 11, wherein said stress resistance is at least one resistance selected from the group consisting of wound resistance, insect resistance, disease resistance, and hypersensitivity cell death resistance.

13. The method of item 11, wherein the imparting or augmenting of said stress resistance is accomplished by controlling the activity of at least one protein selected from the group consisting of wound-induced protein kinases, salicylic acid-induced protein kinases, pathogenesis-related proteins, and 1-amino-cyclopropane-t-carboxylic acid synthetases.

14. The method of item 11, wherein the imparting or augmenting of said stress resistance is accomplished by controlling at least one signaling system selected from the group consisting of jasmonic acid signaling systems and salicylic acid signaling systems.

15. A method of producing stress resistant plants, comprising:

a) applying to said plant a compound having the following structure:

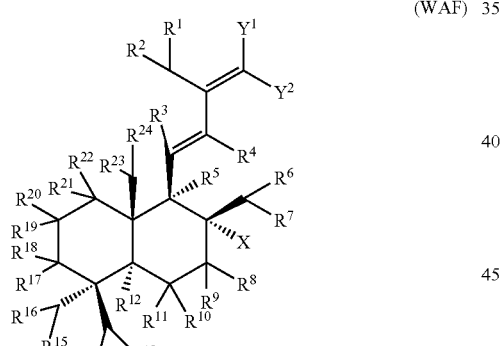
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

16. A plant, obtained by the method of item 15.

17. A method of producing stress resistant plant tissues, comprising:

a) applying to said plant tissue a compound having the following structure:

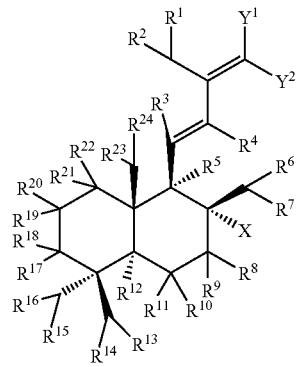
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

18. A plant tissue, obtained by the method of item 17.

19. A method of producing stress resistant plant cells, comprising:

a) applying to said plant cell a compound having the following structure:

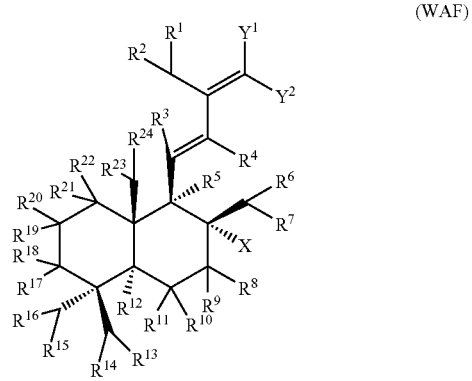
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

20. A plant cell, obtained by the method of item 19.

21. A method of producing stress resistant plant seeds, comprising:

a) applying to said plant seed a compound having the following structure:

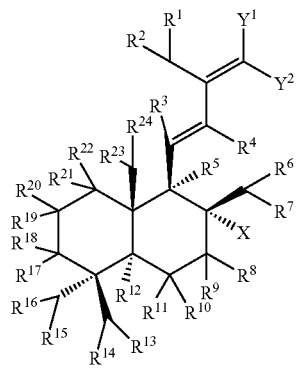

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

22. A plant seed, obtained by the method of item 21.

23. A method of synthesizing a compound having the following structure:

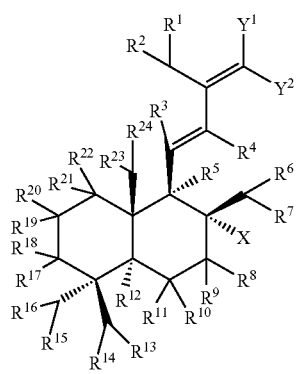

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl, said method comprises the following steps:

a) reacting a compound (an intermediate 1) having

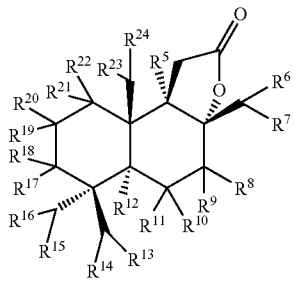

wherein, in the formula:

$R^5$-$R^{24}$ are independently selected from the group consisting of hydrogen, alkyl, and substituted alkyl, and the same as $R^1$-$R^{24}$ for WAF, with alkyl lithium to provide an intermediate 2;

(the intermediate 2)

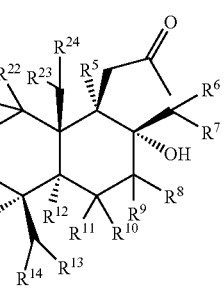

b) mixing and reacting the product obtained in a) with m-chloroperbenzoic acid and then with a 10% potassium hydroxide in methanol to provide an intermediate 4;

(the intermediate 4)

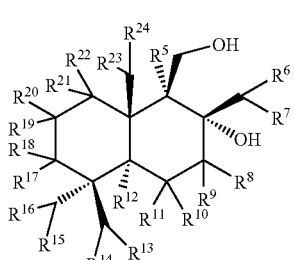

c) reacting the product obtained in b) with N-methylmorphorine N-oxide in the presence of tetrapropyl ammonium peruthenate to provide an intermediate 5;

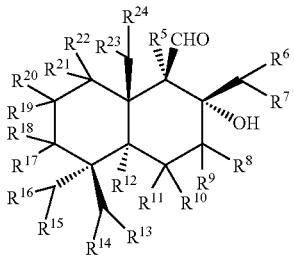

(the intermediate 5)

d) adding a compound

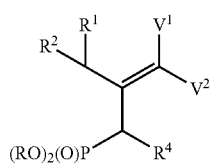

wherein, one of $V^1$ and $V^2$ is hydrogen or alkyl, and the other is Z-V, and wherein Z is (CH2)n-C(=O)—O—, V is alkyl, n is an integer of 0 or more, and R is alkyl, to said intermediate 5 obtained in the step c) in an organic solvent in the presence of $NaNH_2$ to provide an intermediate (6):

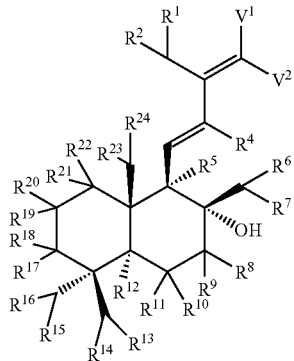

e) adding diisobutyl aluminum hydride in an organic solvent to said intermediate (6) obtained in the step d) to provide

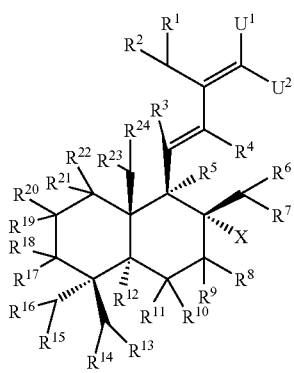

wherein, X is selected from the group consisting of hydroxy, substituted hydroxy, halogen, thiol, and substituted thiol;

one of $U^1$ and $U^2$ is hydrogen or alkyl, and the other is Z-U, wherein Z is a single bond, or a divalent group having alkane or substituted alkane having two hydrogen atoms removed, and U is hydroxy; and $R^1$-$R^{24}$ are independently selected from the group of hydrogen, alkyl, and substituted alkyl; and optionally a further oxidation or substitution step where $Y^1$ is other than hydroxy.

24. The method of item 23, wherein said X is hydroxy;

one of said $Y^1$ and $Y^2$ is hydrogen, and the other is methylol;

all of $R^1$-$R^{24}$ are hydrogen;

said organic solvent is THF;

the alkyl lithium in said step a) is methyl lithium;

one of $U^1$ and $U^2$ is hydrogen, and the other is Z-U, wherein Z is —$CH_2$—, and U is hydroxy; and one of said $V^1$ and $V^2$ is hydrogen, and the other is —C(=O)—O—$CH_2CH_3$.

25. A method of quantifying a compound having the following structure:

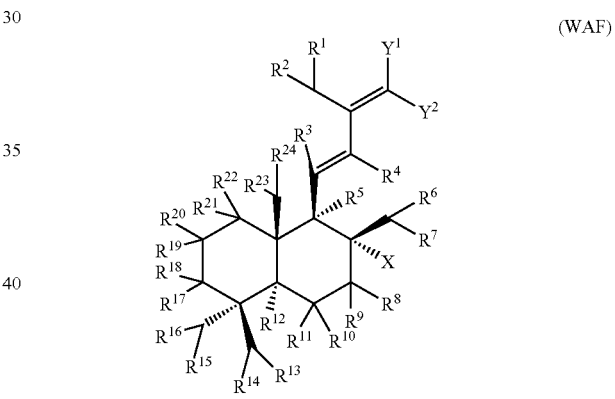

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl, said method comprises the following steps:

1) providing a sample;

2) adding the predetermined amount of the steric isomer of said compound to said sample;

3) separating said sample by a reverse phase column chromatography; and 4) calculating the amount of said compound from said separated steric isomer.

26. The method of item 25, wherein said compound has the following structural formula:

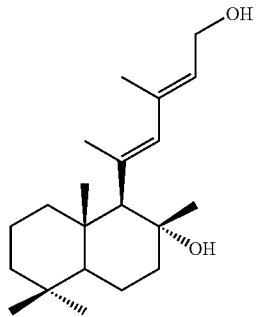
(WAF-1)

said steric isomer has the following structural formula:

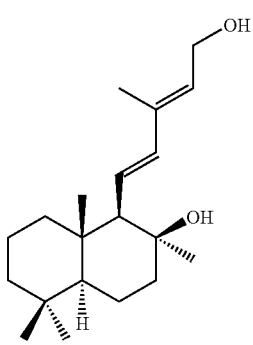
(Labdan a)

27. The method of item 25, wherein said sample is extracted with methanol and subsequently with methyl acetate, prior to the separation with said reverse column chromatography.

28. The method of item 25, wherein the separation with said reverse column chromatography comprises a separation with a C18 reverse column chromatography, and said separation comprises a first separation in 80%:20% (v/v) methanol:water, and a separation with 9:8 (v/v) acetonitrile:water.

29. The method of item 25, wherein said calculation comprises the correction of the recovery loss.

30. A composition for inducing a rapid accumulation of a WRKY family gene in a plant under a condition requiring the accumulation of a WRKY family gene, said composition comprises a compound having the following structure:

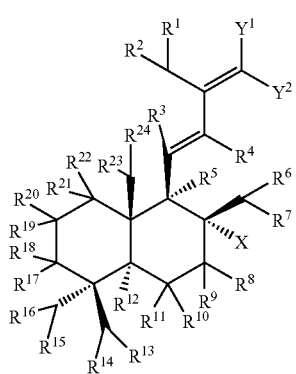
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

31. The composition of item 30, wherein said compound has the following structural formula:

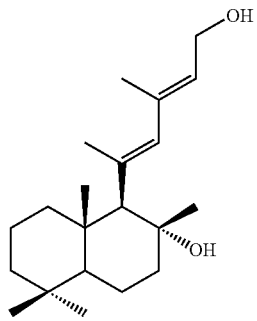
(WAF-1)

32. The composition of item 30, wherein the condition requiring the accumulation of said WRKY family gene is a condition requiring the rapid response to stress.

33. The composition of item 30, wherein said plant is provided with a wound resistance, insect resistance, disease resistance, and hypersensitivity cell death resistance by inducing a rapid accumulation of said WRKY family gene.

34. The composition of item 30, wherein said WRKY family gene is WIZZ or TIZZ.

35. A composition for regulating the expression of a WRKY family gene, comprising a compound having the following structure:

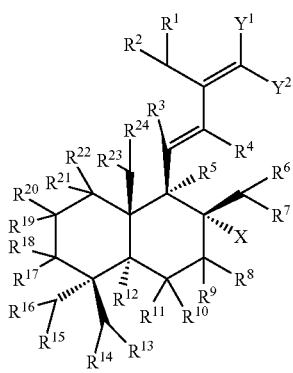
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and R$^1$-R$^{24}$ are independently selected from the group of hydrogen, alkyl, and substituted alkyl.

36. A method of inducing a rapid accumulation of a WRKY family gene in a plant under a condition requiring the accumulation of a WRKY family gene, wherein said method comprises the following steps:

a) applying to said plant a compound having the following structure:

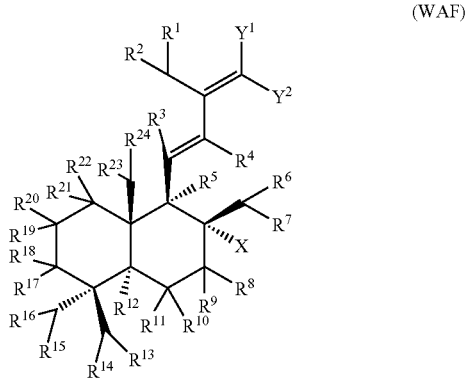

(WAF)

wherein, in the formula:

X is selected from the group consisting of hydroxy, substituted hydroxy, halogen, thiol, and substituted thiol;

one of Y$^1$ and Y$^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and R$^1$-R$^{24}$ are independently selected from the group of hydrogen, alkyl, and substituted alkyl.

37. The method of item 36, wherein said compound has the following structural formula:

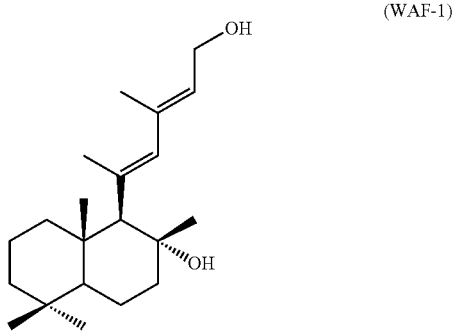

(WAF-1)

38. The method of item 36, wherein the condition requiring the accumulation of said WRKY family gene is a condition requiring the rapid response to stress.

39. The method of item 36, wherein said plant is provided with a wound resistance, insect resistance, disease resistance, and hypersensitivity cell death resistance by inducing a rapid accumulation of said WRKY family gene.

40. The method of item 36, wherein said WRKY family gene is WIZZ or TIZZ.

41. The method of item 36, wherein said compound is applied immediately after the accumulation of said WRKY family gene is required.

42. A composition for regulating the expression of a WRKY family gene, comprising the compound of item 1.

43. A use of a compound for imparting stress resistance to a plant or augmenting said stress resistance, said compound having the following structure:

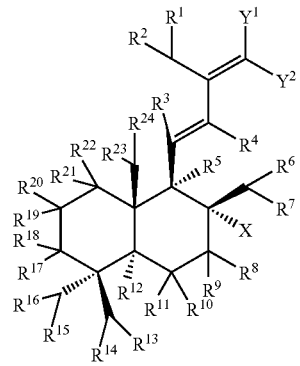

wherein, in the formula:

X is selected from the group consisting of hydroxy, substituted hydroxy, halogen, thiol, and substituted thiol;

one of Y$^1$ and Y$^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and R$^1$-R$^{24}$ are independently selected from the group of hydrogen, alkyl, and substituted alkyl.

44. A use of a compound for producing stress resistant plants, said compound having the following structure:

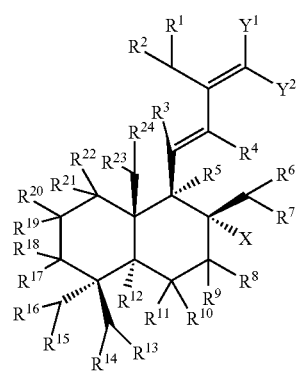

wherein, in the formula:

X is selected from the group consisting of hydroxy, substituted hydroxy, halogen, thiol, and substituted thiol;

one of Y$^1$ and Y$^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and R$^1$-R$^{24}$ are independently selected from the group of hydrogen, alkyl, and substituted alkyl.

45. A use of a compound for producing stress resistant plant tissues, said compound having the following structure:

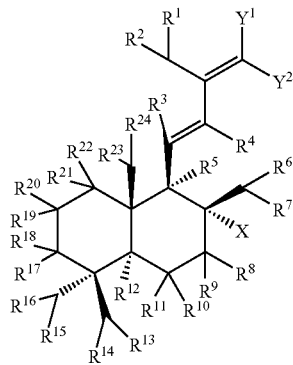

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

46. A use of a compound for producing stress resistant plant cells, said compound having the following structure:

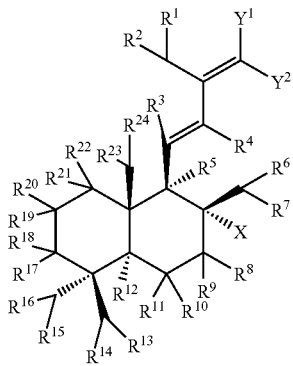

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

48. A use of a compound for inducing a rapid accumulation of a WRKY family gene in a plant requiring the accumulation of said WRKY family gene, said compound having the following structure:

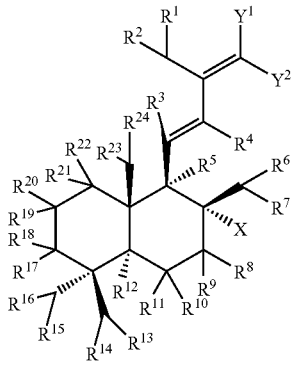

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

47. A use of a compound for producing stress resistant plant seeds, said compound having the following structure:

49. A use of a compound for regulating the expression of a WRKY family gene, said compound having the following structure:

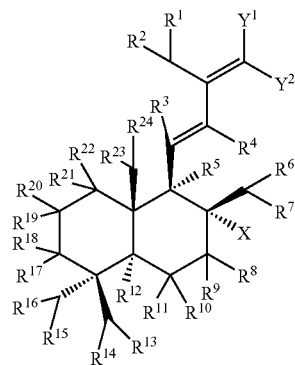

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

50. A composition for facilitating the elongating growth or auxetic growth of a plant, inhibiting the elongating growth of a plant, facilitating the maturation of a plant, or regulating the flowering of a plant, said composition comprises a compound having the following structure:

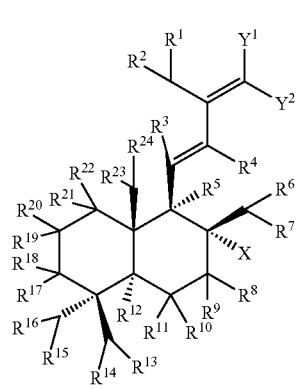

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

51. A method of facilitating the elongating growth or auxetic growth of a plant, inhibiting the elongating growth of a plant, facilitating the maturation of a plant, or regulating the flowering of a plant, said method comprises applying to a plant a compound having the following structure:

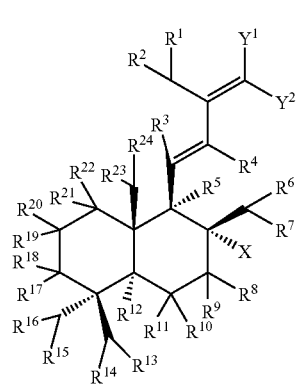

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

52. A plant, obtained by the method of item 51.

53. A use of a compound for facilitating the elongating growth or auxetic growth of a plant, inhibiting the elongating growth of a plant, facilitating the maturation of a plant, or controlling the flowering of a plant, said method comprises applying to a plant a compound having the following structure:

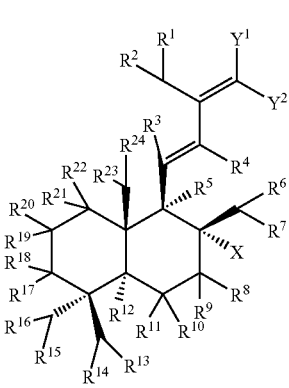

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

BRIEF DESCRIPTION OF THE DRAWINGS

In FIG. 2.

In FIG. 8.

In FIG. 12, FIG. 12A shows the effect on the defense of tobacco leaves against TMV infection shown as size of necrosis spots, when the compound of the invention at 10 pM to 100 nM concentrations or water was given to the leaves. FIG. 12B shows pictures which exhibit the defense of tobacco leaves against TMV infection when the compound of the invention at 100 nM concentrations or water was given to the leaves. FIG. 12C shows the comparison of amounts of TMV coat protein when the compound of the invention at 100 pM or 100 nM, or water was given to the tobacco leaves.

PREFERRED EMBODIMENTS OF THE INVENTION

Figure 1:
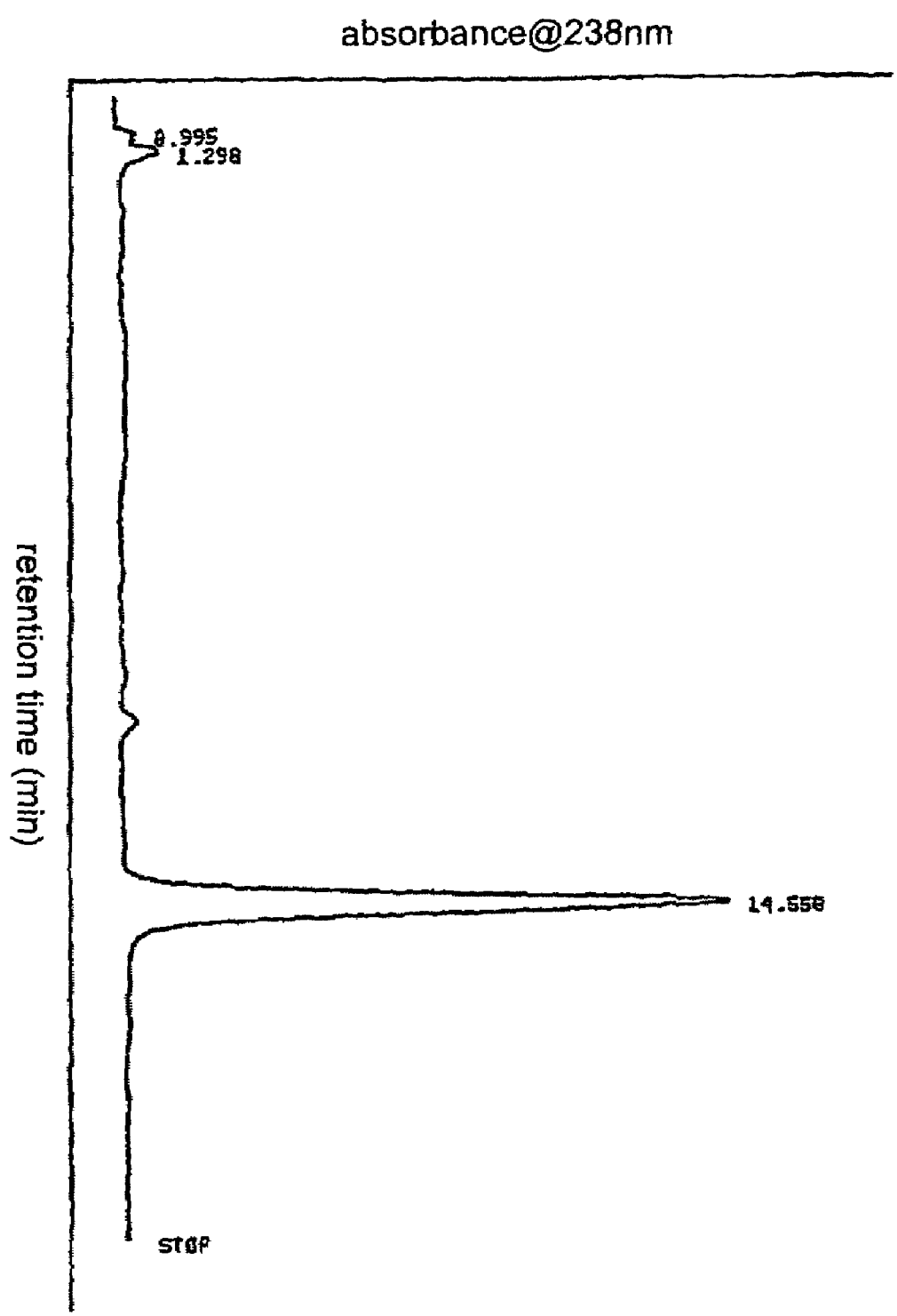
FIG. 1 shows a chromatogram upon isolating the compound of the invention.

The following illustrates the present invention. It should be understood that the singular forms include plural forms throughout the specification unless otherwise indicated. Thus, it should be understood that a singular article (for example "a," "an", "the" and the like for English, "ein", "der", "das", "die" and the like, and their declined forms for German, "un", "une", "le", "la" and the like for French, "un", "una", "el", "la" and the like for Spanish, and corresponding articles and adjectives for other languages) include their plural forms unless otherwise indicated. It should be understood that the terms as used herein refer to those meanings commonly used in the art unless otherwise indicated.

(Terms)

Definitions of the terms as specifically used herein are listed below.

As used herein, the term "organism" is used in the broadest meaning in the art and refers to objects which maintain a living state, which typically have various characteristics such as cellular structure, growth (self-proliferation), growth, regulation, metabolism, repairing ability, and the like, as basic properties, normally have inheritance that nucleic acids control and proliferation involved in metabolism that proteins control. Organisms include prokaryotes, eukaryotes (such as plants, animals) and the like.

As used herein, the term "plant(s)" is a general name of organisms belonging to Plantae and characterized by immotile organisms which have chlorophyl, hard cell walls, and presence of abundant continuous embryonic tissue. Typically, plants refers to flowering plants having cell walls, and anabolism by chlorophyll. "Plants" include any of the monocotyledons and the dicotyledons. Preferred plants include monocotyledons belonging to Gramineae such as wheat, maize, rice, barley, and sorghum. Other examples of preferred plants include tobacco, piment, eggplant, melon, tomato, sweat potato, cabbage, cibol, broccoli, carrot, cucumber, citrus, celery cabbage, lettuce, peach, potato, and apple. In addition to crop plants, preferred plants include, but are not limited to, flowering plants, trees, grasses, weeds and the like. Unless indicated otherwise, plants mean any of the plants bodies, the plant's organs, the plant's tissues, plant's cells, and the plant's seeds. Example of plant's organs includes roots, leaves, stems, and flowers. Example of the plant's cells includes callus and cells in suspension culture.

In other embodiments, examples of plant species which maybe used in the invention includes plants of *Solanaceae, Gramineae, Cruciferae, Rosaceae, Leguminosae, Cucurbitaceae, Labiatae, Liliaceae, Chenopodiaceae, Umbelliferae.*

Examples of *Solanaceae* include plants belonging to *Nicotiana, Solanum, Datura, Lycopersion,* or *Petunia* (including e.g., tobacco, aubergines (eggplant), potatoes, tomatoes, capsicums, petunias and the like).

Examples of *Gramineae* include plants belonging to *Oryza, Hordenum, Secale, Scccharum, Echinochloa,* or *Zea* (including e.g., rice, barley, rye, cockspur, sorghum, maize and the like.

Examples of *Cruciferae* include plants belonging to *Raphanus, Brassica, Arabidopsis, Wasabia,* or *Capsella* (including e.g., Chinese radish, mustard, thalecress, Japanese horse radish, shepherds's purse and the like.

Example of *Rosaceae* includes plants belonging to *Orunus, Malus, Pynus, Fragaria,* or *Rosa* (including e.g., Japanese apricots, peaches, apples, pears, strawberries, roses and the like).

Examples of *Leguminosae* include plants belonging to *Glycine, Vigna, Phaseolus, Pisum, Vicia, Arachis, Trifolium, Alphalfa,* or *Medicago* (including e.g., soy beans, azuki beans, kidney beans, peas, broad beans, peanuts, clovers, bur clovers and the like).

Examples of *Cucurbitaceae* include plants belonging to *Luffa, Cucurbita*, or *Cucumis* (including e.g., dishcloth gourds, pumpkins, cucumbers, melons and the like).

Examples of *Labiatae* include plants belonging to *Lavandula, Mentha*, or *Perilla* (including e.g., lavenders, mints, beefsteak plants and the like).

Examples of *Liliaceae* include plants belonging to *Allium, Lilium*, or *Tulipa* (including e.g., cibols, garlics, lilies, tulips and the like).

Example of *Chenopodiaceae* includes plants belonging to *Spinacia* (including e.g., spinach).

Examples of *Umbelliferae* includes plants belonging to *Angelica, Daucus, Cryptotaenia*, or *Apitum* (including e.g., archangels, carrots, Japanese hornworts, celeries and the like).

The plants used in the present method are preferably tobaccos, tomatoes, potatoes, rices, maizes, Chinese radishs, soy beans, peas, bur clovers, and spinaches, more preferably, tobaccos, tomatoes, potatoes, maizes, and soybeans.

The present agent may be useful for imparting stress resistance to various organisms including animals as well as plants. As used herein, the term "Animal(s)" are used in the broadest meaning in the art, including vertebrate and invertebrate. Animals includes, but is not limited to, Mammalia, Aves, Reptilia, Amphibia, Pisciformes, Insecta, Vermes and the like. Therefore, organisms and animals in the specification include every organism that may be stressed.

As used herein, the term "stress" refers to factors which may physically, chemically, or biologically impart stress to an organism such as a plant, and/or prevent normal growth/proliferation of the organism. Stress includes physical stress (such as the result of light, heat, cooling, freezing, ultraviolet radiation, X-rays, cutting, friction), chemical stress (such as the result of the oxygen stress, chemical substances, bioactive substance)) biological stress (such as the result of viruses, pathogens (including e.g., infection with a pathogen which causes rice blast in plants), for example. Characteristics for the expression of genes including genes involved in stress may be determined by extracting RNA from any part of an organism such as a plant to analyze amounts of the expression by Northern blot analysis or quantitate expressed proteins by Western blot analysis.

Therefore, as used herein, the term "stress resistance" refers to delaying, stopping, or recovering a reaction which normally weakend organisms such as plants, or otherwise not generating the reaction which would weaken otherwise the organisms. Thus, the organisms to which stress resistance is imparted have an elevated survival ratio compared to organisms to which stress resistance not imparted. As used herein, "impart stress resistance" refers to maintaining the organisms (wherein the organisms are treated) in the living state, whereas wild-type organisms would otherwise completely or almost completely die when some stress is imparted. Such survival can be examined using techniques well known in the art. For example, survival can be examined with the naked eye or via microscope. As used herein, "augment stress resistance" refers to increasing a resistance to a stress in treated organisms whereas the wild-type organisms show some extent of resistance upon receiving the stress. Since imparting and augmenting stress resistance sometimes may have meanings that overlap one another, these terms may be used interchangeably herein.

As used herein, the term "wound resistance" refers to a property of organisms such as plants and the ability to reduce the extent of a wound. As used herein, the term "disease resistance" refers to a property of organisms such as plants and the ability to reduce an extent of disease development. As used herein, the term "insect resistance" refers to a property of organisms such as plants and the ability to reduce harm upon being fed upon. Therefore, "stress resistance" as used herein encompasses "wound resistance", "insect resistance", and "disease resistance".

It is contemplated that agents, compounds, compositions and methods of the invention function in not only monocotyledons, but also dicotyledons and other organisms including animals. This is explained by the basic mechanisms of stress responsive regulation being similar between monocotyledons and dicotyledons and the inflammatory responses in animals have similar mechanisms (arachidonic acid metabolic pathway) as well.

As used herein, the term "elongating growth" refers to apical growth, intercalary growth and the like. "Apical growth" is conducted at a growing point in apical stems or apical roots and refers to the formation of axial organs such as stems and roots. "Intercalary growth" refers to that when enlongating, the growth does not occur equally in each part, but occurs in growth region between grown parts (e.g., organs or tissues, in which growth has been stopped) to some extent and also refers to internodal growth.

As used herein, the term "auxetic growth" refers to growth within the volume of the plant body, plant tissue or plant cell which increases mass. In the plant tissues or organs, auxetic growth also generates an increased number of plant cells.

As used herein, "maturation" refers to a process from the time of germ cell maturation in the plant body or plant tissue or the completion of the growth period of the fruit body to complete maturation.

As used herein, "regulating flowering" refers to changing a time period from an aestivation formation to an actual flowering.

Herein, cultivation of plants can be carried out by any of the methods known in the art. Cultivating methods of plants are exemplified in for example, "Experimental protocols in model plants-rice/*Arabidopsis*-": Saibo-kogaku Bessatu series (Cellular Engineering Supplemental); "Ine-no-saibai-ho (Cultivation method for rice)" (Kazutoshi Okuno) pp. 28-32, and "*Arabidopsis*-no-baiyou-ho (Cultivation method for *Arabidopsis*)" (Yasuo Niwa) pp. 33-40(Eds. Ko Shimamoto, Kiyotaka Okada) and thus those skilled in the art can easily carry out the methods and it is not necessary to describe such method herein in detail. For example, cultivation of *Arabidopsis* can be performed by any of the method of geoponics, rock wool cultivation, and hydroponics. If it is cultivated under continuous light condition using a white fluorescent lamp (about 6000 lux), *Arabidopsis* begins to bloom 4 weeks after seeding and produces mature seeds 16 days after flowering. 40 to 50 seeds per pod are obtained and 10000 seeds are obtained in 2 to 3 months before death. The dormancy period of the seed is short, after drying the seeds for about 1 week, matured seeds germinate in 2 to 3 days after absorbing water. If the seeds are treated at a low temperature of 4° C. after absorbing water and seeding, germination is synchronized. Cultivation of rice is conducted in geoponics, grown under a light condition of 10000 lux or more. Transferring the conditions to short day condition, results in heading induced about 40 days after seeding, the plants bloom 30 days after heading and matured seeds are obtained about 40 days after flowering.

For culturing, differentiating and regenerating plant cells, the procedures and media known in the art are used. Such media include, but are not limited to Murashige-Skoog (MS) medium, GaMborg B5 (B) medium, White medium, Nitsch & Nitsch (Nitsch) medium and the like. These media are normally used with the addition of a suitable amount of plant growth regulation substances (phytohormones) and the like. Preferably, the agent of the invention is used as an additive in the media and may serve as a regulator or growth (proliferation), differentiation and regeneration of plant body, plant tissue or organ, or plant cells. Also, the agent of the invention is not only comprised as an additive for the media, but also comprised in various forms (e.g., agricultural compositions such as a solid fertilizer, a liquid nutrition agent and the like) as described below.

Analysis of the expression regulation in WIPK- or SIPK-associated genes and the like can be conducted by gene analysis method using DNA arrays. DNA arrays are generally reviewed in Saibo-kogaku Bessatu (Cellular Engineering Supplemental) "DNA microarray-to-saisin PCR-ho (DNA microarray and Current PCR method)", Ed., Shujunsha Co. Ltd. Analysis of plants using DNA array has recently been conducted (Schenk P M et al., (2000) Proc. Natl. Acad. Sci. (USA) 97:11655-11660). Hereinafter, DNA arrays and genetic analysis methods using the same are briefly explained.

"DNA array" refers to a device in which DNAs are arrayed and immobilized on a plate. DNA arrays are divided into DNA macroarrays, DNA microarrays, and the like according to the size of the plate or the density of DNA placed on the plate.

The border between macro and micro is not strictly determined. However, generally, "DNA macroarray" refers to a high density filter in which DNA is spotted on a membrane, while "DNA microarray" refers to a plate of glass, silicon, and the like which carries DNA on a surface thereof. There are a cDNA arrays, oligoDNA arrays, and the like varying according to the type of DNA placed on the array.

A certain high density oligoDNA array, in which a photolithography technique for production of semiconductor integrated circuits is utilized and a plurality of oligoDNAs are simultaneously synthesized on a plate, is specifically called a "DNA chip", an adaptation of the term "semiconductor chip". Examples of the DNA chip prepared by this method include GeneChip® (Affymetrix, CA), and the like (see Marshall A et al., (1998) Nat. Biotechnol. 16:27-31 and Ramsay G et al., (1998) Nat. Biotechnol. 16 40-44. Preferably, GeneChip® may be used in genetic analysis using a microarray according to the present invention. The DNA chip is defined as described above in a narrow sense, but may refer to all types of DNA arrays or DNA microarrays.

Thus, DNA microarrays are devices in which several thousands to several ten thousands or more of gene DNAs are arrayed on a glass plate in high density. Therefore, it is made possible to analyze gene expression profiles or gene polymorphism on a genomic scale by hybridization of cDNA, cRNA or genomic DNA. With this technique, it has been made possible to analyze a signaling system and/or a transcription control pathway (Fambrough D et al., (1999), Cell 97,727-741); the mechanism of tissue repair (Iyer V R et al., (1999), Science 283:83-87); the action and mechanism of medicaments (Marton M J, (1999), Nat. Med. 4:1293-1301); fluctuations in gene expression during development and differentiation processes on a wide scale; identify a gene group whose expression fluctuates according to pathologic conditions and the like; find a novel gene involved in a signaling system or a transcription control; and the like. Further, as to gene polymorphism, it has been made possible to analyze a number of SNPs with a single DNA microarray (Cargill M et al., (1999), Nat. Genet. 22:231-238).

As a labeling method for synthesized DNA arrays, for example, double fluorescence labeling is used. In this method, two different mRNA samples are labeled by different respective fluorescent dyes. The two samples are subjected to competitive hybridization on the same microarray, and both fluorescences are measured. By comparing the fluorescences, differences in gene expression can be detected. Examples of the fluorescent dye include, but are not limited to, Cy5 and Cy3, which are most often used, and the like. The advantage of Cy3 and Cy5 is that the wavelengths of fluorescences do not overlap substantially. Double fluorescence labeling may be used to detect mutations or morphisms in addition to differences in gene expression.

In assays using a DNA array, a fluorescent signal indicating hybridization on the DNA microarray is detected by a fluorescence detector or the like. As such a detector, there are conventionally various available detectors. For example, a research group at the Stanford University has developed an original scanner which is a combination of a fluorescence microscope and a movable stage (see http://cmgm.stanford.edu/pbrown). A conventional fluorescence image analyzer for gels, such as FMBIO (Hitachi Software Engineering), Storm (Molecular Dynamics), and the like, can read a DNA microarray if the spots are not arrayed in too great a density. Examples of other available detectors include ScanArray 4000 and 5000 (GeneralScanning; scan type (confocal type)), GMS418 Array Scanner (Takara Shuzo; scan type (confocal type)) Gene Tip Scanner (Nippon Laser&Electronics Lab.; scan type (non-confocal type)), Gene Tac 2000 (Genomic Solutions; CCD camera type)), and the like.

The amount of data obtained from DNA microarrays is huge. Software for managing correspondences between clones and spots, analyzing data, and the like is important. As such software, software attached to each detection system is available (Ermolaeva O et al., (1998) Nat. Genet. 20:19-23). Further, an example of a database format is GATC (genetic analysis technology consortium) proposed by Affymetrix.

The regulation of the expression in WIPK- and SIPK-related genes as well as the down stream genes thereof by the agent, compound or composition of the invention may also be used in genetic analysis using a differential display technique.

Differential display techniques are methods for detecting or identifying genes whose expression fluctuates. In this method, cDNA is prepared from each of at least two samples, and amplified by PCR using a set of any primers. Thereafter, a plurality of generated PCR products are separated by gel electrophoresis. After the electrophoresis pattern is produced, genes with fluctuating expression are cloned based on relative signal strength change between each band.

In this way, techniques that regulate expression of the genes upstream or downstream of the signaling pathway regulated by the compound or substance of the invention are well known.

The structure of the compound according to the invention can be determined by techniques well known in the art. Such methods for determining the structure includes, but is not limited to, physical analysis methods such as NMR, X-ray structural analysis, IR analysis, mass spectrometry; chemical analysis methods such as method using specific chemical reactions with particular substituents, like the Fehling reaction; biochemical analysis using a particular enzyme, such as aldehyde dehydrogenase, which specifically reacts with a particular substitute; biological analysis using microorganisms and the like. Preferably, physical analysis methods such as NMR are used.

(Organic Chemistry)

It is to be understood that any compound as used herein includes any isomers thereof, for example, structural isomers, steric isomers which have the same structural formula, but different atomic conformations and configurations (e.g., geometric isomers, atrop isomers, optical isomers), and cis-trans isomers (such as (E,E) (E,Z), (Z,E), (Z,Z), and the like, racemate, enantiomers and the like). In one embodiment, the compound of the present invention as used herein maybe a single isomer, or a mixture of two or more isomers.

As used herein, the term, "diterpenoid" refers to a compound having a two consecutive terpenoid structures. A terpene is a generic designation that refers to an organic compound from various plants (or in rare cases, from animals) having a carbon number of a multiple of five (5n; n≧2) and biosynthetically derived from precursors having n isoprene or isopentane units. A terpene is also designated as a terpenoid. Various terpene-type hydrocarbons such as alcohols, ketones, aldehydes, carboxylic acids, lactones, and the like are known in the art. Terpenes are classified as follows according to their carbon numbers. Among these, those having n=4 are designated as diterpenes (having a carbon number of 20).

As used herein, the term, "Labdan-type" refers to a compound having the following (labdan) structure:

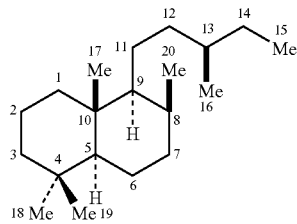

The Labdan-type compound of the present invention may have any substituent. The substituents include any substituents selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic groups, substituted carbocyclic groups, heterocyclic groups, substituted heterocyclic groups, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl, but those substituents which do not affect the hydrophilicity, polarity, and the like are preferable. Such substituents include those substituents selected from the group consisting of hydrogen, alkyl, and substituted alkyl. Preferably, the alkyl may be C1-C6 alkyl, more preferably C1-C5 alkyl, C1-C4 alkyl, C1-C3 alkyl, C1-C2 alkyl, methyl, and the like. When the substituted alkyl is selected as the substituent, preferably, the substituted portion may a substituent which does not affect the hydrophilicity, polarity, and the like.

Also, the substituent may be a substituent selected from the group consisting of halogen, alkoxy, substituted alkoxy, amino, substituted amino, alkylthio, substituted alkylthio, arylthio, substituted arylthio, nitro, carboxy, substituted carboxy, acyl, substituted acyl, and substituted sulfonyl, so long as it does not affect the essential function of the present invention.

As used herein, the term, "alkyl" refers to a monovalent group having one hydrogen atom removed from an aliphatic hydrocarbon (alkane) such as methane, ethane, propane, and the like, and is generally represented by $C_nH_{2n+1}$— (wherein n is a positive integer). The alkyl may be straight chain or branched. The term, "substituted alkyl" refers to an alkyl having its H substituted with the following substituent. Specific examples of these may include C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, C1-C11 alkyl, or C1-C12 alkyl, C1-C2 substituted alkyl, C1-C3 substituted alkyl, C1-C4 substituted alkyl, C1-C5 substituted alkyl, C1-C6 substituted alkyl, C1-C7 substituted alkyl, C1-C8 substituted alkyl, C1-C9 substituted alkyl, C1-C10 substituted alkyl, C1-C11 substituted alkyl, or C1-C12 substituted alkyl. For example, C1-C10 alkyl refers to a straight chain or branched alkyl having 1-10 carbon atoms, and is represented by methyl ($CH_3$—), ethyl ($C_2H_5$—), n-propyl ($CH_3CH_2CH_2$—), isopropyl (($CH_3)_2CH$—) n-butyl ($CH_3CH_2CH_2CH_2$—), n-pentyl ($CH_3CH_2CH_2CH_2CH_2$—), n-hexyl ($CH_3CH_2CH_2CH_2CH_2CH_2$—), n-heptyl ($CH_3CH_2CH_2CH_2CH_2CH_2CH_2$—), n-octyl ($CH_3CH_2CH_2CH_2CH_2CH_2CH_2CH_2$—), n-nonyl ($CH_3CH_2CH_2CH_2CH_2CH_2CH_2CH_2CH_2$—), n-decyl ($CH_3CH_2CH_2CH_2CH_2CH_2CH_2CH_2CH_2CH_2$—), —$C(CH_3)_2$ $CH_2CH_2CH(CH_3)_2$, —$CH_2CH(CH_3)_2$, and the like. Also, for example, the C1-C10 substituted alkyl refers to a C1-C10 alkyl having its one or more hydrogen atoms substituted with a substituent.

As used herein, the term, "alkane" refers to an aliphatic hydrocarbon represented by the general formula $C_nH_{2n+2}$. The alkanes include methane, ethane, propane, and the like. The alkane may be straight chain or branched. The term, "substituted alkane" refers to an alkane having its H substituted with the following substituent. Specific examples of these may include C1-C2 alkane, C1-C3 alkane, C1-C4 alkane, C1-C5 alkane, C1-C6 alkane, C1-C7 alkane, C1-C8 alkane, C1-C9 alkane, C1-C10 alkane, C1-C11 alkane, or C1-C12 alkane, C1-C2 substituted alkane, C1-C3 substituted alkane, C1-C4 substituted alkane, C1-C5 substituted alkane, C1-C6 substituted alkane, C1-C7 substituted alkane, C1-C8 substituted alkane, C1-C9 substituted alkane, C1-C10 substituted alkane, C1-C11 substituted alkane, or C1-C12 substituted alkane. For example, C1-C10 alkane refers to a straight chain or branched alkane having 1-10 carbon atoms, and is represented by methane ($CH_4$), ethane ($C_2H_6$), n-propane ($CH_3CH_2CH_3$), isopropane (($CH_3)_2CH_2$), n-butane ($CH_3CH_2CH_2CH_3$), n-pentane ($CH_3CH_2CH_2CH_2CH_3$), n-hexane ($CH_3CH_2CH_2CH_2CH_2CH_3$), n-heptane ($CH_3CH_2CH_2CH_2CH_2CH_2CH_3$), n-octane ($CH_3CH_2CH_2CH_2CH_2CH_2CH_2CH_3$), n-nonane ($CH_3CH_2CH_2CH_2CH_2CH_2CH_2CH_2CH_3$), n-decane ($CH_3CH_2CH_2CH_2CH_2CH_2CH_2CH_2CH_2CH_3$), $CH(CH_3)_2$ $CH_2CH_2CH_2CH(CH_3)_2$, $CH_3CH(CH_3)_2$, and the like. Also, for example, the C1-C10 substituted alkane refers to a C1-C10 alkane having its one or more hydrogen atoms substituted with a substituent. Therefore, as used herein, the term, "a divalent group having alkane or substituted alkane having two hydrogens removed" refers to a divalent group created by removing any two hydrogens from the above-described alkane or substituted alkane. The substituent is also designated as an alkylene group. These substituents include, but are not limited to, trimethylene (—$(CH_2)_3$—), tetramethylene (—$(CH_2)_4$—), pentamethylene (—$(CH_2)_5$—), and the like.

As used herein, the term, "cycloalkyl" refers to an alkyl having a cyclic structure. The term, "substituted cycloalkyl" refers to a cycloalkyl having its H substituted with the following substituent. Specific examples of these may include C3-C4 cycloalkyl, C3-C5 cycloalkyl, C3-C6 cycloalkyl, C3-C7 cycloalkyl, C3-C8 cycloalkyl, C3-C9 cycloalkyl, C3-C10 cycloalkyl, C3-C11 cycloalkyl, C3-C12 cycloalkyl, C3-C4 substituted cycloalkyl, C3-C5 substituted cycloalkyl, C3-C6 substituted cycloalkyl, C3-C7 substituted cycloalkyl, C3-C8 substituted cycloalkyl, C3-C9 substituted cycloalkyl, C3-C10 substituted cycloalkyl, C3-C11 substituted cycloalkyl or C3-C12 substituted cycloalkyl. For example, the cycloalkyl is represented by cyclopropyl, cyclohexyl, and the like.

The term, "alkenyl" refers to a monovalent group having one hydrogen atom removed from an aliphatic hydrocarbon having one double bond within the molecule, such as ethylene, propylene, and the like, and is generally represented by $C_nH_{2n-1}$— (wherein n is a positive integer of two or more). The term, "substituted alkenyl" refers to an alkenyl having its H substituted with the following substituent. Specific examples may include C2-C3 alkenyl, C2-C4 alkenyl, C2-C5 alkenyl, C2-C6 alkenyl, C2-C7 alkenyl, C2-C8 alkenyl, C2-C9 alkenyl, C2-C10 alkenyl, C2-C11 alkenyl, or C2-C12 alkenyl, C2-C3 substituted alkenyl, C2-C4 substituted alkenyl, C2-C5 substituted alkenyl, C2-C6 substituted alkenyl, C2-C7 substituted alkenyl, C2-C8 substituted alkenyl, C2-C9 substituted alkenyl, C2-C10 substituted alkenyl, C2-C11 substituted alkenyl, or C2-C12 substituted alkenyl. For example, C2-C10 alkenyl refers to a straight chain or branched alkenyl having 2-10 carbon atoms, and is represented by vinyl ($CH_2=CH-$), allyl ($CH_2=CHCH_2-$), $CH_3CH=CH-$, and the like. Also, for example, the C2-C10 substituted alkenyl refers to a C2-C10 alkenyl having its one or more hydrogen atoms substituted with a substituent.

As used herein, the term, "cycloalkenyl" refers to an alkenyl having a cyclic structure. The term, "substituted cycloalkenyl" refers to a cycloalkenyl having its H substituted with the following substituent. Specific examples of these may include C3-C4 cycloalkenyl, C3-C5 cycloalkenyl, C3-C6 cycloalkenyl, C3-C7 cycloalkenyl, C3-C8 cycloalkenyl, C3-C9 cycloalkenyl, C3-C10 cycloalkenyl, C3-C11 cycloalkenyl, C3-C12 cycloalkenyl, C3-C4 substituted cycloalkenyl, C3-C5 substituted cycloalkenyl, C3-C6 substituted cycloalkenyl, C3-C7 substituted cycloalkenyl, C3-C8 substituted cycloalkenyl, C3-C9 substituted cycloalkenyl, C3-C10 substituted cycloalkenyl, C3-C11 substituted cycloalkenyl, or C3-C12 substituted cycloalkenyl. For example, the preferred cycloalkenyl is represented by 1-cyclopentenyl, 2-cyclohexenyl, and the like.

The term, "alkynyl" refers to a monovalent group having one hydrogen atom removed from an aliphatic hydrocarbon having one triple bond within the molecule, such as acetylene, and is generally represented by $C_nH_{2n-3}$— (wherein n is a positive integer of two or more). The term, "substituted alkynyl" refers to an alkynyl having its H substituted with the following substituent. Specific examples may include C2-C3 alkynyl, C2-C4 alkynyl, C2-C5 alkynyl, C2-C6 alkynyl, C2-C7 alkynyl, C2-C8 alkynyl, C2-C9 alkynyl, C2-C10 alkynyl, C2-C11 alkynyl, C2-C12 alkynyl, C2-C3 substituted alkynyl, C2-C4 substituted alkynyl, C2-C5 substituted alkynyl, C2-C6 substituted alkynyl, C2-C7 substituted alkynyl, C2-C8 substituted alkynyl, C2-C9 substituted alkynyl, C2-C10 substituted alkynyl, C2-C11 substituted alkynyl, or C2-C12 substituted alkynyl. For example, C2-C10 alkynyl refers to a straight chain or branched alkynyl having 2-10 carbon atoms, and is represented by ethynyl ($CH''C-$), 1-propynyl ($CH_3C''C-$) and the like. Also, for example, the C2-C10 substituted alkynyl refers to a C2-C10 alkynyl having its one or more hydrogen atoms substituted with a substituent.

As used herein, the term, "alkoxy" refers to a monovalent group having a hydrogen atom removed from the hydroxy group of an alcohol, and is generally represented by $C_nH_{2n+1}O-$ (wherein n is a positive integer of one or more). The term, "substituted alkoxy" refers to an alkoxy having its H substituted with the following substituent. Specific examples of these may include C1-C2 alkoxy, C1-C3 alkoxy, C1-C4 alkoxy, C1-C5 alkoxy, C1-C6 alkoxy, C1-C7 alkoxy, C1-C8 alkoxy, C1-C9 alkoxy, C1-C10 alkoxy, C1-C11 alkoxy, C1-C12 alkoxy, C1-C2 substituted alkoxy, C1-C3 substituted alkoxy, C1-C4 substituted alkoxy, C1-C5 substituted alkoxy, C1-C6 substituted alkoxy, C1-C7 substituted alkoxy, C1-C8 substituted alkoxy, C1-C9 substituted alkoxy, C1-C10 substituted alkoxy, C1-C11 substituted alkoxy, or C1-C12 substituted alkoxy. For example, the C1-C10 alkoxy refers to a straight chain or branched alkoxy having 1-10 carbon atoms, and is represented by methoxy ($CH_3O-$), ethoxy ($C_2H_5O-$), n-propoxy ($CH_3CH_2CH_2O-$), and the like.

As used herein, the term "carbocyclic group" refers to a cyclic group containing only carbons, other than the aforementioned "cycloalkyl", "substituted cycloalkyl", "cycloalkenyl", "substituted cycloalkenyl". The carbocyclic group may be aromatic or non-aromatic, and monocyclic or polycyclic. The term "substituted carbocyclic group" refers to a carbocyclic group having the H of the carbocyclic group substituted with the following substituent. Specific examples may include C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12. substituted carbocyclic group. Also, the carbocyclic group may be C4-C7 carbocyclic group, or C4-C7 substituted carbocyclic group. The carbocyclic group is represented by a phenyl group having one hydrogen atom deleted. The deletion position of the hydrogen may be any chemically available position, and be on the aromatic ring or non-aromatic ring.

As used herein, the term, "heterocyclic group" refers to a cyclic group having carbon and a heteroatom. The heteroatom is selected from the group consisting of O, S and N, and maybe the same or different. One heteroatom, or two or more heteroatoms may be present in the heterocyclic group. The heterocyclic group may be aromatic or non-aromatic, and monocyclic or polycyclic. The term, "substituted heterocyclic group" refers to a heterocyclic group having the H of the heterocyclic group substituted with the following substituent. Specific examples may include those having one or more carbon atoms of the following groups substituted with one or more heteroatoms: C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12 substituted carbocyclic group. Also, the heterocyclic group may be those having one or more carbon atoms of the C4-C7 carbocyclic group or C4-C7 substituted carbocyclic group substituted with heteroatoms. The heterocyclic group is represented by thienyl group, pyrrolyl group, furyl group, imidazolyl group, pyridyl group, and the like. The deletion position of the hydrogen may be any chemically available position, and be on the aromatic ring or non-aromatic ring.

As used herein, the term, "carbocyclic group or heterocyclic group" may be substituted with a divalent substituent, in addition to a monovalent substituent, as defined below. Such divalent substitution may be an oxo substitution (=O) or a thioxo substitution (=S).

As used herein, the term, "halogen" refers to a monovalent group of the Group 7B element in the Periodic Table such as fluorine (F), chlorine (Cl), bromine (Br) iodine (I), and the like.

As used herein, the term, "hydroxy" refers to a group represented by —OH. The term, "substituted hydroxy" refers to a hydroxy having the H of the hydroxy substituted with a substituent as defined below.

As used herein, the term, "thiol" refers to a group (mercapto group) having the oxygen atom of the hydroxy group substituted sulfur atom, and is represented by —SH. The term, "substituted thiol" is a group having the H of the mercapto substituted with such a substituent as defined below.

As used herein, the term, "cyano" refers to a group represented by —CN. The term, "nitro" is a group represented by —NO$_2$. The term, "amino" is a group represented by —NH$_2$. The term, "substituted amino" is a group having the H of the amino substituted with such a substituent as defined below.

As used herein, the term, "carboxy" refers to a group represented by —COOH. The term, "substituted carboxy" is a group having the H of the carboxy substituted with such a substituent as defined below.

As used herein, the term, "thiocarboxy" refers to a group having the oxygen atom of the carboxy group substituted with sulfur atom, and is represented by —C(=S)OH, —C(=O)SH, or —CSSH. The term, "substituted thiocarboxy" refers to a group having the H of the thiocarboxy substituted with such a substituent as defined below.

As used herein, the term, "acyl" refers to a monovalent group having the OH removed from the carboxylic acid. Representative examples of the acyl groups include acetyl (CH$_3$CO—), benzoyl (C$_6$H$_5$CO—), and the like. The term, "substituted acyl" refers to a group having the hydrogen of the acyl substituted with such a substituent as defined below.

As used herein, the term, "amide" refers to a group having the hydrogen of ammonia substituted with an acidic group (acyl group), and is preferably represented by —CONH$_2$ The term, "substituted amide" refers to an amide that is substituted.

As used herein, the term, "carbonyl" collectively refers a group having —(C=O)— that is a characteristic group of aldehyde or ketone. The term, "substituted carbonyl" means a carbonyl group substituted with such a substituent as defined below.

As used herein, the term, "thiocarbonyl" refers to a group having the oxygen atom of the carbonyl substituted with sulfur atom, and contains a characteristic group —(C=S)—. The term, "substituted thiocarbonyl" means a thiocarbonyl substituted with such a substituent as selected below.

As used herein, the term "sulfonyl" is collectively refers to a group having a characteristic group —SO$_2$—. The term, "substituted sulfonyl" means a sulfonyl substituted with such a substituent as selected below.

As used herein, the term "sulfinyl" is collectively refers to a group having a characteristic group —SO—. The term, "substituted sulfinyl" means a sulfinyl substituted with such a substituent as selected below.

As used herein, the term, "alkylthio" refers to a group having an alkyl group bonded to a sulfur atom, and is generally represented by —S—R (wherein R is a group having one hydrogen atom removed from the alkyl).

As used herein, the term, "arylthio" refers to a group having an aryl group bonded to a sulfur atom, and is generally represented by —S'R (wherein R is a group having one hydrogen atom removed from the aryl).

As used herein, the term, "aryl" refers to a group generated by the elimination of one hydrogen atom bonded to the aromatic hydrocarbon ring, and is included in a carbocyclic group.

As used herein, the term, "substitution" refers to substituting an organic group or one or more hydrogen atoms in the substituent of an organic compound with other atom or atomic group, unless otherwise indicated. One hydrogen atom may be removed to substitute with a monovalent substituent, or two hydrogen atoms may be removed to substitute with a divalent substituent. As used herein, the substituent is defined as follows.

When a substituent R is substituted, R is represented by $R^A$—$(R^B)_n$, wherein $R^A$ is a (n+1) group having n hydrogen atoms removed from R;

$R^B$ may be selected from the group consisting of alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl.

When $R^B$ is substituted,
$R^B$ is represented by $R^C$—$(R^D)_n$, wherein $R^C$ is a (n+1) group having n hydrogen atoms removed from $R^B$;

$R^D$ may be selected from the group consisting of alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl.

When $R^D$ is substituted,
$R^D$ is represented by $R^E$—$(R^F)_n$, wherein $R^E$ is a (n+1) group having n hydrogen atoms removed from $R^D$;

$R^F$ may be selected from the group consisting of alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl.

When $R^F$ is substituted,
$R^F$ is represented by $R^G$—$(R^H)_n$, wherein $R^G$ is a (n+1) group having n hydrogen atoms removed from $R^F$;

$R^{1H}$ or $R^{2H}$ may be selected from the group consisting of alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl.

When $R^H$ is substituted, it may be substituted in the same manner as the substitution of $R^F$, and further substituent may be substituted in the same manner.

In addition, the number n of the above-discussed substituents may of course be a positive integer, and may be the same or different, and may each independently be selected. When n is 2 or more, each substituent that is represented by ( )n may be the same or different.

As used herein, C1, C2, . . . Cm represents the number of carbons, and C1 is used to represent a substituent having one carbon.

As used herein, the term, "optical isomer" refers to a pair of compounds or one of such compounds whose crystals or molecular structures are in a mirror image relationship, and cannot be overlapped. They are one form of steric isomers, and have the same properties except optical activity. The optical isomers as used herein are preferably those which are not naturally present in the samples.

(Sample Analysis)

As used herein, the term, "sample" may be available from any sources. These sources include those which use directly or indirectly (via a certain treatment) the whole or portions (for example, organs, tissues, cells, or the like) of organisms (for example, plants).

As used herein, the term, "reverse phase liquid chromatography" refers to a liquid chromatography using the stationary phase having a smaller polarity than the mobile phase that is reverse to an ordinary chromatography. Normally, in a reverse phase liquid chromatography, those molecules having less hydrophobicity are sequentially eluted. Preferably, a reverse phase liquid chromatography column may be a C18 column. As used herein, the term, "C18 reverse phase column (chromatography) " refers to a reverse phase liquid chromatography column packed with a filler having a carrier (for example, a silica gel carrier) chemically bonded to a stationary phase (octadecylsilyl, etc.) having a carbon number of 18. The term, "eluent" or "mobile phase" refers to a liquid used for elution in chromatography.

As used herein, "the calculation" from the chromatogram can be accomplished by extrapolating the actual values, using the relationship between the amounts of the substances used for the measurement standards and the absorbents, and the relationship between the substances to be measured and their standards.

As used herein, the term, "methanol extraction" refers to an organochemical extraction using methanol as the solvent. Preferably, the methanol extraction may be an extraction using methanol: water=80%:20% (v/v).

As used herein, the term, "etyl acetate extraction" refers to an organochemical extraction using a solvent comprising etyl acetate as a solvent system. Preferably, the etyl acetate extraction may be an extraction using about 100% ethyl acetate.

As used herein, the term "WRKY family", "WRKY superfamily" or "WRKY-type transcription factor" refers to a group of transcription factors with the WRKY region, which comprises a specific zinc finger motif for plants. The WRKY region is characterized by the consensus amino acid sequence, WRKYCQK (for example, see Trends Plant Sci 2000 May;5(5):199-206). Among the WRKY family, there are a number of factors that have immediate early type, transiently activated stress responsive properties. The WRKY family includes TIZZ and WIZZ. Further, amino acids as referres to herein may be referred to as either the three-letter symbol known in the art or the one-letter symbol recommended by IUPAC-IUB Biochemical Nomenclature Commission in general. Additionally, nucleotides may be referred to in the one-letter codes commonly recognized.

As used herein, the term "WIZZ (wound-induced leucine zipper zinc finger)" is stress responsive gene (see Hara et al., Mol. Gen. Genet. (2000), 263:30-37) wherein the stress is immediate early type, transiently activated stress (e.g., wound), and belongs to the WRKY family. Among the families, it belongs to the group II subfamily. This group II subfamily includes a WRKY region and a leucine zipper region in the N-terminus (Trends Plant Sci May 2000;5(5):199-206).

As used herein, the term "TIZZ" is a gene similar to "WIZZ" which has been found in tobacco, and is a wound responsive gene which is an immediate early type, transiently activated (see Yoda et al., Mol. Genet. Gennomics. (2002), 267:152-161), and belongs to the same WRKY group II subfamily as WIZZ. This group II subfamily includes a WRKY region and a leucine zipper region in the N-terminus (Trends Plant Sci May 2000;5(5):199-206).

As used herein, the term "rapid response" refers to a phenomenon that upon receiving a stimulus, the response to the stimulus occurs immediately (e.g., within one hour, preferably within 30 minutes, more preferably within 15 minutes) in organisms. In the rapid response, a rapid activation of a gene expression including transcription, translation and post-translation modification is involved. As used herein, "gene" refers to an agent defining a genetic trait. A gene is typically arranged in a given sequence on a chromosome. A gene includes a structural gene which defines the primary structure of protein and a regulatory gene which encodes a protein which regulates the expression of the structural gene. As used herein, "gene" may refer to "polynucleotide", "oligonucleotide", "nucleic acid", and "nucleic acid molecule" and/or "protein", "polypeptide", "oligopeptide" and "peptide".

As used-herein, the term "expression" of a gene, a polynucleotide, a polypeptide, or the like, indicates that the gene or the like is affected by a predetermined action in vivo to be changed into another form. Preferably, the term expression indicates that genes, polynucleotides, or the like are transcribed and translated into polypeptides. In one embodiment of the present invention, genes maybe transcribed into mRNA. More preferably, these polypeptides may have post-translational processing modifications. As used herein, the term "regulation" includes, but is not limited to, enhancement, reduction, induction, eliminating, delaying, accelerating of the gene expression, and the like.

As used herein, the term "screening" refers to selection of a target, such as an organism, a substance, or the like, a given specific property of interest from a population containing a number of elements using a specific operation/evaluation method. Screening may be performed using a system in vitro, in vivo, or the like (a system using a real substance) or alternatively a system in silico (a system using a computer). It is understood that within the invention, compounds obtained by screening would also be encompassed, as long as the compounds have at least one activity of those of the present invention.

Therefore, it is contemplated that the present invention provides drugs which are produced by computer modeling based on the present disclosure.

In other embodiments, the present invention includes compounds obtained by a quantitative structure activity relationship (QSAR) computer modeling technique as a tool for screening for effectiveness of the regulatory activity of the compound according to the present invention. Here, the computer technique includes some substrate templates prepared by a computer, pharmacophores, production of homologous models of the active site of the present invention, and the like. In general, a method for modeling an ordinary characteristic group of a substance capable of interacting with a given substance from data obtained in vitro can be carried out using a CATALYST™ pharmacophore method (Ekins et al., Pharmacogenetics, 9:477-489, 1999; Ekins et al., J. Pharmacol. & Exp. Ther., 288:21-29, 1999; Ekins et al., J. Pharmacol. & Exp. Ther., 290:429-438, 1999; Ekins et al., J. Pharmacol. & Exp. Ther., 291:424-433, 1999) and comparative molecular field analysis; CoMFA) (Jones et al., Drug Metabolism & Disposition, 24:1-6, 1996), and the like. In the present invention, the computer modeling may be carried out using molecular modeling software (e.g., CATALYST™ version 4 (Molecular Simulations, Inc., San Diego, Calif.), etc.).

Fitting of a compound to an active site can be carried out using any computer modeling technique known in the art. Visual inspection and manual operation of a compound to an active site can be carried out using a program, such as QUANTA (Molecular Simulations, Burlington, Mass., 1992) SYBYL (Molecular Modeling Software, Tripos Associates, Inc., St. Louis, Mo., 1992), AMBER (Weiner et al., J. Am. Chem. Soc., 106:765-784, 1984), CHARMM (Brooks et al., J. Comp. Chem., 4:187-217, 1983), or the like. In addition, energy minimization can be carried out using a standard force field, such as CHARMM, AMBER, or the like. Other more specialized computer modelings include GRID (Goodford et al., J. Med. Chem., 28:849-857, 1985), MCSS (Miranker and Karplus, Function and Genetics, 11:29-34, 1991), AUTODOCK (Goodsell and Olsen, Proteins: Structure, Function and Genetics, 8:195-202, 1990), DOCK (Kuntz et al., J. Mol. Biol., 161:269-288, (1982)), and the like. Additional structures of compounds can be newly constructed with blank active sites, active sites of known low molecular weight compounds, or the like, using a computer program, such as LUDI (Bohm, J. Comp. Aid. Molec. Design, 6:61-78, 1992), LEGEND (Nishibata and Itai, Tetrahedron, 47:8985, 1991), LeapFrog (Tripos Associates, St. Louis, Mo.), or the like. Such computer modelings are well known in the art and commonly used. Those skilled in the art can appropriately design compounds within the scope of the present invention in accordance with the disclosures of the present specification.

WIZZ is a disease responsive WRKY transcription factor whose transcription product is extremely rapidly accumulated when wound (Mol. Gen. Genet, 2000:263.30-37) and when infected with a pathogen (Mol. Genet. Genomic. 2002 267.154-161). It is indicated that some types of WRKY type transcription factor are activated by infection with a pathogen, the expression of pathogen-related proteins as a target gene is induced, are therefore involved in the defense response against the infection of the pathogen (Genes & Development 2002, 16, 1139-1149). As such, it is demonstrated that in plants, activation of the WRKY type transcription factor triggers physiological reactions in vivo. Therefore, if WIZZ is activated by the compound of the invention, then the expression of downstream defense-related gene(s) as targets are induced, and the resistant reaction against disease/wound stress is induced.

BEST MODES FOR CARRYING OUT THE INVENTION

The present invention provides a compound having the following structure:

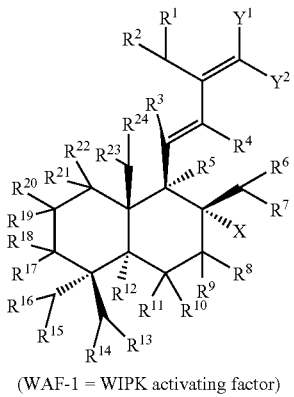

(WAF-1 = WIPK activating factor)

wherein, in the formula:

X is selected from the group consisting of hydroxy, substituted hydroxy, halogen, thiol, or substituted thiol. Preferably, X may be hydroxy or substituted hydroxy. More preferably, it may be hydroxy or alkyl-substituted hydroxy. Even more preferably, it may be hydroxy.

One of $Y^1$ and $Y^2$ may be hydrogen or alkyl, and the other may be Z-W, wherein Z may be a single bond, or a divalent group having alkane or substituted alkane having two hydrogen atoms removed, and W may be hydroxy, substituted hydroxy, aldehyde, carboxyl, or substituted carboxyl, but both of $Y^1$ and $Y^2$ may be Z-W, wherein Z may be a single bond, or a divalent group having alkane or substituted alkane having two hydrogen atoms removed, and W may be hydroxy, aldehyde, carboxyl, or substituted carboxyl. Preferably, one of $Y^1$ and $Y^2$ may be hydrogen, and the other may be methylol, substituted methylol, C1-aldehyde, C1-carboxyl, or C1-substituted carboxyl. More preferably, one of $Y^1$ and $Y^2$ may be hydrogen, and the other may be methylol, alkyl-substituted methylol, C1-aldehyde, C1-carboxyl, or C1-alkyl-substituted carboxyl. Even more preferably, one of $Y^1$ and $Y^2$ may be hydrogen, and the other may be methylol, methyl, or ethyl-substituted methylol, C1-aldehyde, C1-carboxyl, or C1-methyl or ethyl-substituted carboxyl.

$R^1$~$R^{24}$ is independently selected from the group consisting of hydrogen, alkyl, substituted alkyl, cyclo alkyl, substituted cyclo alkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl, and substituted sulfinyl. Preferably, $R^1$-$R^{24}$ may independently be selected from the group consisting of hydrogen, alkyl, and substituted alkyl. More preferably, it may be independently selected from the group consisting of hydrogen, and C1-C6 alkyl. All of $R^1$-$R^{24}$ may have substituents other than hydrogen, but preferably, have at least one hydrogen, more preferably, two hydrogens, three hydrogens, four hydrogens, five hydrogens, six hydrogens, seven hydrogens, eight hydrogens, nine hydrogens, ten hydrogens, eleven hydrogens, twelve hydrogens, thirteen hydrogens, fourteen hydrogens, fifteen hydrogens, sixteen hydrogens, seventeen hydrogens, eighteen hydrogens, nineteen hydrogens, twenty hydrogens, twenty one hydrogens, twenty two hydrogens, twenty three hydrogens. The presence of more hydrogens in the $R^1$-$R^{24}$ substituent may be preferable, because a larger substituent may interfere with the effects of the present invention. Therefore, preferred substituents other than hydrogen may include C1-C6 alkyl, C1-C5 alkyl, C1-C4 alkyl, C1-C3 alkyl, C1-C2 alkyl, methyl, and the like. However, a larger substituent may be preferred because it may enhance the effects of the invention. More preferably, all of $R^1$-$R^{24}$ may be hydrogens.

In one preferred embodiment, the present invention provides a compound having the following structural formula:

(WAF-1)

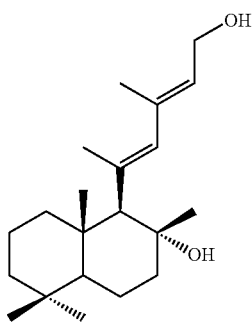

This compound is a Labdan-type diterpene compound that is (11E,13E)-labda-11,13-diene-8",15-diol.

The compounds of the present invention can be synthesized by using any of known techniques in the art. Such synthetic examples are illustrated below, but the synthesis methods of the present invention are not limited to these examples.

In one aspect, the synthesis method of the present invention comprises following steps:

1) reacting a compound:

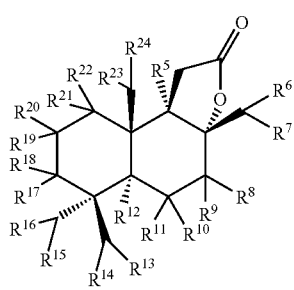

(an intermediate 1)

wherein, in the formula:

$R^5$-$R^{24}$ are independently selected from the group consisting of hydrogen, alkyl, and substituted alkyl, and the same as $R^1$-$R^{24}$ for WAF, with an alkyl lithium to provide an intermediate 2;

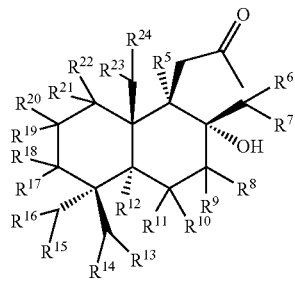

(an intermediate 2)

wherein the intermediate 1 may be dissolved in anhydrous $Et_2O$ (diethyl ether), and the alkyl lithium may be methyl lithium. The alkyl lithium may be dissolved in the $Et_2O$. The alkyl lithium may be added dropwise while stirring as cooling on ice under a nitrogen atmosphere. After the reaction, for example, the reactant may be extracted into the $Et_2O$ layer over five minutes under an acidic condition (e.g., 10% $H_2SO_4$). The product may be eluted into a suitable solvent (for example, using a silica gel column chromatography with hexane-$Et_2O$). The product may be identified as having the desirable structure by measuring the properties with NMR and MS.

2) mixing and reacting the product obtained in 1) with m-chloroperbenzoic acid and then with a 10% potassium hydroxide in methanol to provide an intermediate 4;

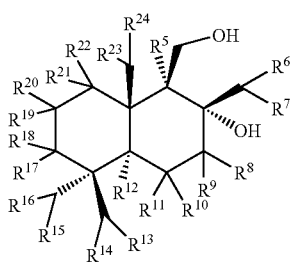

(the intermediate 4)

wherein the product may be an acetyl intermediate before being converted into the intermediate 4. The mixing can be accomplished while stirring on ice under a nitrogen stream. The residue may be dissolved into a solution of an alkali (for example, 10% KOH) in methanol. The reaction mixture may be extracted into $Et_2O$. The extract may be washed with a saturated aqueous $NaHCO_3$ solution, water, and a saturated brine. Optionally, it may be dried with $Na_2SO_4$. It may be eluted with a flash chromatography (hexane-AcOEt(3:1)).

3) reacting the product obtained in 2) with N-methylmorphorine N-oxide to provide an intermediate 5;

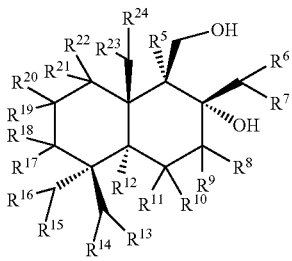

(the intermediate 5)

wherein the N-methylmorphorine N-oxide may be suspended in anhydrous $CH_2Cl_2$ with 4 Å molecular sieve. These reactions may be carried out while stirring on ice under a nitrogen stream. To this, tetrapropyl ammonium peruthenate may be added and reacted with. To the reaction mixture, $Et_2O$ may be added, stirred, and filtered with silica gel. The filtrate may be concentrated, subjected to a flash chromatography, and the product may be eluted into the hexane-$Et_2O$ elution portion.

(4) adding a compound

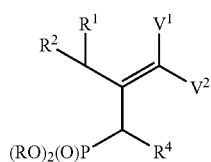

wherein, one of $V^1$ and $V^2$ is hydrogen or alkyl, and the other is Z-V, and wherein Z is (CH2)n-C(=O)—O—, V is alkyl, n is an integer of 0 or more, and R is alkyl (wherein R may preferably be a lower alkyl, and more preferably methyl), to said intermediate 5 obtained in the step (3) in an organic solvent in the presence of $NaNH_2$ to provide an intermediate (6):

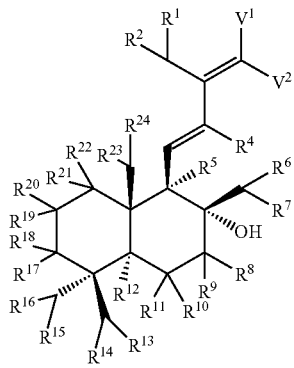

wherein $NaNH_2$ may be suspended in anhydrous THF, followed by the addition of the compound 28 while stirring on ice under a nitrogen stream. The reaction mixture may be cooled at −78', to which the intermediate 5 maybe added. The product may be extracted into $Et_2O$. The product may suitably be dried with $Na_2SO_4$. This may be isolated with a flash chromatography using hexane-AcOEt. The optical isomers may further be eluted with high performance liquid chromatography as using hexane-AcOEt and the like as the solvent;

(5) adding diisobutyl aluminum hydride in an organic solvent to said intermediate (6) obtained in the step (4) to provide

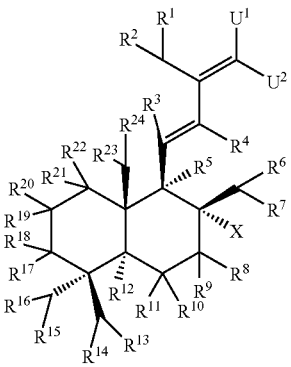

wherein, X is selected from the group consisting of hydroxy, substituted hydroxy, halogen, thiol, and substituted thiol;

one of $U^1$ and $U^2$ is hydrogen or alkyl, and the other is Z-U, wherein Z is a single bond, or a divalent group having alkane or substituted alkane having two hydrogen atoms removed, and U is hydroxy; and $R^1$-$R^{24}$ are independently selected from the group of hydrogen, alkyl, and substituted alkyl;

wherein the diisobutyl aluminum hydride may be dissolved in $CH_2Cl_2$ (preferably, under nitrogen stream), and thereafter returned to room temperature. The product may be added with AcOEt, $CH_2Cl_2$, potassium sodium tartrate and the like, and extracted with AcOEt. It may suitably be dried, and eluted with a flash chromatography using hexane-AcOEt (1:1).

Optionally, the method may comprise a further oxidation or substitution step where $Y^1$ is other than hydroxy.

In the above-described synthesis method, the substituents may be converted according to the following techniques where $Y^1$ is other than hydroxy.

Conversion from hydroxy into aldehyde: [$MnO_2$, heptane, 25° C.]: N. L. Wendler et al., J. Am. Chem. Soc., Vol. 73, 719 (1951); [$CrO_3$, pyridine, 25° C.]: J. R. Holum, J. Org. Chem., Vol. 26, 4814(1961).

Conversion from hydroxy into substituted methylol: [NaH, MeI, THF,25° C.]: C. A. Brown et al. , Synthesis, 1974, 434.

Conversion from hydroxy into carboxyl: [$NiO_2$, aqueous 1N NaOH solution, 50° C.]: K. Nakagawa et al., J. Org. Chem., Vol. 27, 1597(1962).

Examples of the starting materials in the above-described step 1) include a compound (sclareolide) having the structural formula:

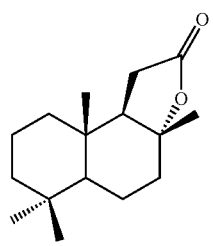

Sclareolide is commercially available, or may be synthesized as follows:

Therefore,
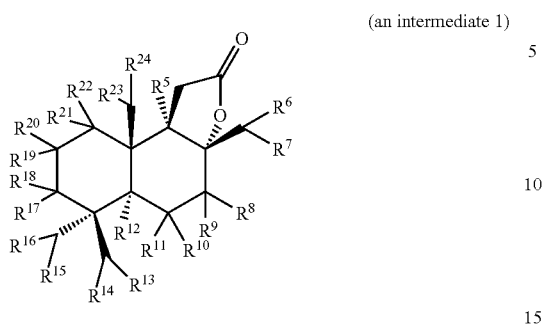
(an intermediate 1)
can readily be synthesized by those skilled in the art in view of the synthesis example of the sclareolide.
The reaction schemes when the above-described representative examples are illustrated below:
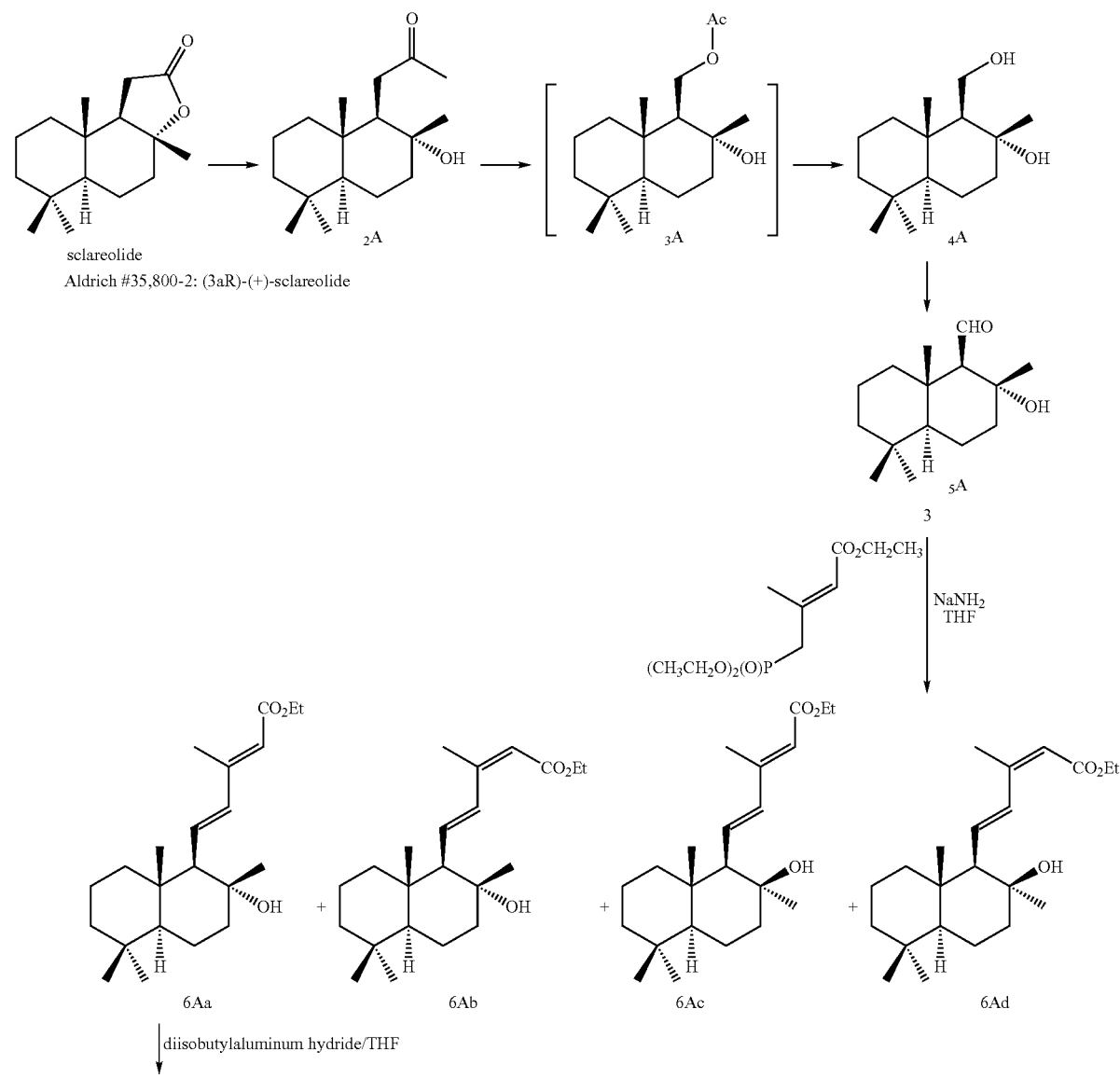

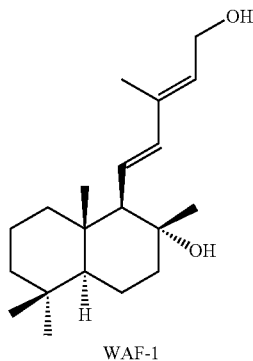

WAF-1

(Pharmaceutical Compositions, Agrichemical Compositions)

In another aspect, the present invention provides a composition comprising the compound of the present invention. These compositions may be pharmaceutical compositions, or agricultural (pesticide) compositions.

When the factor or compound is formulated into a pesticide or pharmaceutical composition, such a composition may contain an agriculturally or pharmaceutically acceptable carrier. These carriers include any materials known in the art.

These appropriate agriculturally or pharmaceutically acceptable factors include, but are not limited to the following: antioxidants, preservatives, colorants, flavoring agents, diluents, emulsifiers, suspending agents, solvents, fillers, extenders, buffers, delivery vehicles, excipients, and/or agricultural or pharmaceutical adjuvants. Typically, the pesticide or pharmaceutical composition of the present invention may be administered as a composition comprising the Labdan-type diterpenoid compound of the present invention together with one or more physiologically acceptable carriers, excipients or diluents. For example, an appropriate vehicle for the pharmaceutical composition may be water for injection, a physiological solution, or an artificial cerebral fluid, which may be supplemented with other materials that are common in a composition for parental administration. An appropriate vehicle for the pesticide composition may water for pesticide administration.

Illustrative appropriate carriers include neutral buffered saline, or saline mixed with serum albumin. Preferably, the product is formulated as a freeze-dried agent using a suitable excipient (for example, sucrose). Optionally, it may contain other standard carriers, diluents, and excipients. Other illustrative composition contains a Tris buffer of pH 7.0-8.5, or an acetic acid buffer of pH 4.0-5.5, and may further contain sorbitol, or its suitable alternative. The pH of the solution should be selected based on the relative solubility of the factor of the present invention.

The solvent for the composition may be either aqueous or non-aqueous. Further, its vehicle may contain other formulations for modifying or retaining the pH, osmolarity, viscosity, clarity, color, sterility, stability, isotonicity, disintegration rate, or odor. Similarly, the composition of the present invention may contain other formulations for modifying or retaining a rate of the active ingredients, or facilitating the absorption or permeation of the active ingredients.

When the composition of the present invention is formulated as a pharmaceutical composition, it may be parenterally administered. Alternatively, the composition may be intravenously or subcutaneously administered. When the pharmaceutical composition used in the present invention is systemically administered, it may be in the form of an orally acceptable aqueous solution that does not contain any pyogenic substance. The preparation of such a pharmaceutically acceptable protein solution is within the skill of the art, provided that attention be given to pH, isotonicity, stability, and the like.

When the composition of the present invention is formulated as a pharmaceutical composition, it may be prepared for storage in the form of a freeze-dried cake or aqueous solution by optionally mixing the selected composition having a desirable degree of purity with a physiologically acceptable carrier, excipient, or stabilizer (See, Pharmacopoeia of Japan; Remington's Pharmaceutical Sciences, 18th Edition, A. R. Gennaro, ed., Mack Publishing Company, 1990, etc.).

When the composition of the present invention is formulated as a pesticide composition, it may optionally contain an agriculturally acceptable carrier, excipient, or stabilizer, or the like.

The acceptable carriers, excipients, or stabilizers are non-toxic to the recipient, and preferably inactive to the dosage and concentration to be used, and include the following: phosphates, citrates, or other organic acids; antioxidants (such as ascorbic acid); low molecular weight polypeptides; proteins (such as serum albumin, gelatin, or immunoglobulin); hydrophilic polymers (such as polyvinyl pyrrolidone); amino acids (such as glycine, glutamine, arginine, or lysine); monosaccharides, disaccharides, and other carbohydrates (including glucose, mannose, or dextrin); chelating agents (such as EDTA); sugar alcohol (such as mannitol, or sorbitol); salt-forming counterions (such as sodium); and/or nonionic surfactants (such as Tween, Pluronic, or polyethylene glycol (PEG)).

When the composition of the present invention is used as a pesticide composition, the following pesticide active ingredients may concurrently be contained:

(herbicides) pyrazonate, daimuron, bromobutide, mefenacet, MCP, MCPB, triclopyr, naproanilide, CNP, chlomethoxynil, bifenox, MCC, pyributicarb, DCPA, napropamide, diphenamid, propyzamide, asulam, DCMU, linuron, methyldymron, tebuthiuron, bensulfuronmethyl, simazine, atrazine, simetryn, ametryn, prometryn, dimethametryn, metribuzin, bentazone, oxadiazon, pyrazonate, benzofenap, glyphosate, bilanafos, alloxydim, imazosulfuron, azimsulfuron, pyrazosulfuron, cinosulfuron;

(insecticides/acaricides) diazinon, fenthion, isoxathion, pyridaphenthion, fenitrothion, dimethoate, PMP, dimethylvinphos, acephate, DEP, NAC, MTMC, MIPC, PHC, MPMC, XMC, BPMC, bendiocarb, pirimicarb, methomyl, oxamyl, thiodicarb, cypermethrin, cartap hydrochloride, thiocyclam, bensultap, pyriproxyfen, phenoxycarb, methoprene, diflubenzuron, teflubenzuron, chlorfluazuron, buprofezin, hexythiazox, pyridaben, clofentezine, nitenpyram;

(bactericides) probenazole, isoprothiolane, pyroquilon, flutolanil, metominostrobin, ziram, thiram, captan, TPN, phthalide, tolclofos-methyl, fosetyl, thiophanate methyl, benomyl, carbendazole, thiabendazole, diethofencarb, iprodione, vinclozolin, procymidone, fluoroimide, oxycarboxin, mepronil, flutolanil, pencycuron, metalaxyl, oxadixyl, triadimefon, hexaconazole, triforine, blasticidin-S, kasugamycin, polyoxin, validamycin-A, mildiomycin, PCNB, hydroxyisoxazole, dazomet, dimethirimol, diclomezine, triazine, ferimzone, tricyclazole, oxolinic acid, and the like, and preferably strobilurin-based compounds, such as metominostrobin and the like.

When a composition of the present invention is used as an agricultural chemical, the composition may be mixed with an acaricide (e.g., chlorobenzilate, etc.), a plant growth regulator (e.g., paclobutrazol, etc.), anematocide (e.g., benomyl, etc.), a synergist (e.g., piperonyl butoxide, etc.), an attractant (e.g., eugenol, etc.), a repellent (e.g., creosote, etc.), a pigment (e.g., food blue No. 1, etc.), a fertilizer (e.g., urea, etc.), or the like.

When the composition of the present invention is used as a pharmaceutical composition, the composition further contains the following medicinal ingredients:

central nerve system drugs (e.g., general anesthetics, sedative-hypnotics, anxiolytics, antiepileptics, anti-inflammatory agents, stimulants, antihypnotics, antiparkinson agents, antipsychotics, combination cold remedies, and the like);

peripheral nerve agents (e.g., local anesthetics, skeletal muscle relaxants, autonomic nerve agents, antispasmodic agents, and the like);

sensory organ drugs (e.g., ophthalmological agents, otorhinolaryngological agents, antidinics, and the like);

circulatory organ drugs (e.g., cardiotonics, antiarrhythmics, diuretics, antihypertensive agents, vasoconstrictors, vasodilators, antihyperlipemia agents, and the like);

respiratory organ drugs (e.g., respiratory stimulants, antitussives, expectorants, antitussive extpectorants, bronchodilators, collutoriums, and the like);

digestive organ drugs (e.g., stegnotics, antiflatuents, peptic ulcer agents, stomachics, antacids, cathartics, enemas, cholagogues, and the like);

hormone agents (e.g., pituitary gland hormone agents, salivary gland hormone agents, thyroid gland hormone agents, accessory thyroid gland hormone agents, anabolic steroid agents, adrenal gland hormone agents, androgenic hormone agents, estrogen agents, progesterone agents, mixed hormone agents, and the like);

urogenital organ and anal drugs (e.g., urinary organ agents, genital organs agents, uterotonics, hemorrhoids agents, and the like);

dermatologic drugs (e.g., dermatologic disinfectants, wound protecting agents, pyogenic diseases agents, analgesics, antipruritics, astringents, antiphlogistics, parasitic skin diseases agents, emollients, hair agents, and the like);

dental and oral agents;

drugs for other organs;

vitamin agents (e.g., vitamin A agents, vitamin D agents, vitamin B agents, vitamin C agents, vitamin E agents, vitamin K agents, mixed vitamin agents, and the like);

nutritive agents (e.g., calcium agents, inorganic preparations, saccharide agents, protein amino acid preparations, organ preparations, infant preparations, and the like);

blood and body fluid drugs (e.g., blood substitute agents, styptics, anticoagulants, and the like);

dialysis drugs (e.g., kidney dialysis agents, peritoneal dialysis agents, and the like);

other metabolic drugs (e.g., organ disease agents, antidotes, antabuses, arthrifuges, enzyme preparation, diabetic agents, and others);

cell activating agents (e.g., chlorophyll preparations, pigment agents, and the like);

tumor agents (e.g., alkylation agents, antimetabolites, antineoplastic antibiotic preparations, antineoplastic plant extract preparations, and the like);

radiopharmaceuticals;

allergy drugs (e.g., antihistamine agents, irritation therapy agents, non-specific immunogen preparations, and other allergy drugs, crude drugs and drugs based on Chinese medicine, crude drugs, Chinese medicine preparations, and other preparations based on crude drug and Chinese medicine formulations);

antibiotic preparations (e.g., acting for gram-positive bacteria, gram-negative bacteria, gram-positive mycoplasmas, gram-negative mycoplasmas, gram-positive rickettsia, gram-negative rickettsia, acid-fast bacteria, molds, and the like);

chemotherapeutic agents (e.g., sulfa drugs, antitubercular agents, synthetic antimicrobial agents, antiviral agents, and the like);

biological preparations (e.g., vaccines, toxoids, antitoxins, leptospire antisera, blood preparations, biological test preparations, and other biological preparations, and antiprotozoal drugs, anthelmintics, and the like);

dispensing agents (e.g., excipients, ointment bases, solvents, flavors, colorants, and the like);

diagnostic drugs (e.g., contrast media, function testing reagents, and the like);

sanitation drugs (e.g., preservatives);

xenodiagnostic drugs (e.g., cytologic examination drugs, and the like);

non-categorized drugs which do not aim mainly for therapy; and narcotics (e.g., opium alkaloid drugs, coca alkaloid preparations, synthetic narcotics, and the like)

Although the following illustrate the detailed description of the application of the present invention to plants, which is the preferred aspect of the present invention, it is to be understood that the present invention may be applied to other organisms such as animals.

In one embodiment, the composition of the present invention is provided for imparting stress resistance to a plant or augmenting said stress resistance. Preferably, said stress resistance comprises at least one resistance selected from the group consisting of wound resistance, insect resistance, disease resistance, and hypersensitivity cell death resistance.

In certain embodiments, the imparting or augmenting of said stress resistance to an organism in the present invention is accomplished by controlling the activity of at least one protein selected from the group consisting of wound-induced protein kinases, and salicylic acid-induced protein kinases. The wound-induced protein kinases, and salicylic acid-induced protein kinases are known in the art.

In another embodiment, the imparting or augmenting of said stress resistance to an organism in the present invention is accomplished by controlling at least one signaling system selected from the group consisting of jasmonic acid signaling systems and salicylic acid signaling systems. The jasmonic acid signaling systems are outlined in "Cell Technology Additional Volume, Plant Cell Technology Series 10, The Signaling Systems of Plant hormones—Biosynthesis to Physiology—(Hirotoyo Fukuda, ed.), Chapter 6 (The Physiology, Biosynthesis, and Signaling Systems of Jasmonic Acid, pages 190-198)", and the like, and the salicylic acid signaling systems are outlined in "The Plant Cell, Vol. 13, 1877-1889, 2001", and the like.

In another aspect, the present invention provides a method of imparting stress resistance to an organism such as a plant or augmenting said stress resistance, wherein said method comprises the following steps:

1) applying the compound or composition of the present invention to said plant. In a preferred embodiment, said compound may be a compound having such a preferred substituent as described above. In a preferred embodiment, said compound may take the form of a composition (such as agricultural composition).

In one preferred embodiment, said stress resistance may be at least one resistance selected from the group consisting of wound resistance, insect resistance, disease resistance, and hypersensitivity cell death resistance.

In another preferred embodiment, the imparting or augmenting of said stress resistance may be accomplished by controlling the activity of at least one protein selected from the group consisting of wound-induced protein kinases, and salicylic acid-induced protein kinases.

In another preferred embodiment, the imparting or augmenting of said stress resistance may be accomplished by controlling at least one signaling system selected from the group consisting of jasmonic acid signaling systems and salicylic acid signaling systems.

In another aspect, the present invention provides a method of producing stress resistant plants. Said method comprises:

1) applying the compound or composition of the present invention to said plant. In a preferred embodiment, said compound may be a compound having such a preferred substituent as described above. In a preferred embodiment, said compound may take the form of a physiologically acceptable composition (such as agricultural composition) The present invention also relates to a plant obtained by such a method. The plant can be obtained by a technique well known in the art. For example, the plant can be obtained by spraying the composition of the present invention on a certain plant.

In another aspect, the present invention provides a method of producing stress resistant plant tissues. Said method comprises:

1) applying the compound or composition of the present invention to said plant tissue. In a preferred embodiment, said compound may be a compound having such a preferred substituent as described above. In a preferred embodiment, said compound may take the form of a physiologically acceptable composition (such as agricultural composition) The present invention also relates to a plant tissue obtained by such a method. A technique for obtaining the plant tissue is well known in the art. For example, the plant tissue may be a tissue of the plant structure such as callus, stem, leaf, flower, seed, and the like. In such a case, it can be made by isolating the plant tissue, and applying the compound or composition of the present invention to the isolated plant tissue.

In another aspect, the present invention provides a method of producing stress resistant plant cells. Said method comprises:

1) applying the compound or composition of the present invention to said plant cell. In a preferred embodiment, said compound may be a compound having such a preferred substituent as described above. In a preferred embodiment, said compound may take the form of a physiologically acceptable composition (such as agricultural composition) The present invention also relates to a plant cell obtained by such a method.

In another aspect, the present invention provides a method of producing stress resistant plant seeds. Said method comprises:

1) applying the compound or composition of the present invention to said plant; and obtaining said seed from said plant. In a preferred embodiment, said compound may be a compound having such a preferred substituent as described above. In a preferred embodiment, said compound may take the form of a physiologically acceptable composition (such as agricultural composition). The present invention also relates to a plant seed obtained by such a method. A technique for obtaining the plant seed is well known in the art. For example, if the plant is a flowering plant, the seed can be obtained by fertilizing the plant using any technique well known in the art.

In another aspect, the present invention provides a method of quantifying the compound of the present invention: The method comprises 1) providing a sample; 2) adding the predetermined amount of the steric isomer of a compound to be quantified to said sample; 3) separating said sample by a reverse phase liquid chromatography; and 4) calculating the amount of said compound from said separated steric isomer. In a preferred embodiment, said compound to be quantified has the following structural formula:

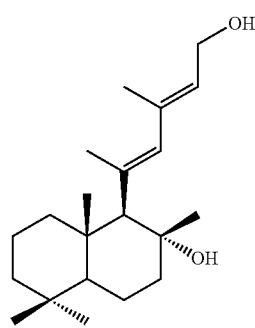

(WAF-1)

said steric isomer has the following structural formula:

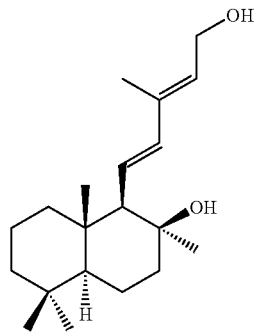

(Labdan a)

Preferably, said sample is extracted with methanol and subsequently with ethyl acetate, prior to the separation with said reverse phase liquid chromatography. This is advantageous for the measurement of the present compound to be measured, since the methanol extraction is expected to supress the metabolism and decomposition of the present compound due to the enzyme reaction, and the ethyl acetate extraction is expected to improve the extraction efficiency. The ratio of each of these plural solvents may be varied depending upon the conditions of the sample. Therefore, the methanol extraction may be an extraction of a lower (preferably, C1-C6) alcohol such as ethanol. Preferably, the methanol extraction may be an extraction using methanol:water=80%:20% (v/v), but other ratios may be used. Preferably, the ethyl acetate extraction may be an extraction using about 100% ethyl acetate, but those having other solvents (such as chloroform) may be used.

Preferably, the separation with said reverse phase liquid chromatography comprises a separation with a C18 reverse chromatography column, and said separation comprises a first separation in 80%:20% (v/v) methanol:water, and a separation with 9:8 (v/v) acetonitrile:water. The ratio of each of these plurality of solvents may be varied depending upon the conditions of the sample and the kind of compound to be measured. Therefore, solvent systems such as water/2-propanol, water/ethanol, and the like can be used.

Preferably, said calculation comprises the correction of the recovery loss. The recovery loss can be determined by $X = Y \cdot 100/Z$, wherein Y is the actual measurement value, X is the amount at the 100% recovery percentage, and Z(%) is the actual recovery percentage.

In another aspect, the present invention provides a composition for inducing a rapid accumulation of a WRKY family gene in a plant under a condition requiring the accumulation of a WRKY family gene. The composition comprises the compound of the present invention. The composition may further comprise agriculturally acceptable substances (such as excipients). The composition may also comprise other agriculturally active agents.

In a preferred embodiment, said compound has the following structural formula:

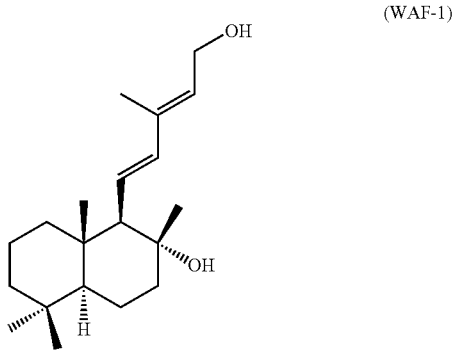

(WAF-1)

In a preferred embodiment, the condition requiring the accumulation of said WRKY family gene may be a condition requiring the rapid response to stress.

Preferably, said plant may be provided with wound resistance, insect resistance, disease resistance, and hypersensitivity cell death resistance by inducing a rapid accumulation (for example, within 30 minutes, more preferably within 15 minutes) of said WRKY family gene.

Preferably, said WRKY family gene may be WIZZ or TIZZ.

In another aspect, the present invention provides a composition for regulating the expression of a WRKY family gene. Said composition comprises the compound of the present invention. The composition may further comprise agriculturally acceptable substances (such as excipients) The composition may also comprise other agriculturally active agents.

In another aspect, the present invention provides a method of inducing a rapid accumulation of a WRKY family gene in a plant under a condition requiring the accumulation of a WRKY family gene. Said method comprises a) applying to said plant the compound of the present invention.

Preferably, said compound has the following structural formula:

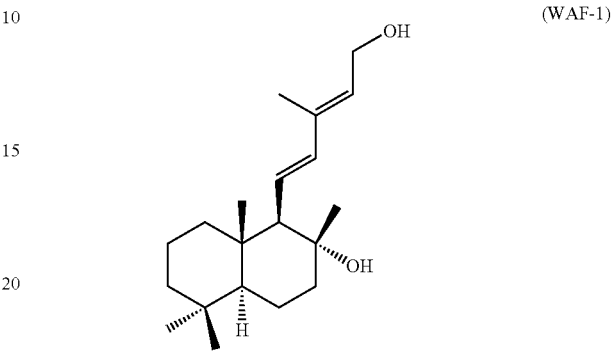

(WAF-1)

In a preferred embodiment, the condition requiring the accumulation of said WRKY family gene may be a condition requiring the rapid (for example, within 30 minutes, more preferably within 15 minutes) response to stress.

In a preferred embodiment, said plant may be provided with wound resistance, insect resistance, disease resistance, and hypersensitivity cell death resistance by inducing a rapid accumulation of said WRKY family gene.

In the above method, preferably, said WRKY family gene may be WIZZ or TIZZ. The preferred gene may be varied depending upon the plant variety to be treated.

Preferably, the compound of the present invention may be applied immediately after the accumulation of said WRKY family gene is required. The application techniques include various techniques such as direct spraying, and the like.

In another aspect, the present invention provides a composition for regulating the expression of a WRKY family gene. Said composition comprises the compound of the present invention. The composition may further comprise agriculturally acceptable substances (such as excipients) The composition may comprise other agriculturally active agents.

In a further aspect, the present invention provides a composition for facilitating the elongating growth or auxetic growth of a plant.

In another aspect, the present invention provides a composition for inhibiting the elongating growth of a plant.

In further aspect, the present invention provides a composition for facilitating the maturation of a plant.

In further aspect, the present invention provides a composition for regulating the flowering of a plant.

In preferred embodiments, these compositions comprise the compound of the present invention. The composition may further comprise agriculturally acceptable substances (such as excipients). The composition may also comprise other agriculturally active agents.

Preferably, the compound of the present invention may facilitate the elongating growth or auxetic growth of the above-described plant, inhibit the elongating growth of the plant, facilitate the maturation of the plant, or regulate the flowering of the plant by the rapid accumulation of an ACO gene, or the rapid accumulation of ethylene. The techniques for these include various techniques such as direct spraying, diffusing, and the like.

In another aspect, the present invention provides a method of facilitating the elongating growth or auxetic growth of a plant. The method comprises 1) applying the compound of the present invention to the above-described plant.

In another aspect, the present invention provides a method of inhibiting the elongating growth of a plant. The method comprises 1) applying the compound of the present invention to the above-described plant.

In a further aspect, the present invention provides a method of facilitating the maturation of a plant. The method comprises 1) applying the compound of the present invention to the above-described plant.

In a further aspect, the present invention provides a method of controlling the flowering of a plant. The method comprises 1) applying the compound of the present invention to the above-described plant.

In a preferred embodiment, said compound may be a compound having such a preferred substituent as described above. In a preferred embodiment, said compound may take the form of a physiologically acceptable composition (such as agricultural composition). The present invention also relates to a plant obtained by such a method. The plant can be obtained by a technique well known in the art. For example, the plant can be obtained by spraying the composition of the present invention on certain plant.

In one aspect, the present invention provides a medium for regulating the growth (proliferation), differentiation or regeneration of a plant, plant structure or plant tissue, or plant cell. The medium contains the compound of the present invention. The medium may further contain ingredients that are employed in other common cell cultures, and plant tissue cultures. The medium may also contain agriculturally acceptable substances (such as excipients).

The following examples illustrate the present invention, but these examples are for the purpose of illustration only. The scope of the present invention is not limited by the examples, but by only the claims.

EXAMPLES

Example 1

Isolation and Purification of WIPK Activator in Tobacco (Plant Material)

Tobacco leaf infected with tobacco mosaic virus (TMV) was used as a material in this example to conduct isolation of WIPK activator because it was known that WIPK was dramatically activated in tobacco leaf infected with TMV.

Superior healthy leaves of two-month-old tobacco (Nicotiana tabacum cv. Samsun—NN) plant bodies were cut and silicon carbide (brand name: Carborundum, Kishida Chemical Co., Ltd., Osaka, Japan) was applied to the epidermis, against which 10 mM sodium phosphate buffer (pH 7.0) containing TMV was rubbed to inoculate with TMV. To complete the infection, this healthy leaf was allowed to stand at room temperature for 30 minutes and washed with water removing the silicon carbide, after air drying, was put into a transparent plastic box spread with wet filter papers, followed by culture at 30° C. for 40 hours, then at 20° C. for 6 hours.

The light condition during culture was continuous irradiation with white fluorescent light (approximately 6,000 lux). The inoculated leaf, after culture, was snap-frozen in liquid nitrogen and immediately used as material from which to prify WIPK activator.

(Purification of WIPK Activator)

Plant material was put into a homogenizer (brand name: Polytron, Kinematica, Switzerland) and homogenized in 4 volumes of cold 80% (v/v) acetone (i.e. 4 ml for 1 g material) to a fine powder, and the homogenate was extracted by standing at 4° C. for two hours. The extract was filtered with a filter paper (Toyo Roshi Kaisha, Co., Ltd., Japan). The residue after filtration was washed with a small amount of 80% (v/v) acetone and, combinedwiththe above filtrate, and concentrated under reduced pressure at 35° C. to the aqueous phase. The resultant aqueous phase was adjusted with hydrochloric acid to pH 3.0 and extracted with ethyl acetate of the same amount three times. The resultant ethyl acetate phase was extracted with the same amount of 5% (w/v) sodium bicarbonate twice, then the surface ethyl acetate phase was dehydrated with anhydrous sodium sulfate and concentrated under reduced pressure at 35° C. to dryness.

The dried substance was dissolved in hexane containing a small amount of 10% (v/v) ethyl acetate and the dissolved substance was applied to a column (internal diameter 3 cm, length 50 cm) and filled with silica gel (Wakogel C-200, Wako Pure Chemical, Osaka, Japan). A mixed solution of ethyl acetate/hexane was used as the solvent system. A mixed solution at 10% (v/v) of ethyl acetate concentration in the mixture of hexane and ethyl acetate was applied first and then a mixed solution at 20% (v/v) was then applied, followed by a stepwise increase in increments of 10%. The mixed solution was applied in 900 ml aliqots each time. The resultant eluted fractions was concentrated under reduced pressure at 35° C. to dryness and each dried substance was dissolved in 10 ml ethyl acetate, some of which (3, 30, 100 and 300 µl) were subjected to a WIPK induced activity assay.

The WIPK induced activity assay was conducted as follows: A filter paper was spread in a glass Petri dish of 3 cm inside diameter, onto which the test solution for assay was added, organic solvent was removed under the flow of nitrogen gas, and 10 mM Mes-NaOH (pH 5.6) of 1 ml was added, on which three leaf disks (diameter 9 mm) stamped out of the tobacco leaves were placed per Petri dish and cultured at 24° C. In two hours, the disks were collected and immediately frozen in liquid nitrogen to be used in WIPK activity measurement that was conducted following the method described in Seo et al. (1999) Plant Cell 11, 289-291. The outline is as follows:

Crude protein of 50 µg and anti-WIPK antibody were reacted and the myelin basic protein phosphorylation activity of WIPK in the resultant immune complex was measured.

WIPK activity was detected in the fractions from 60% (v/v) to 80% (v/v) of ethyl acetate concentration in hexane. Therefore, these fractions were combined and concentrated under reduced pressure at 35° C. to dryness. The resultant dried substance was dissolved in water containing a small amount of 10% (v/v) methanol and the dissolved substance was added into a solid phase extraction column cartridge of reverse phase type (C18 Sep-Pak, Waters, USA). A mixed solution of methanol/water was used as a solvent system. The mixed solution of 10% (v/v) methanol solution in water was applied first to elute, then A mixed solution of 20% was applied, followed by a stepwise increase in increments of 10% (v/v) methanol concentration. A mixed solution of 10 ml was applied each time. The resultant eluted fractions were concentrated under reduced pressure at 35° C. to dryness, the dried fractions were dissolved in 10 ml methanol, some of which (3, 30, 100 and 300 µl) was subjected to a WIPK induced activity assay. The assay procedure was as above.

Activity was detected in a fraction at 80% (v/v) methanol concentration in a mixed solution of water/methanol, so this fraction was concentrated under reduced pressure at 35° C. to dryness. The resultant dried residue was dissolved in a small amount of mobile phase (methanol:water=4:1, v/v) and the dissolved substance was infused to a HPLC system fitted with reverse phase high performance liquid chromatography (HPLC) column (LiChrospher 100RP-18, 5 µm particle size, 4 mm ID by 25-cm long, Hewlett Pachard). The above mobile phase was used as a solvent system, flow was at 1 ml/min flow rate, and the ultraviolet absorption was monitored and measured at the constant-wavelength of 254 nm. From 0.1 minute after infusion, each of 3 ml aliquots of eluate were collected in 90 fractions in total. Each fraction was concentrated under reduced pressure at 35° C. to dryness and each dried fractions were dissolved in 10 ml methanol, some of which (3, 30, 100 and 300 µl) was subjected to a WIPK induced activity assay. The assay procedure was as above.

Activity was detected in the fractions eluted from 12.1 to 15.1 minutes, so this faction was further fractionated by the above HPLC column. A solvent (Acetonitrile:water=3:2 (v/v)) was used as the solvent system and flow was at 1 ml/min, and the ultraviolet absorption was monitored and measured at the constant-wavelength of 254 nm. Activity was found in the peak at 14.6 minutes retention time, so this peak was collected (FIG. 1).

This peak was used as an isolated WIPK activator for assay thereafter.

Example 2

Biological Activity Assay of Isolated Material

Isolated material was dissolved in dimethyl sulfoxide (DMSO) and diluted with 10 mM Mes-NaOH (pH 5.6) to an adequate concentration. If it was used in an assay, the DMSO concentration was kept below 0.1%. Superior healthy leaves of 50-day-old tobacco (*Nicotiana tabacum* cv. Samsun NN) plant bodies were cut from the petiole, immediately put into a test tube, 10 mM Mes-NaOH (pH 5.6) solution containing isolated active substance of the invention at each concentration was added, and culture was conducted at 24° C. 10 mM Mes-NaOH (pH 5.6) without active substance of the invention was used as a control group. In a certain amount of time, the leaves were collected and immediately frozen in liquid nitrogen to conduct WIPK activity measurement or RNA extraction for Northern blot analysis. WIPK activity measurement, RNA extraction and Northern blot analysis were performed following Seo et al. (1999) plant Cell 11, 289-291. WIPK activity was measured 15 minutes after the subject was allowed to absorb the isolated compound at the given concentration through the petiole. Only buffer was absorbed in a control group. As another control group (healthy leaf), leaves were cut from tobacco plant body to be immediately subjected to WIPK activity measurement. For proteinase inhibitor II (PI-II), basic PR-1, basic PR-2 genes and ACO, transcription product amounts of PI-II, basic PR-1, basic PR-2 genes and ACO-coding gene were measured after allowing the subject absorb the isolated compound at the given concentration through the petiole for a period of time. As a control group, only buffer was absorbed. The outline is as follows:

Nucleic acid hybridization reaction was performed on nylon membrane containing 20 µg total RNA with $^{32}$P-radiolabeled cDNA of tobacco PI-II, basic PR-1, basic PR-2 genes and ACO-coding gene. After the membrane was washed it was used to expose to an X-ray film.

(Effects of Isolated Substance on JA and SA accumulation)

To evaluate whether the induction of basic pathogenesis-related protein gene (PR-1 and PR-2) and proteinase inhibitor II gene by synthetic substance occurred through JA or SA, 100 nM or 1 µM WAF-1 or water was absorbed into tobacco leaves through the petiole, followed by culture at 24° C., to measure the intrinsic level of JA.

(Effects of Synthetic Substance on Ethylene Accumulation)

Ethylene acts as a signal in the induction of basic PR protein of tobacco plant, so the release of ethylene was measured after externally giving WAF-1 to a tobacco leaf as above to evaluate the effects of synthetic substance on ethylene accumulation.

(Results)

(Effects of Isolated Substance on the Induction of WIPK Activity)

Figure 2:
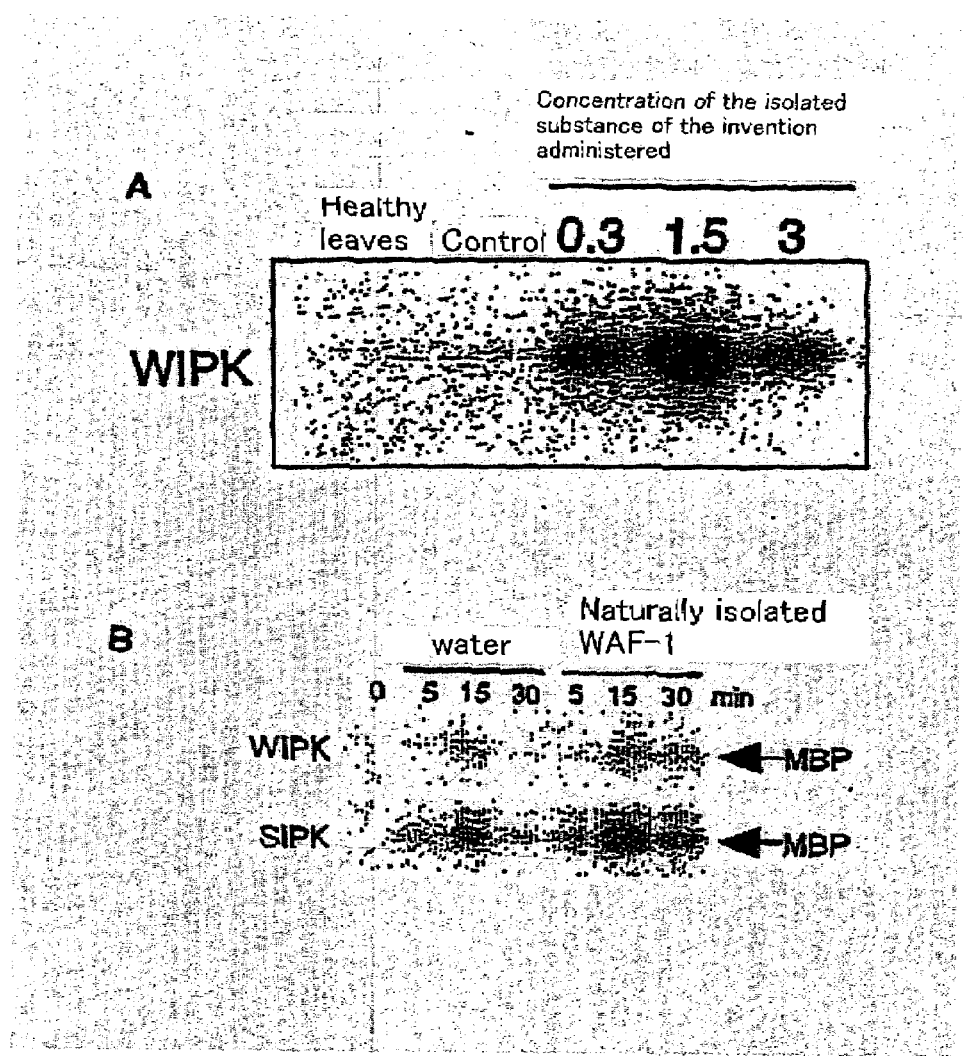
FIG. 2A shows the effects of the compound of the invention on the induction of WIPK activity. The isolated compound at the concentrations indicated was absorbed into the subject through the petiole and WIPK activity was measured after 15 minutes. As a control group, a buffer only was absorbed into the subject. As another control group (healthy leaves), leaves were cut from the tobacco plant body and were subjected to WIPK activity measurement immediately.
FIG. 2B shows the result of WIPK activity (MBP phosphorylation) that was measured 5 min, 15 min, and 30 min after the naturally isolated substances at some concentrations (1 nM, 5 nM and 10 nM) and water as control are given from petiole to leaves. The induction of WIPK activity was observed at 5 min and maximum activation at 15 min and it was found that maximum activity is maintained even after 30 min.

The isolated substance at each concentration shown in FIG. 2A was given to a leaf through the petiole to measure WIPK activity at 15 minutes, resulting in the induction of WIPK activity at any concentration. In the treatment to a control group, little activity was observed.

Natural isolated substances at certain concentrations (1, 5 and 10 nM) or water as a control were given to leaves through the petiole as above, to measure WIPK activity (MBP phosphorylation activity) at 5, 15 and 30 minutes. As a result, as shown in FIG. 2B, the induction of WIPK activity was observed at 5 minutes, maximized at 15 minutes, and retained maximum activity at 30 minutes.

(Effects of Isolated Substance on Expression Induction of Proteinase Inhibitor II, Basic PR-1, Basic PR-2 Genes and ACO-Coding Gene)

Figure 3:
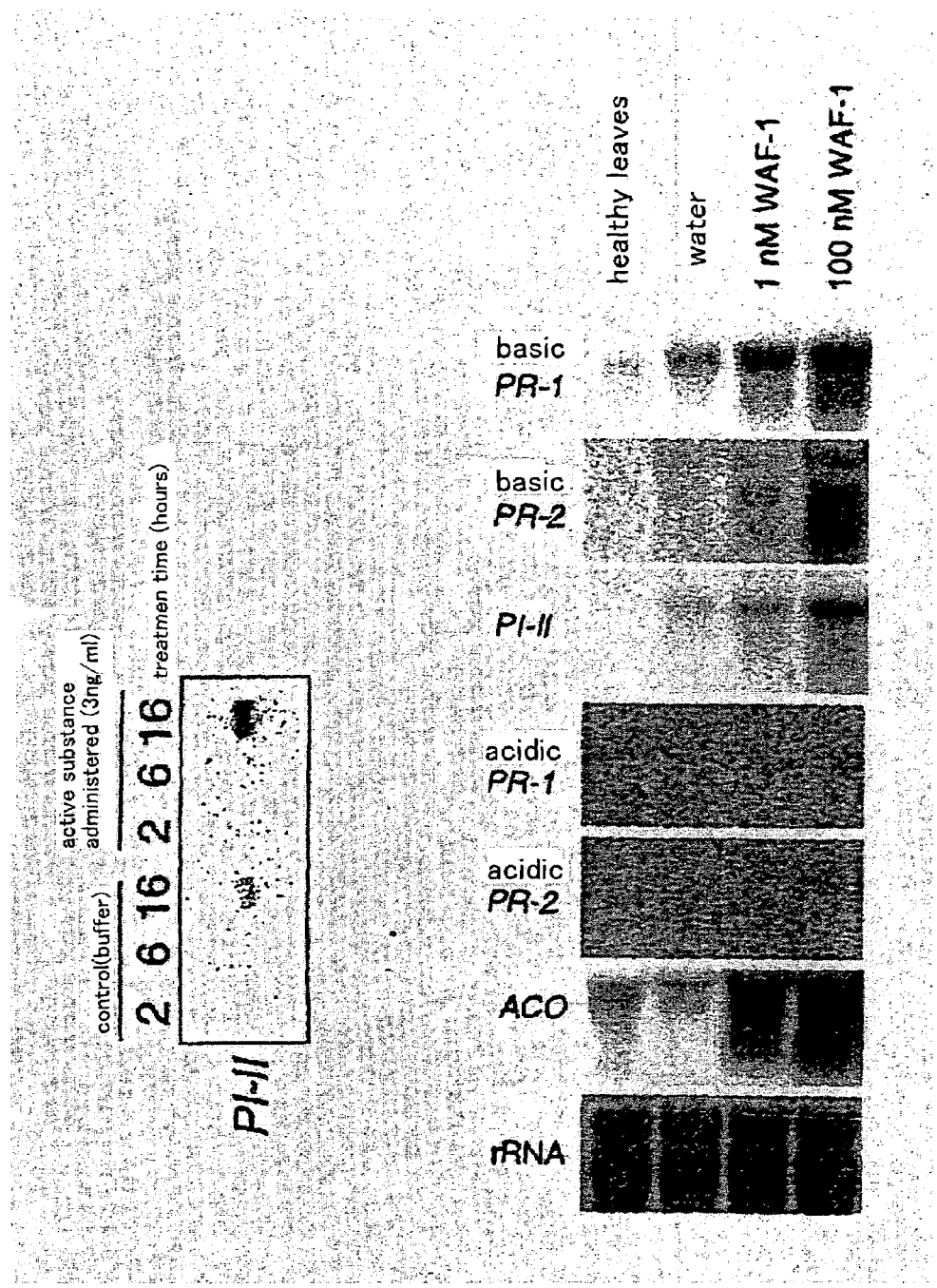
FIG. 3 shows the effect of the compound of the invention on the induction of the expression at the PI-II gene. The isolated compound at the concentrations indicated was absorbed into the subject through the petiole and a transcription product of PI-II gene is measured after a certain period of time. As control group, a buffer only was given.

The isolated substance at the concentration shown in FIG. 3 was given to leaves through the petiole to examine the accumulation of transcription products of proteinase inhibitor II gene in 2, 6 and 16 hours, resulting in the detection of accumulation at 16 hours. This amount was significantly more than that of accumulation in the control group. The accumulation of proteinase inhibitor II, basic PR-1, basic PR-2 and ACO suggests that this active substance of the invention acts as a signal transmitter of wound induction.

(Effects of isolated substance on the accumulation of JA and SA) The amounts of JA and SA in leaves treated with 100 nM WAF-1 or 1 µM WAF-1 were at the same level as those treated with water even after 3-, 6-, 12- or 24-hours culture (data not shown), suggesting that external WAF-1 does not induce any internal increase in JA or SA.

(Effects of Isolated Substance on Ethylene Accumulation)

Figure 11:
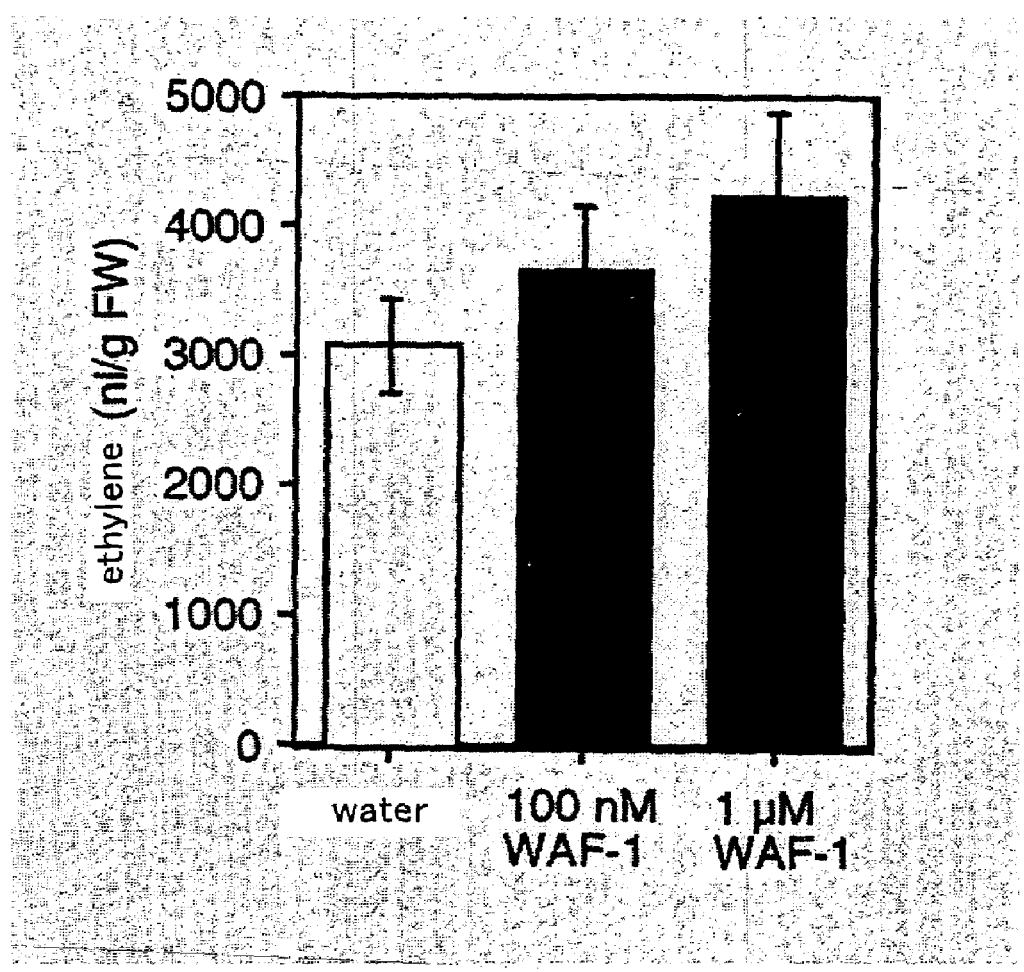
FIG. 11 shows the ethylene level released from tobacco leaves which received the compound of the invention.

As shown in the results, the levels of ethylene released from the leaves treated with 100 nM WAF-1 and 1 µM WAF-1 was 1.2 and 1.4 times higher than the leaf treated with water, respectively. The results are shown in FIG. 11.

Example 3

Identification of WIPK Activator

The above WIPK activator was analyzed using NMR and MS. For NMR analysis, JEOL JNM-A600 (JEOL. Ltd., Tokyo, Japan) was used. For MS analysis, an Automass JMS-AM SUN (JEOL. Ltd., Tokyo, Japan) was used in EI mode (70 eV)

$^1$H and $^{13}$C NMRs were assigned by the spectral data analysis on PFG-DQFCOSY, PFG-HMQC and PFG-HMB. The amount of sample was small and thus $^{13}$C NMR spectrum could not be measured. Therefore, the chemical shift level of $^{13}$C NMR was determined with 2D spectral data and assigned by comparison to the data reported on PFG-HMBC spectral data and the related Labdan diterpenoid (Jikken-Kagaku-Koza 6, *NMR (Experimental Chemistry Course 6, NMR)*, 4$^{th}$ edition, ed. The Chemical Society of Japan, Maruzen, pp 99-176; Phytochemistry 40, 1213, 1995; Phytochemistry 27, 624, 1988).

The results are shown in the following Table.

tobacco (*Nicotiana tabacum* cv. Samsun—NN) plant body was cut from the petiole, immediately put into a test tube, 10 mM Mes-NaOH (pH 5.6) solution containing isolated active substance of the invention at each concentration was added, and cultured at 24° C. 10 mM Mes-NaOH (pH 5.6) without active substance of the invention was used as a control group. In a certain amount of time, the leaves were collected and

TABLE 1

WAF-1
(11E,13E)-labda-11,13-diene-8α,15-diol

| | Proton | δ ppm | Carbon | δ ppm |
|---|---|---|---|---|
| $C_{20}C_{34}O_2$ Exact Mass: 306.26 | 1α-H | 0.86(m) | C-1 | 40.9 |
| | 1β-H | 1.38(m) | C-2 | * |
| | 2-$H_2$ | * | C-3 | 41.9 |
| | 3-$H_2$ | * | C-4 | 33.2 |
| | 5-H | 0.92(m) | C-5 | 55.7 |
| | 6α-H | 1.69(m) | C-6 | * |
| | 6β-H | 1.32(m) | C-7 | 42.0 |
| | 7α-H | 1.48(m) | C-8 | 72.0 |
| | 7β-H | 1.92(ddd, 12.7, 3.2, 3.2) | C-9 | 66.3 |
| | 9-H | 1.83(d, 10.7) | C-10 | 37.6 |
| | 10-H | 5.69(dd, 15.6, 10.7) | C-11 | 125.7 |
| | 11-H | 6.19(d, 15.6) | C-12 | 139.2 |
| | 12-H | 5.64(t, 6.8) | C-13 | 135.8 |
| | 15-$H_2$ | 4.29(dd, 6.8, 5.9) | C-14 | 129.3 |
| | 16-$H_3$ | 1.83(s) | C-15 | 59.4 |
| | | | C-16 | 12.8 |
| EI-MS m/z 288 ($M^+$—$H_2O$, 68%), 177(100), 133(60), 68), 95(66), 81(73), 69 (97), 43(0 | 17-$H_3$ | 1.20(s) | C-17 | 25.2 |
| | 18-$H_3$ | 0.89(s) | C-18 | 33.3 |
| HR-EI-MS m/z [$MH_2O$]$^+$: Found, 288.2453 | 19-$H_3$ | 0.82(s) | C-19 | 21.6 |
| Calcd. forC20H32O288.2455 | 20-$H_3$ | 0.94(s) | C-20 | 15.9 |
| | 15-OH | 1.22(t, 5.9) | | |

* Unassigned
Coupling constants (J in Hz) are given in parentheses.

As a result of the above, the structure of active substance of the invention isolated in this invention was estimated as follows:

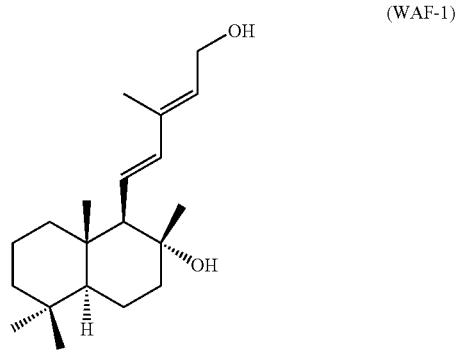

(WAF-1)

Example 4

Ascertainment of SIPK Activation Activity

Using the above WIPK activator, whether salicylate-induced protein kinase (SIPK) was activated was examined.

As an active substance, the substance isolated in Example 1 was used as a standard. The isolated substance was dissolved in dimethyl sulfoxide (DMSO) and diluted to adequate concentration (0.3, 1.5 and 3 ng/ml) with 10 mM Mes-NaOH (pH 5.6). If it was used in an assay, the DMSO concentration was kept below 0.1%. Superior healthy leaves of 50-day-old immediately frozen in liquid nitrogen to measure the SIPK activity. The measurement was conducted as follows:

Crude protein of 50 μg and anti-SIPK antibody were reacted and the myelin basic protein (MBP) phosphorylation activity of SIPK in the resultant immune complex was measured.

(Results)

(Effects of Isolated Substance on the Induction of SIPK Activity)

Figure 4:
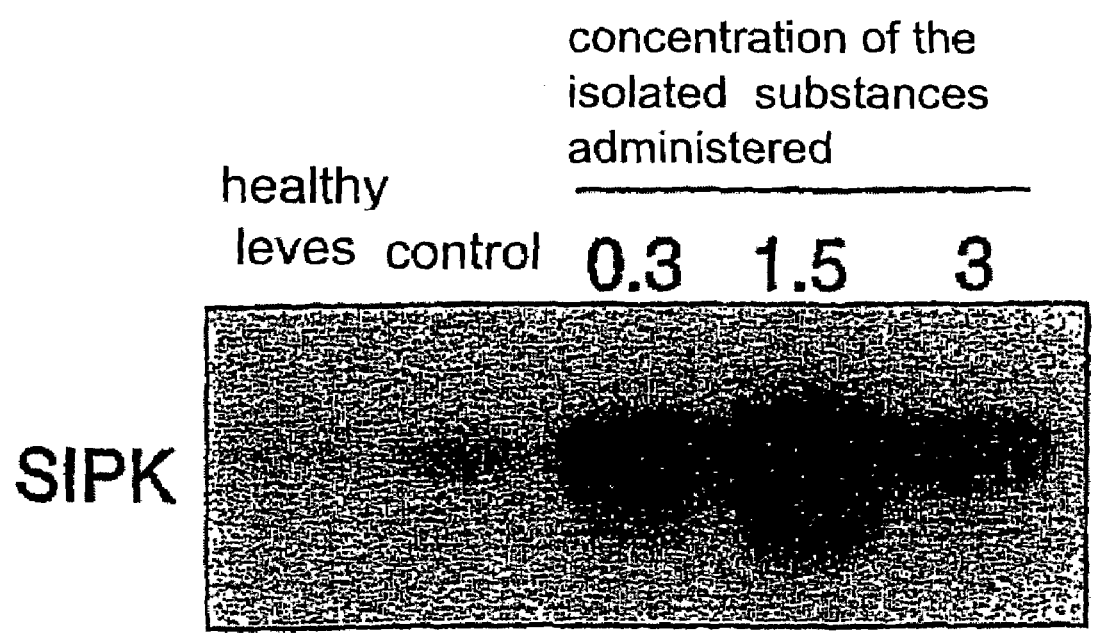
FIG. 4 shows the effect of the compound of the invention on the induction of SIPK activity. The isolated compound at the concentrations indicated was absorbed into the subject through the petiole and SIPK activity was measured after 15 minutes. As a control group, a buffer only was given. Also, as another control (healthy leaves), leaves were cut from the tobacco plant body and were subjected to SIPK activity measurement immediately.

The isolated substance at each concentration shown in FIG. 4 was given to a leaf through the petiole to measure the SIPK activity in 15 minutes, resulting in the induction of SIPK activity at any concentration. In the control group, little activity was observed.

Therefore, it became clear that the isolated substance that induces WIPK activity had the activity to induce SIPK activity also.

Natural isolated substances at certain concentrations (1, 5 and 10 nM) or water as a control were then given to leaves through the petiole to measure SIPK activity (MBP phosphorylation activity) in 5, 15 and 30 minutes. As a result, as shown in FIG. 2B, it was found that the induction of SIPK activity was already maximized at 15 minutes as shown for WIPK activity.

Therefore, it was indicated that the isolated substance that induces WIPK activity also had the activity to induce WIPK activity and to induce SIPK activity in an extremely rapid, probably commom, mechanism.

Example 5
Synthesis of WIPK Activator and Ascertainment of the Effects of the Synthetic Substance
To ascertain whether the substance having the structural formula as shown above has WIPK activation activity, a compound having the same structure was synthesized. The synthetic scheme is shown below:
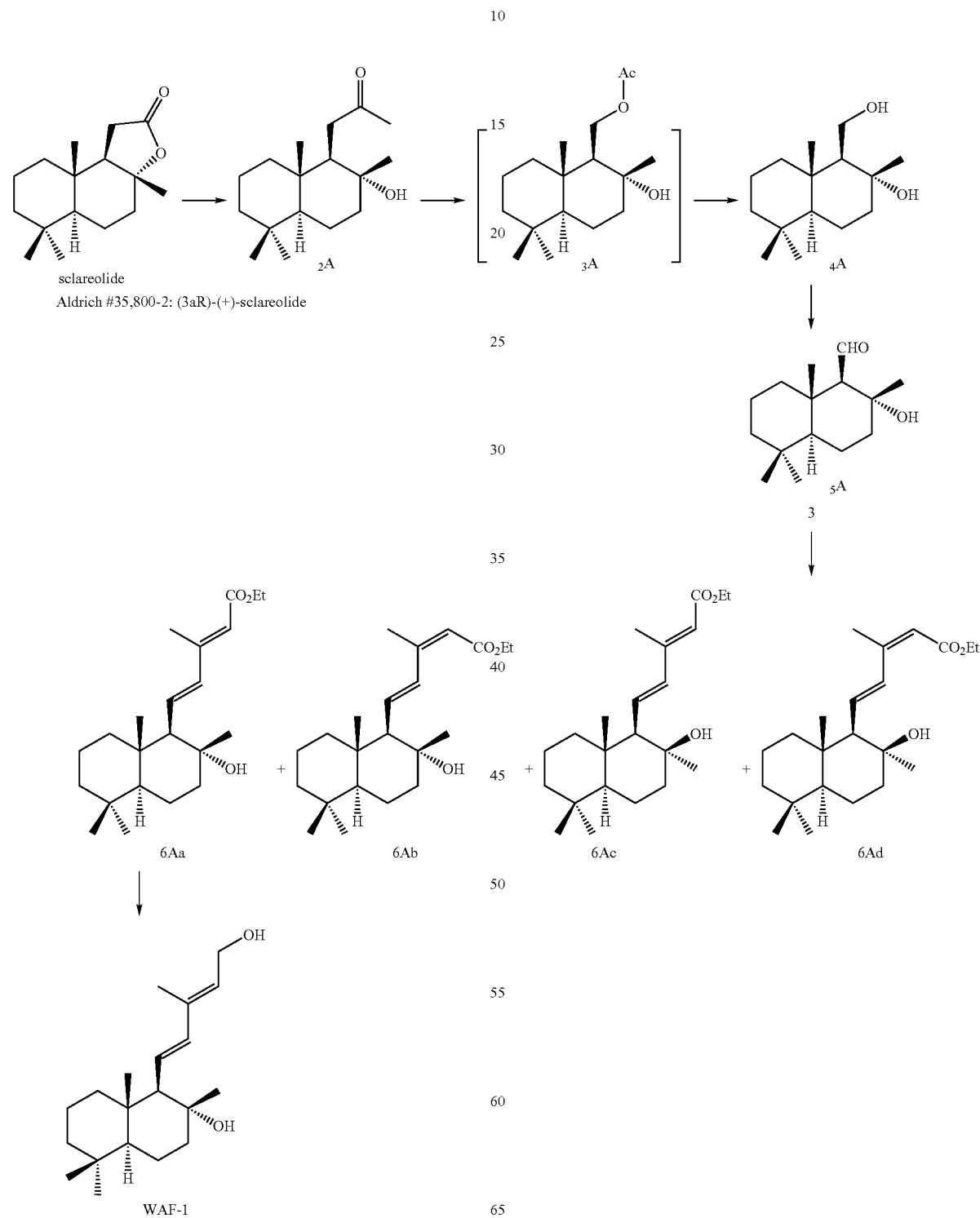

(Intermediate 2A)

Commercial sclareolide having the following structural formula:

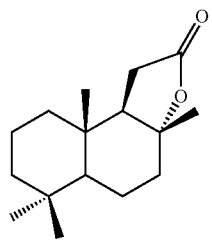

(5.0 g, 20.0 mmol) was dissolved in anhydrous Et$_2$O (150 mL), followed by dropwise addition of 1.14 M Et$_2$O (19.3 ml, 22.0 mmol) of MeLi for 10-15 minutes under nitrogen airflow with ice-cold stirring. After stirring at the same temperature for 30 minutes, 10% H$_2$SO$_4$ (25 ml) was added to the mixture solution, and stirred for 5 minutes to extract the reaction mixture with Et$_2$O. The organic layer was washed with 1% aqueous NaOH solution, water and saturated brine, progressively, and dried over Na$_2$SO$_4$. The solvent was removed under reduced pressure and the resulting residue was chromatographed over silica gel to abtain an intermediate 2A (4.8 g, 90%) from the elution with hexane-Et$_2$O (3:2) (colourless acicular, melting point {mp} 64-65° C. {hexane}).

$^1$H-NMR δH (300 MHz) 0.79 (2×3H, s), 0.88 (3H, s), 1.11 (3H, S, >C(OH)CH$_3$), 2.20 (3H, S, —C(O)CH3), 2.44 (1H, dd, J=17.5 and 4.4 Hz, 11-H), 2.54 (1H, dd, J=17.5 and 5.6 Hz, 11-H).

$^{13}$C-NMR δC (75 MHz) 15.62, 18.33, 20.55, 21.35, 23.06, 30.23, 33.18, 33.28, 38.26, 39.53, 41.69, 44.56, 55.80, 55.89, 73.08, 210.20.

(Intermediate 2A)

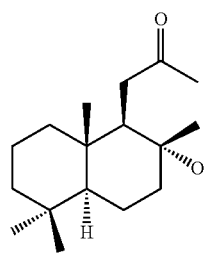

(Intermediate 4A)

Intermediate 2A (1.00 g, 3.75 mmol) was dissolved in anhydrous CH$_2$Cl$_2$ (20 ml) and-added with m-chloroperbenzoic acid (1.43 g, 8.27 mmol) under nitrogen airflow with ice-cold stirring, followed by stirring at the same temperature for 1 hour, and additionally incubated at room temperature for 5 days. After the solvent was removed, the residue was dissolved in MeOH solution (12 mL) containing 10% KOH and stirred at room temperature for 24 hours. The reaction mixture was extracted by Et$_2$O and the Et$_2$O layer was washed with saturated NaHCO$_3$ solution, water and saturated brine, progressively, and dried over Na$_2$SO$_4$. The solvent was removed under reduced pressure and the resulting residue was subjected to flash chromatography to obtain an intermediate 4A (493 mg, 55%) from the elution with hexane-AcOEt (3:1) (colourless acicular, mp 11.8-119° C. {Et$_2$O-hexane}).

$^1$H-NMR δH (300 MHz) 0.79 (2×3H, s), 0.88 (3H, s), 1.35 (3H, s, >C(OH)CH3), 3.91 (2H, —CH2-).

$^{13}$C-NMR "C (75 MHz) 15.03, 18.60, 20.18, 21.62, 24.29, 33.27, 33.55, 37.52, 40.00, 41.69, 44.45, 55.92, 60.50, 61.10, 75.07.

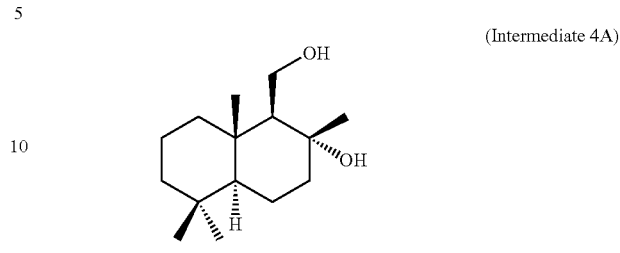

(Intermediate 4A)

(Intermediate 5A)

Intermediate 4A (199 mg, 0.829 mmol), N-methylmorpholine N-oxide (292 mg, 2.50 mmol), and 4A molecular sieve (524 mg) were suspended in anhydrous CH$_2$Cl$_2$ (5 ml) and added with perruthenate tetrapropylammonium (29 mg, 0.083 mmol) under nitrogen airflow with ice-cold stirring, followed by stirring at the same temperature for 10 minutes, additionally stirred at room temperature for 25 minutes. To the reaction mixture, Et$_2$O (20 ml) was added and stirred, followed by filtration with silica gel. After the filtrate was concentrated, it was subjected to flash chromatography to obtain an intermediate 5A (126 mg, 64%) from the elution with hexane-Et$_2$O (10:1) (colourless wax solid).

$^1$H-NMR δH (300 MHz) 0.84 (3H, s), 0.90 (3H, s), 1.12 (3H, s), 1.39 (3H, s, >C(OH)CH$_3$), 2.08 (1H, d, J1.4 Hz, 9-H), 10.03 (1H, d, J1.4 Hz, —CHO).

$^{13}$C-NMR δC (75 MHz) 17.53, 18.14, 19.85, 21.33, 25.28, 33.22, 33.30, 37.34, 39.77, 41.59, 42.67, 55.14, 71.26, 72.77, 208.16.

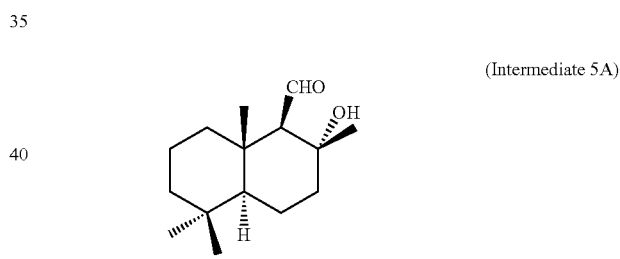

(Intermediate 5A)

(Intermediate 6A)

NaNH$_2$ (30.5 mg, 0.781 mmol) was suspended in anhydrous THF (4.1 ml), followed by dropwise addition of 3-ethoxycarbonyl-2-methyl-prop-2-enylphosphonate (0.20 ml, 0.824 mmol)

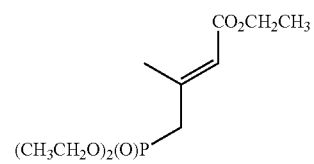

under nitrogen airflow with ice-cold stirring, and stirred at the same temperature for 20 minutes. The reaction mixture was cooled to −78° C., followed by the dropwise addition of a solution of intermediate 5A (61.1 mg, 0.256 mmol) in THF (4.1 ml), stirred at −50° C. for 41 hours, then back to room temperature, water added, and extraction with Et$_2$O. The Et$_2$O layer was washed with water and saturated brine, progressively, and dried over Na₂SO₄. The solvent was removed under reduced pressure and a resulting residue was subjected to flash chromatography to abtain the mixture of intermediates 6Ac and 6Ad (24 mg) and that of 6Aa and 6Ab (64 mg) from the elution of hexane-AcOEt (10:1) solution. For the mixture of intermediates 6Aa and 6Ab, intermediates 6Aa (8.9 mg, 10%) and 6Ab (52 mg, 59%) were abtained by high performance liquid chromatography [elution solvent: hexane-AcOEt (5:1), elution rate: 10 ml/min], while, for the mixture of intermediates 6Ac and 6Ad, 6Ad (4.7 mg, 5.3%) and 6Ac (17 mg, 19%) were obtained from the elution site of exane-AcOEt (10:1) by additional flash chromatography.

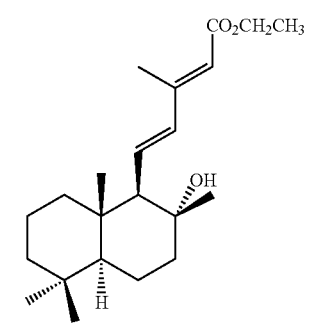

6Aa

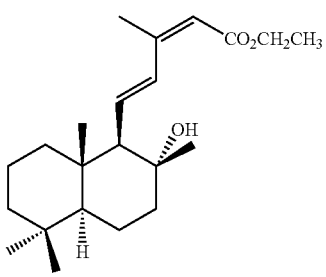

6Ab

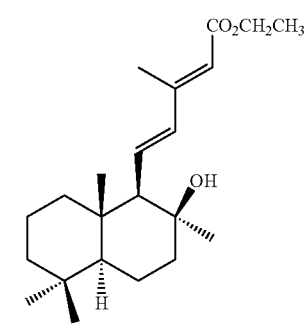

6Ac

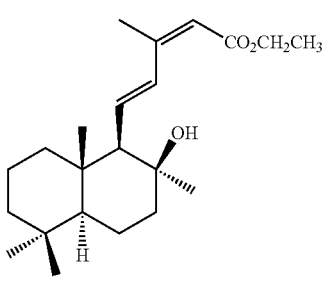

6Ad

The measured data on each intermediate of 6Aa-6Ad is shown below:

(Intermediate 6Aa)

Colourless Wax Solid $^1$H-NMR δH (300 MHz) 0.84 (3H, s), 0.89 (3H, s), 0.96 (3H, s) 1.23 (3H, s, 17-H3), 1.28 (3H, t, J7.1 Hz, —OCH2-CH3), 2.30 (3H, d, J1.0 Hz, 16-H3), 4.17 (2H, q, J7.1 Hz, —OCH2-CH3), 5.74 (1H, s, 14-H), 6.12 (1H, dd, J15.4 and 9.5 Hz, 11-H), 6.22 (1H, d, J15.4 Hz, 12-H).

$^{13}$C-NMR δC (75 MHz) 14.07, 14.33, 15.98, 21.59, 25.23 and 33.38 (C-16, -17, -18, -19 and -20, and —OCH2-CH3) 18.40, 20.09, 40.96, 41.88 and 42.33 (C-1, -2, -3, -6 and -7), 33.32 and 37.84 (C-4 and -10), 55.74 and 66.48 (C-5 and -9), 59.72 (—OCH2-CH3), 72.21 (C-8), 119.07, 133.02 and 138.77 (C-11, -12 and -14), 151.35 (C-13), 167.11 (C-15).

(Intermediate 6Ab)

Colourless Viscous-oily Substance $^1$H-NMR δH (300 MHz) 0.82 (3H, s), 0.89 (3H, s), 0.95 (3H, s), 1.22 (3H, s, 17-H3), 1.27 (3H, t, J7.1 Hz, —OCH2-CH3), 2.02 (3H, d, J1.0 Hz, 16-H3), 4.16 (2H, q, J7.1 Hz, —OCH2-CH3), 5.66 (1H, s, 14-H), 6.10 (1H, dd, J15.7 and 10.3 Hz, 11-H), 7.58 (1H, d, J15.7 Hz, 12-H).

$^{13}$C-NMR δC (75 MHz) 14.32, 16.02, 21.33, 21.59, 25.01 and 33.39 (C-16, -17, -18, -19 and -20, and —OCH2-CH3) 18.40, 20.14, 40.91, 41.89 and 42.64 (C-1, -2, -3, -6 and -7), 33.31 and 37.82 (C-4 and -10), 55.69 and 66.62 (C-5 and -9), 59.73 (—OCH2-CH3), 72.21 (C-8), 117.01, 132.93 and 134.29 (C-11, -12 and -14), 150.07 (C-13), 166.15 (C-15).

(Intermediate 6Ac)

Colourless acicular, mp 123-126° C. (hexane)

$^1$H-NMR δH (300 MHz) 0.86 (3H, s), 0.89 (3H, s), 1.04 (3H, s), 1.07 (3H, s), 1.28 (3H, t, J7.1 Hz, —OCH2-CH3), 2.31 (3H, d, J1.0 Hz, 16-H3), 4.17 (2H, q, J7.1 Hz, —OCH2-CH3), 5.71 (1H, s, 14-H), 6.05 (1H, d, J15.6 Hz, 12-H), 6.28 (1H, dd, J15.6 and 10.0 Hz, 11-H).

$^{13}$C-NMR δC (75 MHz) 14.11, 14.35, 16.01, 21.80, 31.62 and 33.53 (C-16, -17, -18, -19 and -20, and —OCH2-CH3), 18.20, 18.31, 40.75, 42.01 and 42.39 (C-1, -2, -3, -6 and -7), 33.43 and 38.25 (C-4 and -10), 55.57 and 63.65 (C-5 and -9), 59.61 (—OCH2-CH3), 72.27 (C-8), 118.08, 134.66 and 137.38 (C-11, -12 and -14), 152.26 (C-13), 167.27 (C-15).

(Intermediate 6Ad)

Colourless acicular, mp 115-117° C. (hexane)

$^1$H-NMR δH (300 MHz) 0.86 (3H, s), 0.88 (3H, s), 1.06 (3H, s), 1.07 (3H, s), 1.28 (3H, t, J7.1 Hz, —OCH2-CH3), 2.03 (3H, d, J1.1 Hz, 16-H3), 4.16 (2H, q, J7.1 Hz, —OCH2-CH3), 5.63 (1H, s, 14-H), 6.28 (1H, dd, J15.9 and 10.1 Hz, 11-H), 7.52 (1H, d, J15.9 Hz, 12-H).

$^{13}$C-NMR δC (75 MHz) 14.33, 16.07, 21.30, 21.79, 31.69 and 33.52 (C-16, -17, -18, -19 and -20, and —OCH2-CH3) 18.20, 18.32, 40.63, 41.98 and 42.41 (C-1, -2, -3, -6 and -7), 33.41 and 38.14 (C-4 and -10), 55.50 and 63.67 (C-5 and -9), 59.56 (—OCH2-CH3), 72.38 (C-8), 115.97, 131.57 and 136.17 (C-11, -12 and -14), 151.03 (C-13), 166.40 (C-15).

(Synthesis of WAF-1)

Then, of the above compounds, 6Aa-6Ad,

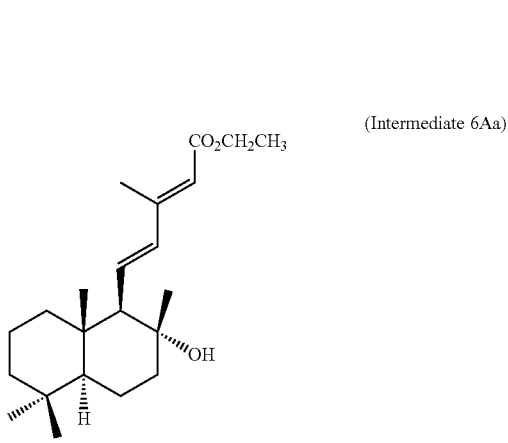
(Intermediate 6Aa)

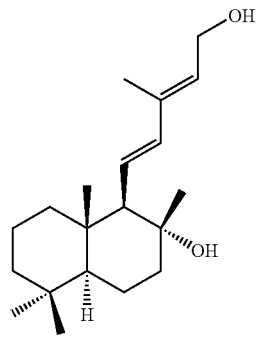
(WAF-1)

(10 mg, 0.029 mmol) was dissolved in anhydrous $CH_2Cl_2$ (0.5 ml), followed by dropwise addition of 1.0 M $CH_2Cl_2$ solution of diisobutylaluminum hydride (0.20 ml, 0.20 mmol) in nitrogen airflow at −78° C. under stirring. After stirring at the same temperature for 30 minutes, and removal of the refrigerant, the mixed solution was stirred for 30 minutes with a gradual increase to room temperature. While on ice, AcOEt (0.5 ml), $CH_2Cl_2$ (5 ml), 0.5 M aqueous solution of sodium potassium tartrate (1.1 ml) was added tp the reaction mixture, stirred at room temperature for 15 minutes, and extracted with Et. The organic layer was washed with water and saturated brine, progressively, and dried over $Na_2SO_4$. The solvent was removed under reduced pressure and the resulting residue was subjected to flash chromatography to abtain WAF-1 (9.0 mg, 100%) from the elution site of hexane-AcOEt (1:1) (colourless viscous-oily substance).

$^1$H-NMR δH (600 MHz) 0.82 (3H, s, 19-H3), 0.85 (1H, m, 1a-H), 0.88 (3H, s, 18-H3), 0.93 (1H, m, 5-H), 0.94 (3H, s, 20-H3), 1.13 (1H, m, 3a-H), 1.20 (3H, s, 17-H3), 1.32 (1H, m, 6b-H), 1.38 (1H, m, 1b-H), 1.38 (1H, m, 2a-H), 1.38 (1H, m, 3b-H), 1.48 (1H, ddd, J12.7, 12.7 and 3.3 Hz, 7a-H), 1.56 (1H, m, 2b-H), 1.69 (1H, m, 6a-H), 1.83 (1H, d, J10.3 Hz, 9-H), 1.83 (3H, s, 16-H3), 1.92 (1H, ddd, J12.7, 3.1 and 3.1 Hz, 7a-H), 4.29 (2H, d, J6.8 Hz, 15-H2), 5.64 (1H, t, J6.8 Hz, 14-H), 5.69 (1H, dd, J15.6 and 10.3 Hz, 11-H), 6.19 (1H, d, J15.6 Hz, 12-H).

$^{13}$C-NMR δC (150 MHz) 12.85 (C-16), 15.92 (C-20), 18.44 (C-2), 20.07 (C-6), 21.60 (C-19), 25.23 (C-17), 33.32 (C-4) 33.40 (C-18), 37.66 (C-10), 40.91 (C-1), 41.95 (C-3), 42.03 (C-7), 55.84 (C-5), 59.31 (C-15), 66.38 (C-9), 72.00 (C-8), 125.71 (C-11), 129.46 (C-14), 135.94 (C-13), 139.44 (C-12).

EI-MS m/z288 ($M^+$-H2O, 68%), 177 (100), 133 (60), 109 (68), 95 (66), 81 (73), 69 (97), 43 (63). HR-EI-MSm/z [M-H2O]$^+$: Measured value, 288.2453. Calculated value about $C_{20}H_{32}O$, 288.2455.

It was confirmed that this compound had the same structure as natural substances of the invention.

(Ascertainment of WIPK Activation Activity of the Synthetic Substance)

Figure 5:
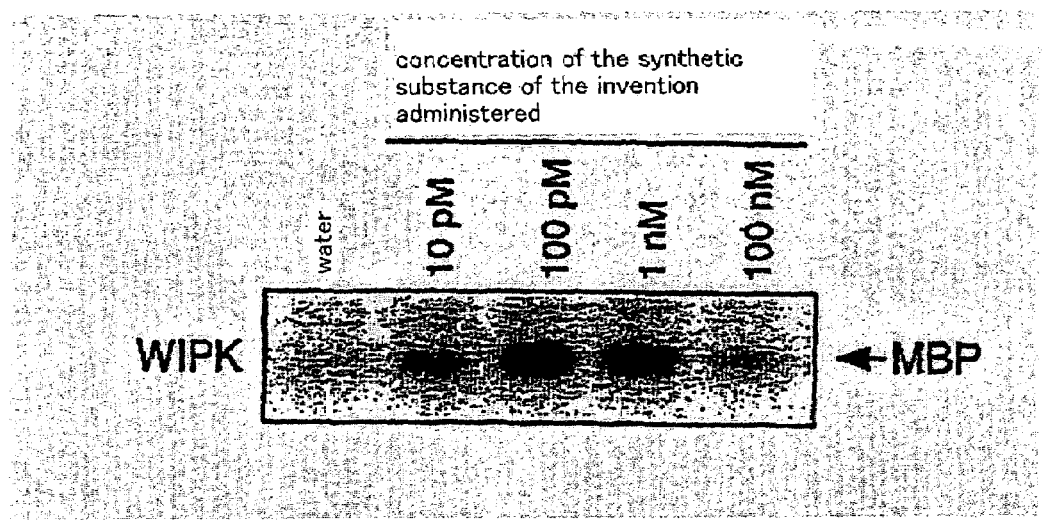
FIG. 5 shows the effect of the synthesized compound of the invention on the induction of WIPK activity. MBP indicates the intensity of MBP phosphorylation.

Using the synthetic substance thus synthesized, the WIPK activity measurement test was conducted as stated in Example 1. The results are shown in FIG. 5.

(Ascertainment of SIPK Activation Activity of the Synthetic Substance)

Figure 6:
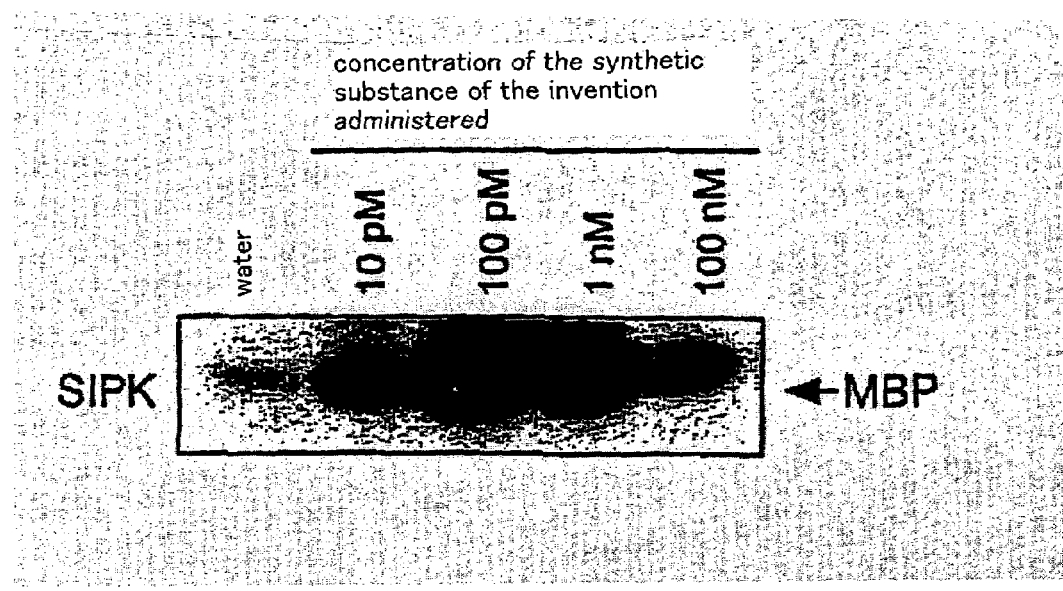
FIG. 6 shows the effect of the synthesized compound of the invention on the induction of SIPK activity. MBP indicates the intensity of MBP phosphorylation.

Using the synthetic substance thus synthesized, the SIPK activity measurement test was conducted as stated in Example 4. The results are shown in FIG. 6.

(Ascertainment of WIPK and SIPK Activities of Natural Substance of the Invention)

Figure 7:
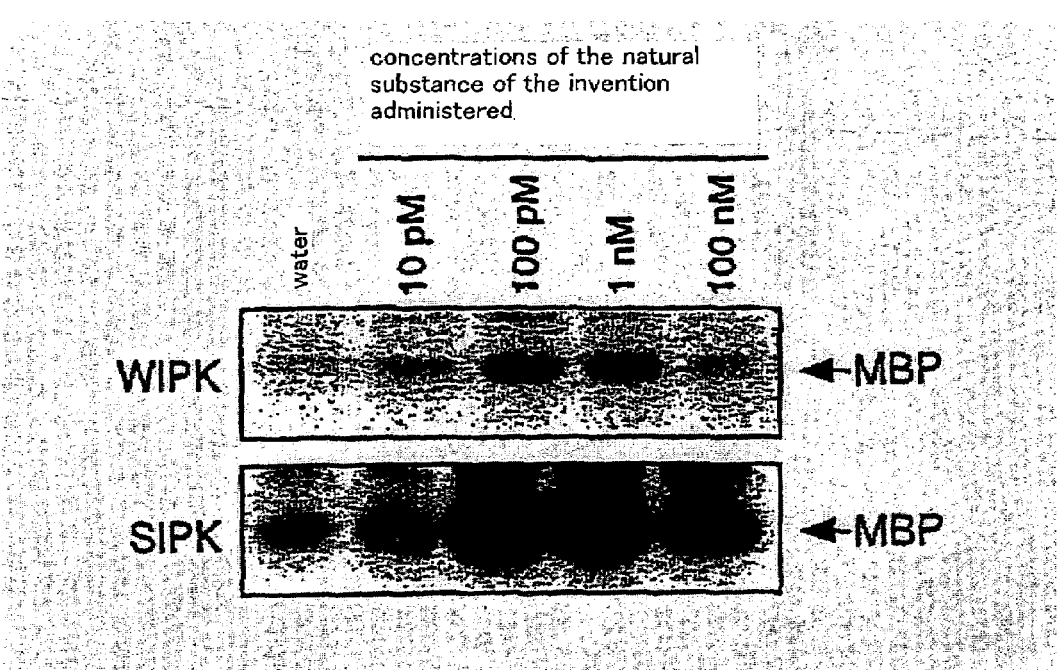
FIG. 7 shows an examination in WIPK and SIPK activities of the natural active substance of the invention.

Using natural isolated substances, preparations at concentrations of 10 and 100 pM, and 1 and 100 nM were prepared and these natural preparations or water were penetrated into tobacco leaf disks, followed by sampling at 30 minutes after treatment, to measure the MBP phosphorylation activity of WIPK and SIPK as described above. The results are shown in FIG. 7.

(Results)

As these results show, in natural isolated substances, it seems to be that the activation of WIPK and SIPK is significant at higher concentrations than 10 pM and reaches a maximum at a concentration between 100 pM and 1 nM. Synthetic WAF-1 also showed a similar aspect.

Therefore, it was ascertained that the synthetic preparations and the natural isolated substance of the present invention produced effects at the same concentrations.

Example 6

Accumulation of an Endogenous Amount of Active Substance of the Invention After TMV Infection and Wounding The accumulation of an endogenous amount of active substance of the invention according to this invention after TMV infection and wound was ascertained.

(Quantification Method for Active Substance of the Invention)

2 g of a leaf tissue was ground with 20 ml cold 80% (v/v) methanol in a Polytron and allowed to stand at 4° C. for 1 hour for extraction. The extract was centrifuged at 10,000×g for 10 minutes. The precipitate was suspended in 10 ml cold 80% (v/v) methanol and centrifuged at 10,000×g for 10 minutes to collect the supernatant. The resultant two supernatants were collected and the water phase concentrated to at 35° C. under reduced pressure with a rotary evaporator. The resultant water phase was adjusted to pH 7.5 with 1M phosphate buffer and fractionated with the same amount of ethyl acetate three times. The supernatant ethyl acetate layer was dehydrated with anhydrous sodium sulfate and concentrated to dryness at 35° C. under reduced pressure with a rotary evaporator. The dried substance was dissolved in 3 ml 80% (v/v) methanol and passed through a C18 Sep-Pak cartridge column (Waters, the U.S.A.) equilibrated with 80% (v/v) methanol inadvance. The flow-through fractions were collected and concentrated to dryness at 35° C. under reduced pressure with a rotary evaporator. The concentrated residue was dissolved in 80% (v/v) methanol and the solution was subjected to high performance liquid chromatography (LiChrospher 100RP-18.5-μm particle diameter, 4 mm internal diameter, 25 cm length, Hewlett Packard). Elution was conducted with methanol solution (methanol:water=4:1) (v/v) at 1 ml/min of flow rate. The solution eluted from 11 to 16.5 minutes retention time was collected. After this the solution collected was concentrated to dryness, the resultant residue was dissolved in 200 μl acetonitrile solution (acetonitrile:water=9:8 (v/v)), one-tenth amount of which was subjected to the above described high performance liquid chromatography. The elution was conducted-with acetonitrile solution (acetonyl:water=9:8 (v/v)) at 1 ml/min of flow rate. Ultraviolet absorption was monitored at the constant-wavelength of 238 nm to detect WAF-1. To obtain the recovery rate of active substance of the invention in extraction and purification procedures, 300 ng Labdan a was added as an internal standard in the initial process of the extraction procedure.

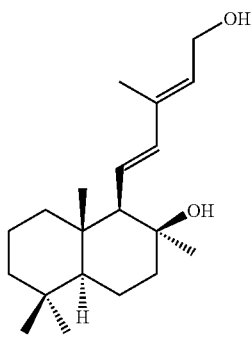

The retention times of the active substance of the invention and Labdan a were 24.5 and 29.5 minutes, respectively. The endogenous amount of active substance of the invention was calculated with the calibration curve produced by a known amount of active substance of the invention. All data was obtained by correction to the loss based on the recovery rate of active substance of the invention in extraction and purification procedures (65-75%).

Labdan a was produced as follows: Specifically, it was abtained by reduction of intermediate 6Ac with diisobutylaluminum hydride.

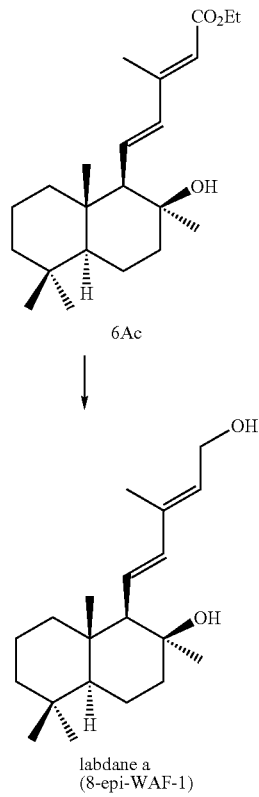

labdane a
(8-epi-WAF-1)

In FIG. 7, the data was shown to produce a calibration curve of the compound of this invention, which was isolated from tobacco. As stated above, in the experiment to produce a calibration curve, tobacco leaf disks were penetrated with water and natural substance of the invention at each concentration, followed by sampling at 30 minutes after treatment, to measure the MBP phosphorylation activity of WIPK and SIPK as stated above.

Labdan a is a product obtained in a synthetic process of active substance of the invention, showing the chromatography behavior similar to that of the active substance of the invention, but not present in the tobacco plant body. Based on these properties, Labdan a was used as an internal standard.

(Accumulation of the Endogenous Amount of Active Substance of this Invention After the Change from 20 to 30° C.)

Tobacco leaves were inoculated with TMV (10 μg/ml) or buffer (mock inoculation) was inoculated tobacco leaves. After inoculation, leaf disks of 3 cm in diameter were stamped out of the inoculated leaves and put into a transparent plastic box spread with filter papers moisten with distilled water, which was cultured in an incubator at 30° C. for 48 hours, then transferred to another incubator at 20° C. to induce a hypersensitive reaction, followed by sampling of the disks over time to be used in the quantification for active substance of the invention.

Figure 8:
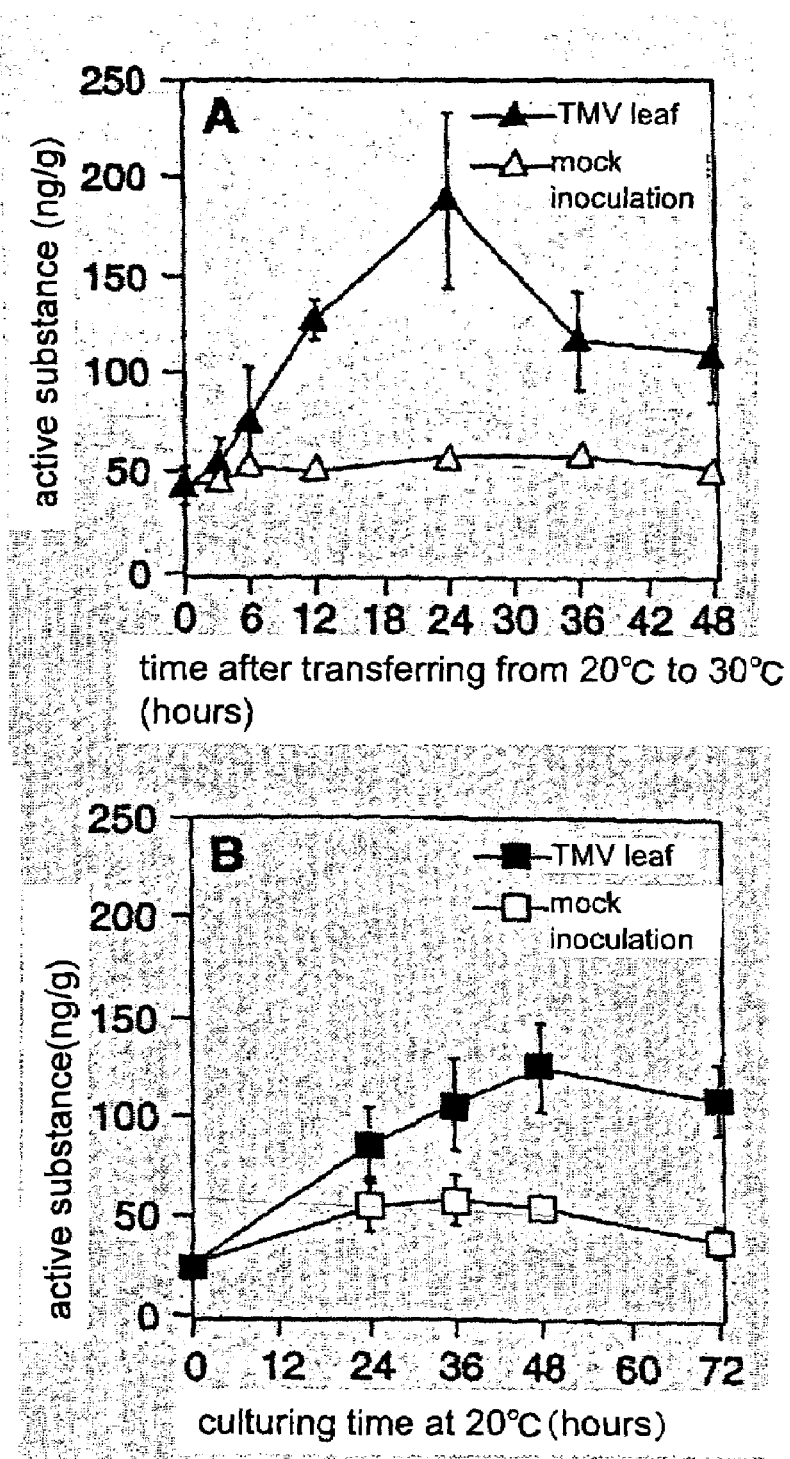
FIG. 8A shows an endogenous accumulation of the active substance of the invention after transfer from 20° C. to 30° C.
FIG. 8B shows an endogenous accumulation of the active substance of the invention after initiating incubation at 20° C.

The results are shown in FIG. 8A. Units are nano grams (ng) active substance of the invention per 1 g fresh weight of leaf. Each data point indicates mean ± standard deviation of measurements in triplicate.

(Accumulation of the Endogenous Amount of Active Substance of the Invention After the Start of Culture at 20° C.)

Tobacco leaves were inoculated with TMV (2 μg/ml) or buffer (mock inoculation) was inoculated. After inoculation, leaf disks of 3 cm in diameter were stamped out of the inoculated leaves and were put into a transparent plastic box spread with filter papers moisten with distilled water, which was cultured in an incubator at 20° C., followed by sampling of the disks over time to be used in the quantification for active substance of the invention. The results are shown in FIG. 8B. The units are nano grams (ng) active substance of the invention per 1 g fresh weight of leaf. Each data point indicates mean± standard deviation of measurements in triplicate.

(Accumulation of the Endogenous Amount of Active Substance of the Invention After Wounding)

Figure 9:
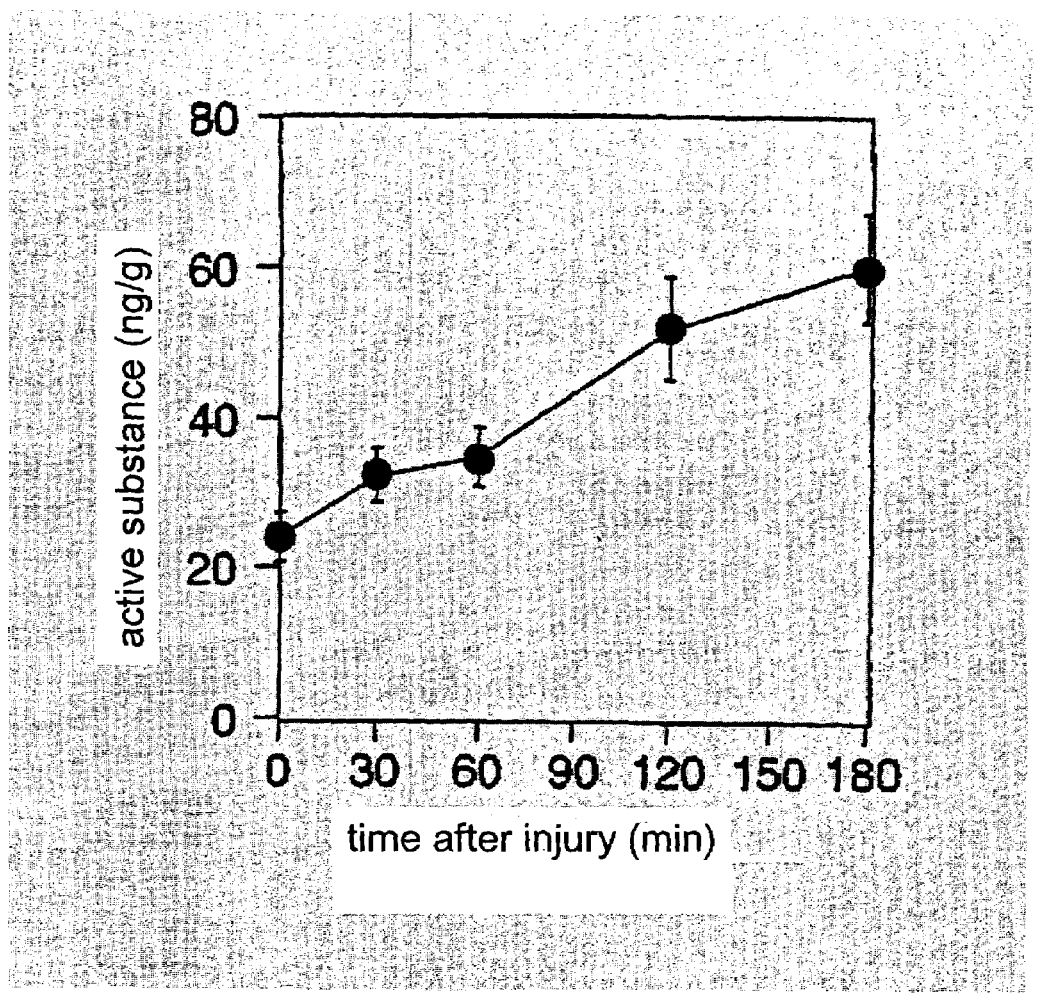
FIG. 9 shows an endogenous accumulation of the active substance of the invention after wounding.

Tobacco leaves were cut to the size of about 5-mm-square with a razor. The leaf segments sampled over time were used for the quantification of active substance of the invention. The results are shown in FIG. 9. The units are nano grams (ng) active substance of the invention per 1 g fresh weight of leaf. Each data point indicates mean ± standard deviation of measurements in triplicate.

(Results and Discussion)

WIPK activating substance was isolated from the tobacco leaves in which a hypersensitive reaction was induced. Hypersensitive reaction is a typical example of the pathogenesis resistance reaction of plants, in which the plant sites infected with the pathogen positively die, and confines pathogens, resulting in necrosis lesion, followed by inhibition of the infection spreading to non-infected sites. It is thoght that resistant genes responding to pathogens in plants are involved in the hypersensitive reaction, for example, in the case of tobacco resistance to TMV, such an example includes TMV-resistant gene N.

It is known that WIPK is activated at the initial stage of the hypersensitive reaction to TMV infection. Therefore, it was investigated whether the content of WIPK activating substance of this invention changed in the hypersensitive reaction. The hypersensitive reaction to TMV infection of tobacco with N gene is temperature sensitivity so that it dose not occur at 28° C. or higher when N genes are not working, while it does occur at 24° C. or lower where N genes are working. Using this characteristic, in this Example, TMV-infected leaves of Samsun NN tobacco (which has N gene) were cultured at 30° C., then at 20° C., to induce the hypersensitive reaction.

When TMV-inoculated leaves cultured at 30° C. for 48 hours were shifted to 20° C., the content of WIPK activating substance began to increase at 3 hours as shown in FIG. 8A and reached a maximum at 24 hours. The content of this substance was 43±9 and 189±45 ng/g in fresh weight (FW) in 0 and 24 hours, respectively. The first increase occurred before WIPK activation (occurred 4 hours after the shift to 20° C.) and the appearance of necrotic lesions (occurred 8 hours after the shift to 20° C.). In mock-inoculated leaves, there was no correnponding increase (FIG. 8A).

Similarly, when TMV-inoculated leaves were cultured at 20° C. shortly after inoculation, an increase in content of WIPK active substance of the invention was observed (FIG. 8B; 26±6 ng/g FW shortly after inoculation and 126±22 ng/g FW at 48 hours). The increase in content was seen 24 hours earlier than the 30 to 32 hours when necrotic lesion appeared. A transient increase in the content of WIPK activating substance was also observed in mock-inoculated leaves continuous cultured at 20° C., suggesting that physical wounding induces an increase in content of the substance in this invention in vivo To ascertain whether wounding induces an increase in WIPK activating substance, the leaves were injured physically, followed by monitoring of the quantitative variation of the substance. As a result, as shown in FIG. 9, the content of WIPK activating substance increased by 1.3-fold at 30 minutes after wounding (in healthy plant leaves, 24 ng/g FW and 32±4 ng/g FW in 30 minutes), to almost about 3-fold in 180 minutes (60±7 ng/g FW) suggesting that WIPK activating substance also immediately responds to physical stress.

Example 7

Transcription Factor Regulation by WAF-1

To elucidate the role of WAF-1 in HR signaling pathway and the wound signaling pathway, the effects of WAF-1 on gene expression induced by HR and wounding were investigated.

As a result, the investors found that WAF-1 activated tobacco WIZZ gene encoding WRKY type transcription factor. The results are shown below:

WIZZ is a factor whose expression was induced 10 minutes after wounding (Hara K, et al., MGG, 263, 30 (2000)) and it is known that it can be detected before TMV necrotic lesion (Yoda H, et al. MGG 267, 154 (2002)).

The transition in expression of the WIZZ transcript after stimulation with WAF-1 in this invention was ascertained using the following method. Leaf disks stamped out of tobacco leaves were penetrated with 1 nM WAF-1 solution or water and collected at 30 minutes after penetrance to be used for total RNA extraction. Total RNA extraction followed the method described in Seo et al. Plant Cell 1999, 11, 289-299. Isolated total RNA was subjected to RNA gel blotting analysis following the above procedure. A fragment, whose sequence corresponded to bases 877-1211 in the WIZZ cDNA (335 bp) was amplified, and used as a probe. As an internal standard probe, actin cDNA (described in Seo et al. 2000 12, 917-932) was also used. An RNA gel blot membrane containing 20 µg total RNA per lane was analized.

Figure 10:
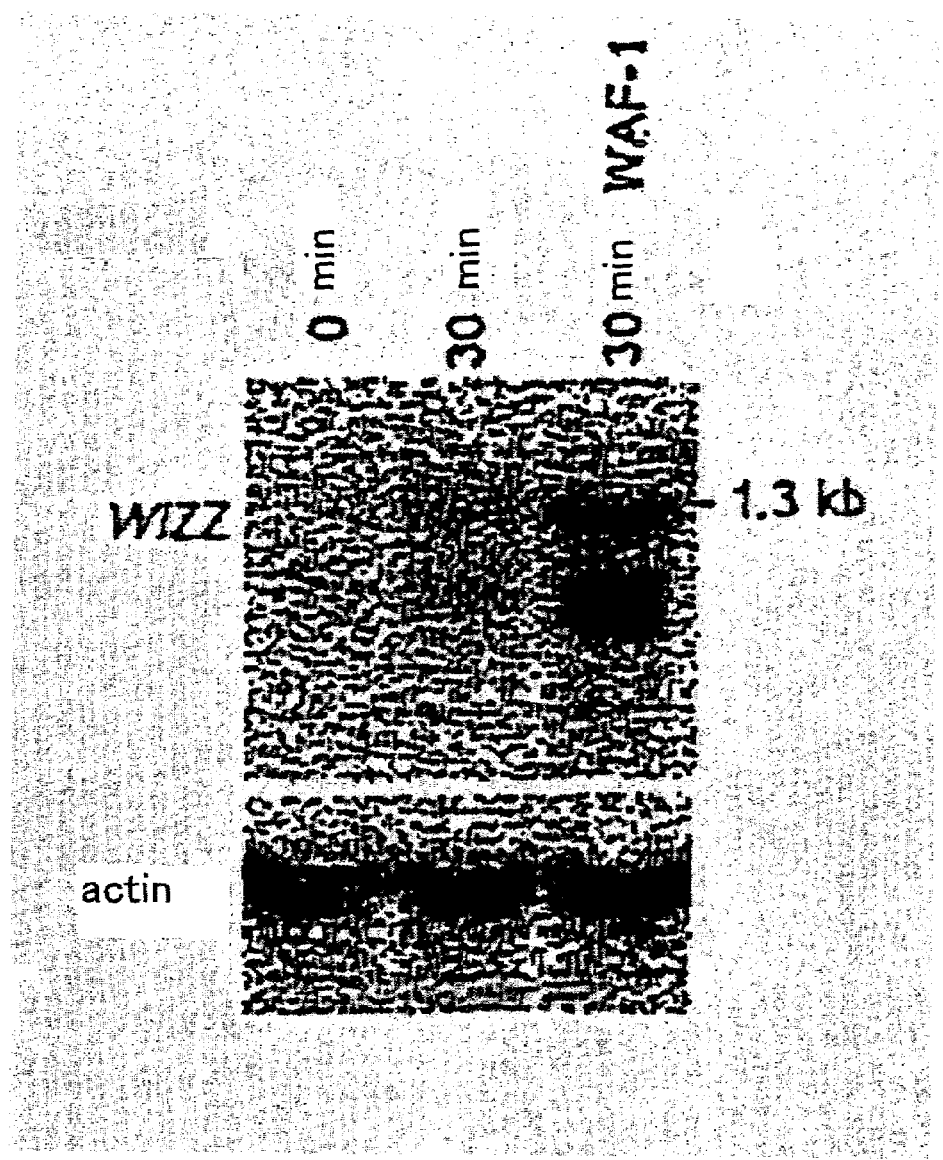
FIG. 10 shows the induction of WIZZ transcription level by the compound of the invention. WIZZ indicates the induction of WIZZ by the compound of the invention and Actin indicates the induction when using actin as control (Control (0 min), 30 min after treatment by water or WAF-1).

As a result, as shown in FIG. 10, the level of WIZZ transcript was higher in leaf disks impregnated with WAF-1 than in those inpregnated with water, suggesting that externally supplied WAF-1 enhanced WIZZ expression. Therefore, it was indicated that WAF-1 in this invention has a role in regulatin of the immediate response shortly after stress.

The fact that the internal WAF-1 level increases before appearance of necrotic lesions indicates that WAF-1 accumulation is the initial event of hypersensitivity cell death in TMV-infected tobacco. It seems that the induction of WIZZ gene expression by WAF-1 is mediated by WIPK and SIPK activation. In fact, AtMPK3 and AtMPK6 are orthologs of WIPK and SIPK of *Arabidopsis*, respectively, and it was reported that activation of wach of these was involved in the expression of a set of genes encoding WPKY transcription factor (Asai T, et al., Nature 415, 977 (2002)). Therefore, WAF-1 appears to be a signal compound for activation in the signaling pathway of the HR signal and the wound signal.

Labdan-type diterpene seems widely present in the plant kingdom, but the biological role is little understood. Sclareol has the following structure:

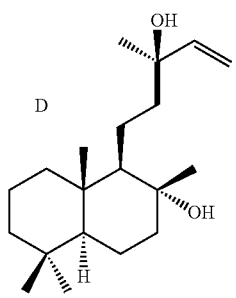

and is a main Labdan-type diterpene present in plant. Sclareol is an intimate analog of sclareolide, a starting substance of chemical synthesis of WAF-1, as stated above and is of interest in association with the invention stated in this specification.

Sclareol has various pharmacological activities. Such activities include induction of apoptosis (Dimas K, Leukemia Res. 25: 449 (2001)), fungal growth inhibition (Bailey, J. A. et al., Nature 255, 328 (1975)), and plant growth inhibition (Cutler H. G. et al., Plant Cell Physiol. 18, 711 (1977)), etc. Sclareol also induces the expression of the tobacco gene encoding ABC transporter involved in the secretion and excretion of toxic drugs (Jasinski et al. Plant Cell 13, 1095 (2001)).

It is interesting to note that sclareol constitutes 10% of the leaf surface exudates of Nicotiana glutinosa (Bailey, J. A. et al. , J. Gen. Microbiol. 85, 57 (1974)).

The inventors put tobacco leaves under reduced pressure, then returned the tobacco leaves back to atmospheric pressure, centrifuged them after water infiltration, followed by collection of the supernatant, to investigate the localization in tissue of WAF-1, resulting in collection from the intercellular space of injured tobacco leaves, suggesting that WAF-1 accumulates in the intercellular space after wounding. Therefore, sclareol and WAF-1, which are both low molecular weight compounds, appear to cooperate as natural defensive mechanisms in the surface and intercellular space of plant leaves.

Example 8

Corroboration of the Damage Resistance Enhancement in Plant by Labdan-typed Diterpenoid It was indicated that the active substance of the invention obtained in this invention affected the expression of the gene encoding proteinase inhibitor II, an inhibitor of digestive enzymes in insect. Therefore, an experiment was conducted by administering this substance to plants and presenting vermin to the administered plant. In this example, rice was used as a target. Growth was regulated in the rice administered with this substance more than in the rice not administered.

Example 9

Defense from Stress

The active substance obtained in this invention was isolated from TMV-infected tobacco in which hypersensitive reaction was induced. The hypersensitive reaction confines pathogens because the infected cells in plant positively die, followed by an inhibition of pathogen growth, which is a typical example of the pathogenesis resistance reaction. With the above experiment, in the hypersensitive reaction induced with TMV, it was indicated that the endogenous amount of the substance at this invention began to increase at the initial stage of the reaction, suggesting that the substance in this invention plays an important role in hypersensitive reaction.

Figure 12:
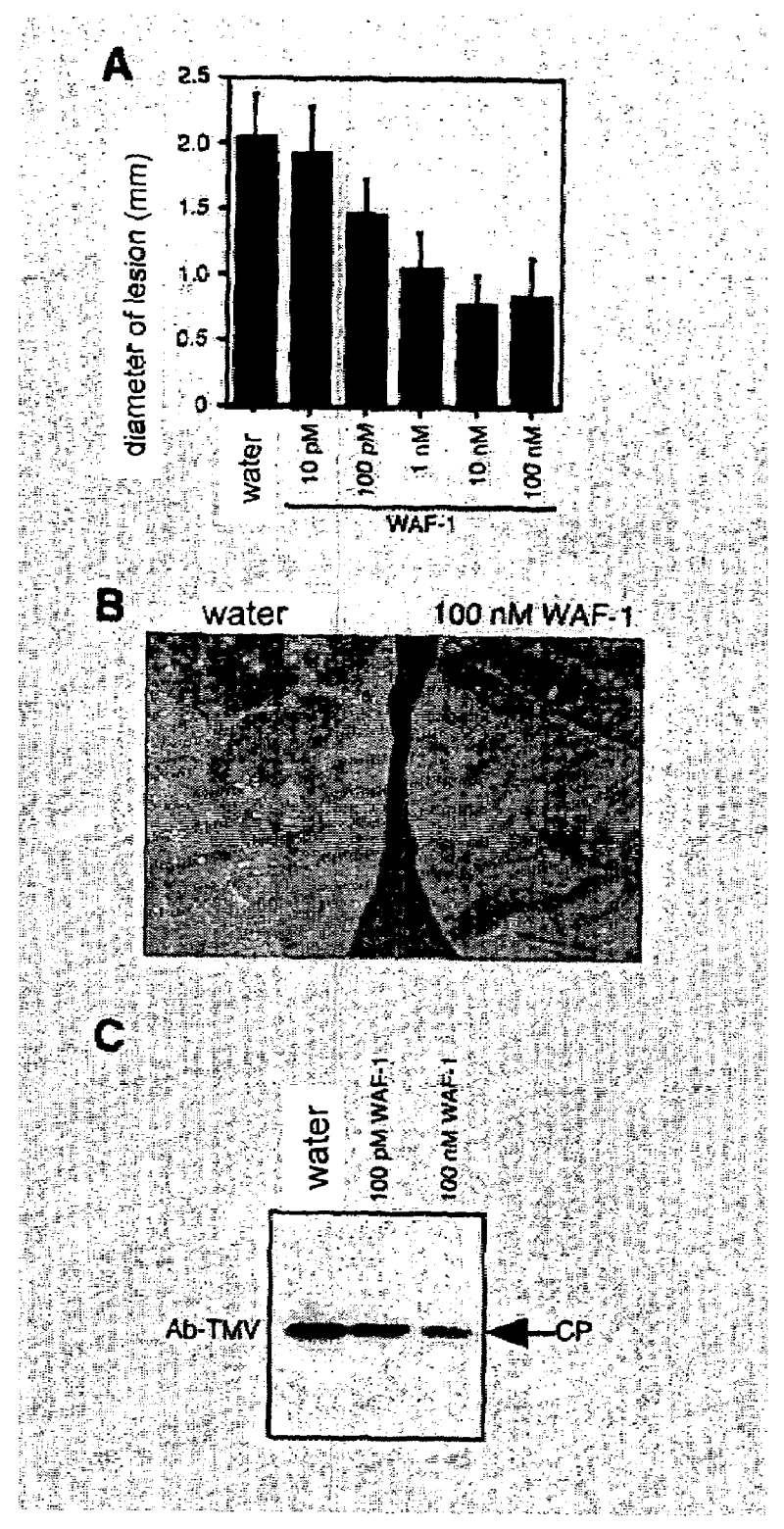

In this Example, the substance in this invention was administered to non-TMV-infected tobacco as a target. TMV stimulation was then given, under the same conditions as those in Example 1, to plants administered with the substance of this invention at the concentrations shown in FIG. 12 and tp control plant not administered to measure the size of necrotic lesions and the amount of TMV coat protein. The results are shown in FIG. 12.

(Results)

From these results, it was indicated that, in plants administered with the substance of this invention, the size of necrotic lesions decreased at concentrations higher than 100 pM and was dose-dependent. A decrease in TMV coat protein amount was also indicated, suggesting that, in the tobacco leaf treated with the substance in this invention, TMV replication was inhibited. Therefore, it was indicated that the resistance to TMV increased in the plant administered with the substance in this invention more than in the plant not administered, which corroborated that the substance in this invention gave stress resistance to plants.

Example 10

Promotion of Auxetic Growth in Plants by WAF-1

By administration of the compound of this invention, ACO was accumulated, so that the effects of the compound in this invention on auxetic growth was investigated.

(Plant Material)

In this Example, 15-day-old Arabidopsis (Arabidopsis thaliana), 1-month-old tobacco (Nicotiana tabacum cv. Samsun—NN), or 20-day-old rice (Oryza sativa) was used to provide plant bodies. The compound of this invention was dissolved in dimethyl sulfoxide (DMSO) and diluted with 10 mM Mes-NaOH (pH 5.6) to an adequate concentration (300, 100 and 30 ng/ml). 10 mM of Mes-NaOH containing the compound of this invention at the given concentration was sprayed to tobacco and rice plant bodies, followed by culture at 24° C. As a control group, 10 mM Mes-NaOH (pH 5.6) free of the compound of this invention was used. In a certain amount of time, the periphery and the height of stem above ground level were measured in rice, Arabidopsis and tobacco plant bodies.

(Result)

From these results, in comparison with the control group, a delay in growth of the periphery and height of stem was observed in Arabidopsis and tobacco plant bodies and the growth of height above ground level was observed in rice plant body in those plants administered with the compound of this invention. This indicates that the compound in this invention is involved in the growth of the periphery and the height in plant bodies and useful in regulating the growth of plant body.

Example 11

Effects of WAF-1 on Flowering

The administration of the compound in this invention induces the accumulation of ethylene in plant tissue so the effects of the compound of this invention on flowering was investigated.

(Plant Material)

In this example, 1-month-old petunia plant body was used. The compound of this invention was dissolved in dimethyl sulfoxide (DMSO) and diluted with 10 mM Mes-NaOH (pH 5.6) to an adequate concentration (300, 100 and 30 ng/ml). 10 mM Mes-NaOH containing the compound of this invention at the given concentration was sprayed on the petunia plant bodies, followed by culture at 24° C. In a control group, 10 mM Mes-NaOH (pH 5.6) without the compound of this invention was used. After a certain amount of time, observation of the gross flowering features of the plant bodies was performed. The administration of the compound of this invention to plants was then discontinued, only buffer was sprayed, and the flowering was observed.

(Results)

From these results, compared with a control group, a delay in flowering was observed in the petunia plant bodies administered with the compound of this invention, and that the discontinuation of administration led to observation of flowering, suggesting that the compound of this invention was useful at regulating flowering of plant bodies.

As described above, this invention is exemplified using the preferred examples of this invention. It is understood that the range of this invention should be interpreted only by the claims. It is understood that the content of other patents, patent applications and literatures cited in this specification should be herein incorporated by reference in their entirety as if the content itself is specifically described in this specification.

What is claimed is:

1. A compound having the following structure:

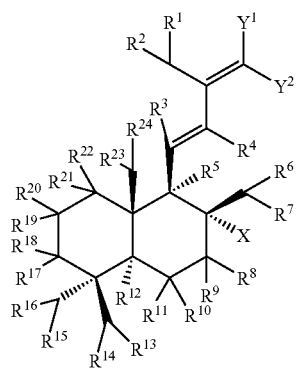

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

2. The compound of claim 1, wherein one of $Y^1$ and $Y^2$ is hydrogen, and the other is a methylol, substituted methylol, C1-aldehyde, C1-carboxyl, or substituted C1-carboxyl group.

3. The compound of claim 1, wherein all of $R^1$-$R^{24}$ are hydrogen.

4. The compound of claim 1, wherein X is hydroxy.

5. The compound of claim 1, having the following structural formula:

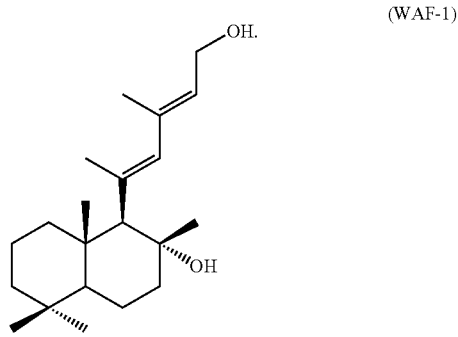

(WAF-1)

6. A composition, comprising a compound having the following structure:

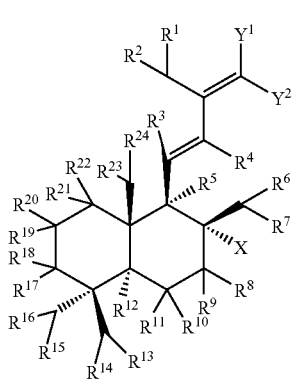

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

7. A composition for imparting stress resistance to a plant or augmenting said stress resistance, comprising a compound having the following structure:

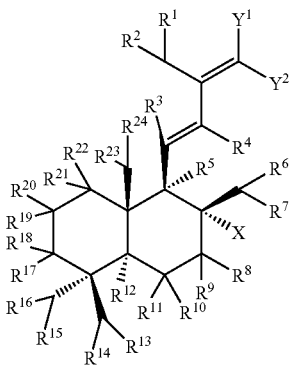

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

8. The composition of claim 7, wherein said stress resistance is at least one resistance selected from the group consisting of wound resistance, insect resistance, disease resistance, and hypersensitivity cell death resistance.

9. The composition of claim 7, wherein the imparting or augmenting of said stress resistance is accomplished by controlling the activity of at least one protein selected from the group consisting of wound-induced protein kinases, salicylic acid-induced protein kinases, pathogenesis-related proteins, and 1-amino-cyclopropane-t-carboxylic acid synthetases.

10. The composition of claim 7, wherein the imparting or augmenting of said stress resistance is accomplished by controlling at least one signaling system selected from the group consisting of jasmonic acid signaling systems and salicytic acid signaling systems.

11. A method of imparting stress resistance to a plant or augmenting said stress resistance, wherein said method comprises the following steps:

a) applying to said plant a compound having the following structure:

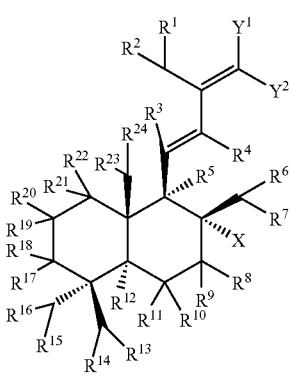

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

12. The method of claim 11, wherein said stress resistance is at least one resistance selected from the group consisting of wound resistance, insect resistance, disease resistance, and hypersensitivity cell death resistance.

13. The method of claim 11, wherein the imparting or augmenting of said stress resistance is accomplished by controlling the activity of at least one protein selected from the group consisting of wound-induced protein kinases, salicylic acid-induced protein kinases, pathogenesis-related proteins, and 1-amino-cyclopropane-t-carboxylic acid synthetases.

14. The method of claim 11, wherein the imparting or augmenting of said stress resistance is accomplished by controlling at least one signaling system selected from the group consisting of jasmonic acid signaling systems and salicylic acid signaling systems.

15. A method of producing stress resistant plants, comprising:

a) applying to said plant a compound having the following structure:

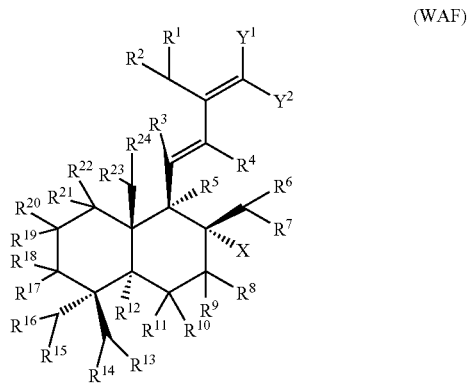

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

16. A method of producing stress resistant plant tissues, comprising:

a) applying to said plant tissue a compound having the following structure:

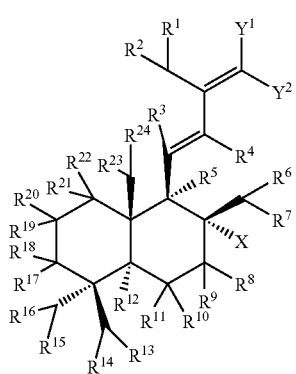

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

17. A method of producing stress resistant plant cells, comprising:

a) applying to said plant cell a compound having the following structure:

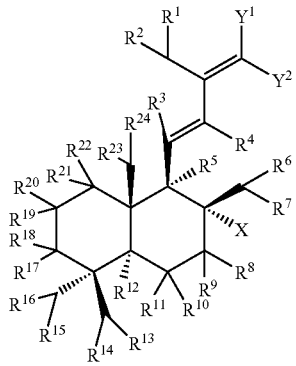

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

18. A method of producing stress resistant plant seeds, comprising:

a) applying to said plant a compound having the following structure:

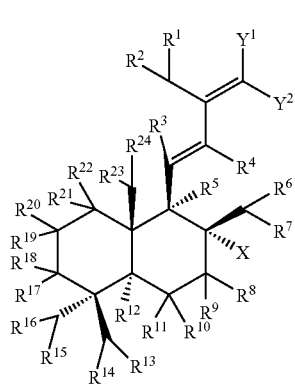

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl; and b) obtaining said seed from said plant.

19. A method of synthesizing a compound having the following structure:

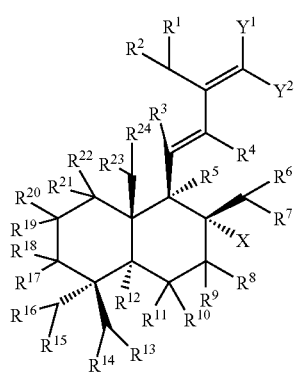

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl, said method comprises the following steps:

a) reacting a compound (an intermediate 1) having

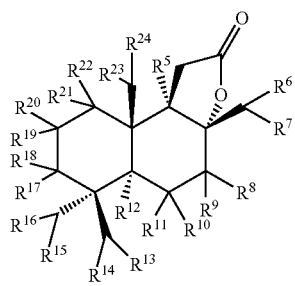

wherein, in the formula:
$R^5$-$R^{24}$ are independently selected from the group consisting of hydrogen, alkyl, and substituted alkyl, and the same as $R^1$-$R^{24}$ for WAF, with an alkyl lithium to provide an intermediate 2;

(the intermediate 2)

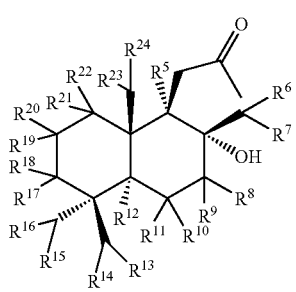

b) mixing and reacting the product obtained in a) with m-chloroperbenzoic acid and then with a 10% potassium hydroxide in methanol to provide an intermediate 4;

(the intermediate 4)

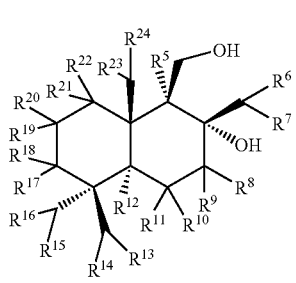

c) reacting the product obtained in b) with N-methylmorphorine N-oxide in the presence of tetrapropyl ammonium peruthenate to provide an intermediate 5;

(the intermediate 5)

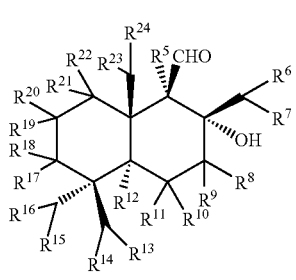

d) adding a compound

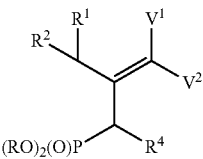

wherein, one of $V^1$ and $V^2$ is hydrogen or alkyl, and the other is Z-V, and wherein Z is (CH2)n-C(=O)—O—, V is alkyl, n is an integer of 0 or more, and R is alkyl, to said intermediate 5 obtained in the step c) in an organic solvent in the presence of $NaNH_2$ to provide an intermediate (6):

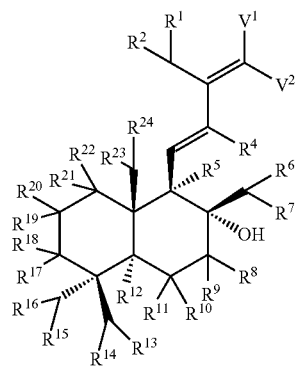

e) adding diisobutyl aluminum hydride in an organic solvent to said intermediate (6) obtained in the step d) to provide

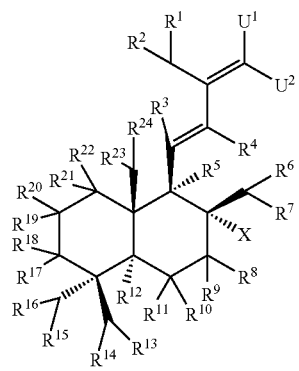

wherein, X is selected from the group consisting of hydroxy, substituted hydroxy, halogen, thiol, and substituted thiol;
one of $U^1$ and $U^2$ is hydrogen or alkyl, and the other is Z-U, wherein Z is a single bond, or a divalent group having alkane or substituted alkane having two hydrogen atoms removed, and U is hydroxy; and
$R^1$-$R^{24}$ are independently selected from the group of hydrogen, alkyl, and substituted alkyl; and optionally
a further oxidation or substitution step where $Y^1$ is other than hydroxy.

20. The method of claim 19, wherein
said X is hydroxy;
one of said $Y^1$ and $Y^2$ is hydrogen, and the other is methylol;
all of $R^1$-$R^{24}$ are hydrogen;
said organic solvent is THF;
the alkyl lithium in said step a) is methyl lithium;
one of $U^1$ and $U^2$ is hydrogen, and the other is Z-U, wherein Z is —$CH_2$—, and U is hydroxy; and
one of said $V^1$ and $V^2$ is hydrogen, and the other is —C(=O)—O—$CH_2CH_3$.

21. A method of quantifying a compound having the following structure:

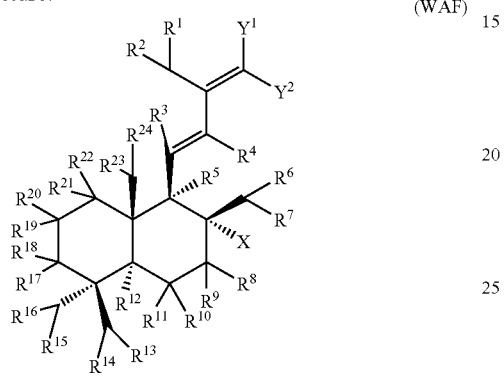

(WAF)

wherein, in the formula:
X is selected from the group consisting of hydroxy, substituted hydroxy, halogen, thiol, and substituted thiol;
one of $Y^1$ and $Y^2$ is hydrogen or alkyl, and the other is Z-W, wherein Z is a single band, or a divalent group having alkane or substituted alkane having two hydrogen atoms removed, and W is hydroxy, substituted hydroxy, aldehyde, carboxyl, or substituted carboxyl; and
$R^1$-$R^{24}$ are independently selected from the group of hydrogen, alkyl, and substituted alkyl, said method comprises the following steps:
1) providing a sample;
2) adding the predetermined amount of the steric isomer of said compound to said sample;
3) separating said sample by a reverse phase liquid chromatography; and
4) calculating the amount of said compound from said separated steric isomer.

22. The method of claim 21, wherein said compound has the following structural formula:

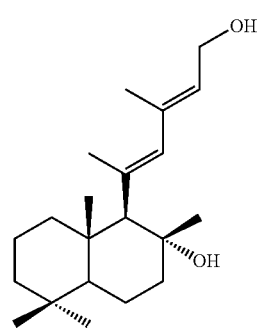

(WAF-1)

said steric isomer has the following structural formula:

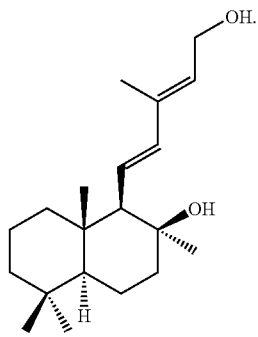

(Labdan a)

23. The method of claim 21, wherein said sample is extracted with methanol and subsequently with methyl acetate, prior to the separation with said reverse phase liquid chromatography.

24. The method of claim 21, wherein the separation with said reverse phase liquid chromatography comprises a separation with a C18 reverse phase liquid chromatography, and said separation comprises a first separation in 80%:20% (v/v) methanol:water, and a separation with 9:8 (v/v) acetonitrile:water.

25. The method of claim 21, wherein said calculation comprises the correction of the recovery loss.

26. A composition for inducing a rapid accumulation of a WRKY family gene in a plant under a condition requiring the accumulation of a WRKY family gene, said composition comprises a compound having the following structure:

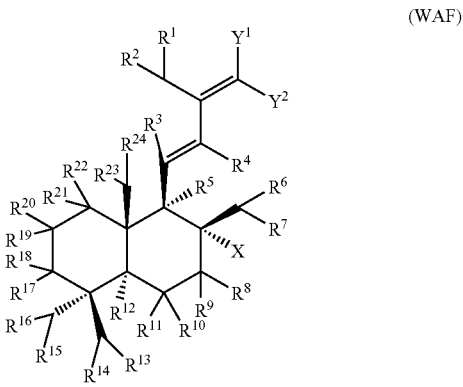

(WAF)

wherein, in the formula:
X is selected from the group consisting of hydroxy, substituted hydroxy, halogen, thiol, and substituted thiol;
one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and
$R^1$ $R^{24}$ are independently selected from the group of hydrogen, alkyl, and substituted alkyl.

27. The composition of claim 26, wherein said compound has the following structural formula:

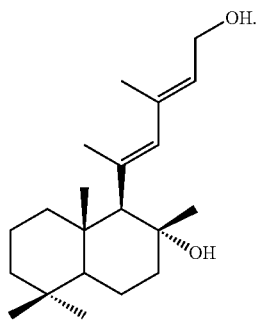
(WAF-1)

28. The composition of claim 26, wherein the condition requiring the accumulation of said WRKY family gene is a condition requiring a rapid response to stress.

29. The composition of claim 26, wherein said plant is provided with a resistance to wound resistance, insect resistance, disease resistance, and hypersensitivity cell death resistance by inducing a rapid accumulation of said WRKY family gene.

30. The composition of claim 26, wherein said WRKY family gene is WIZZ or TIZZ.

31. A composition for regulating the expression of a WRKY family gene, comprising a compound having the following structure:

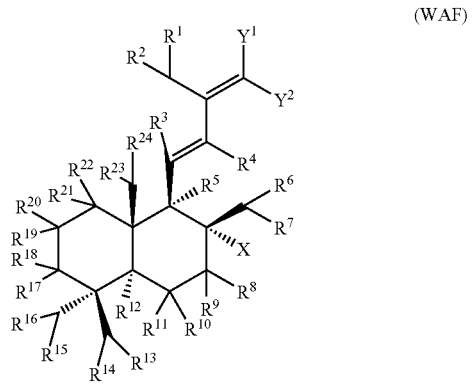
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

32. A method of inducing a rapid accumulation of a WRKY family gene in a plant under a condition requiring the accumulation of a WRKY family gene, wherein said method comprises the following steps:

a) applying to said plant a compound having the following structure:

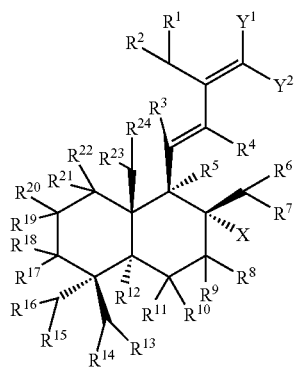
(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

33. The method of claim 32, wherein said compound has the following structural formula:

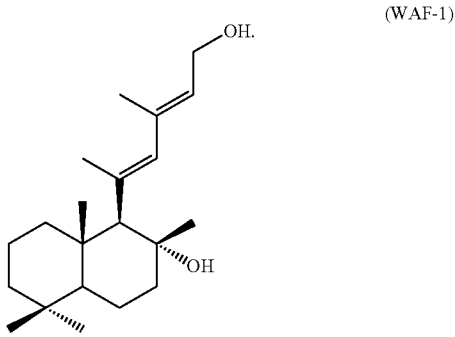
(WAF-1)

34. The method of claim 32, wherein the condition requiring the accumulation of said WRKY family gene is a condition requiring a rapid response to stress.

35. The method of claim 32, wherein said plant is provided with a wound resistance, insect resistance, disease resistance, and hypersensitivity cell death resistance by inducing a rapid accumulation of said WRKY family gene.

36. The method of claim 32, wherein said WRKY family gene is WIZZ or TIZZ.

37. The method of claim 32, wherein said compound is applied immediately after the accumulation of said WRKY family gene is required.

38. A composition for regulating the expression of a WRKY family gene, comprising the compound of claim 1.

39. A composition for facilitating the elongating growth or auxetic growth of a plant, inhibiting the elongating growth of a plant, facilitating the maturation of a plant, or regulating the flowering of a plant, said composition comprises a compound having the following structure:

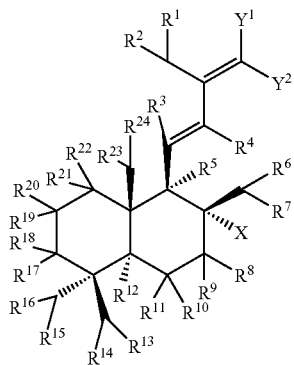

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

40. A method of facilitating the elongating growth or auxetic growth of a plant, inhibiting the elongating growth of a plant, facilitating the maturation of a plant, or regulating the flowering of a plant, said method comprises applying to a plant a compound having the following structure:

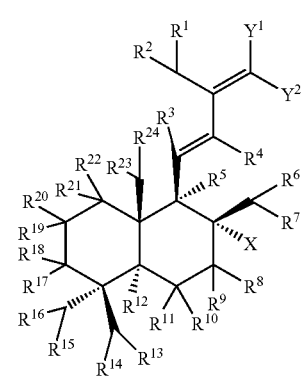

(WAF)

wherein, in the formula:

X is selected from the group consisting of hydroxy, substituted hydroxy, halogen, thiol, and substituted thiol;

one of $Y^1$ and $Y^2$ is hydrogen or alkyl, and the other is Z-W, wherein Z is a single bond, or a divalent group having alkane or substituted alkane having two hydrogen atoms removed, and W is hydroxy, substituted hydroxy, aldehyde, carboxyl, or substituted carboxyl; and $R^1$-$R^{24}$ are independently selected from the group of hydrogen, alkyl, and substituted alkyl.

* * * * *